US008431385B2

(12) United States Patent
Owen et al.

(10) Patent No.: US 8,431,385 B2
(45) Date of Patent: *Apr. 30, 2013

(54) APPARATUS AND METHOD FOR MAINTAINING AND/OR RESTORING VIABILITY OF ORGANS

(75) Inventors: Donald R. Owen, New Orleans, LA (US); David C. Kravitz, Chicago, IL (US); John Brassil, Northbrook, IL (US); Kelvin G. M. Brockbank, Charleston, SC (US); Andrew Burroughs, Kenosha, WI (US); Dickon Isaacs, Chicago, IL (US); Douglas Schein, Chicago, IL (US)

(73) Assignee: Lifeline Scientific, Inc., Itasca, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/929,410

(22) Filed: Jan. 21, 2011

(65) Prior Publication Data

US 2011/0129908 A1  Jun. 2, 2011

Related U.S. Application Data

(60) Division of application No. 12/662,930, filed on May 12, 2010, which is a division of application No. 10/617,130, filed on Jul. 11, 2003, now Pat. No. 7,824,848, which is a division of application No. 09/645,525, filed on Aug. 25, 2000, now Pat. No. 6,673,594, which is a continuation-in-part of application No. 09/537,180, filed on Mar. 29, 2000, now Pat. No. 6,977,140, and a continuation-in-part of application No. 09/162,128, filed on Sep. 29, 1998, now abandoned.

(51) Int. Cl.
*A01N 1/02* (2006.01)

(52) U.S. Cl.
USPC ........................................ 435/284.1; 435/1.2

(58) Field of Classification Search ................... 435/1.2, 435/284.1
See application file for complete search history.

(56) References Cited

U.S. PATENT DOCUMENTS

| | | | |
|---|---|---|---|
| 1,682,344 A | 8/1928 | Lesieur |
| 1,916,658 A | 7/1933 | Davidson |
| 3,406,531 A | 10/1968 | Swenson et al. |
| 3,521,743 A | 7/1970 | Sposito |
| 3,545,221 A | 12/1970 | Swenson et al. |
| 3,607,646 A | 9/1971 | de Roissart |
| 3,632,473 A | 1/1972 | Belzer |
| 3,639,084 A | 2/1972 | Goldhaber |
| 3,654,085 A | 4/1972 | Norr et al. |
| 3,660,241 A | 5/1972 | Michielsen |
| 3,712,583 A | 1/1973 | Martindale et al. |
| 3,738,914 A | 6/1973 | Thorne et al. |
| 3,753,865 A | 8/1973 | Belzer et al. |
| 3,772,153 A | 11/1973 | de Roissart |
| 3,777,507 A | 12/1973 | Burton et al. |
| 3,810,367 A | 5/1974 | Peterson |
| 3,843,455 A | 10/1974 | Bier |
| 3,845,974 A | 11/1974 | Pelloux-Gervais |
| 3,877,843 A | 4/1975 | Fischel |
| 3,881,990 A | 5/1975 | Burton et al. |
| 3,892,628 A | 7/1975 | Thorne et al. |
| 3,914,954 A | 10/1975 | Doerig |
| 3,935,065 A | 1/1976 | Doerig |
| 3,962,439 A | 6/1976 | Yokoyama et al. |
| 3,995,444 A | 12/1976 | Clark et al. |
| 4,186,565 A | 2/1980 | Toledo-Pereyra |
| 4,231,354 A | 11/1980 | Kurtz et al. |
| 4,242,883 A | 1/1981 | Toledo-Pereyra |
| 4,243,883 A | 1/1981 | Schwarzmann |
| 4,378,797 A | 4/1983 | Osterholm |
| 4,393,863 A | 7/1983 | Osterholm |
| 4,445,500 A | 5/1984 | Osterholm |
| 4,451,251 A | 5/1984 | Osterholm |
| 4,462,215 A | 7/1984 | Kuraoka et al. |
| 4,471,629 A | 9/1984 | Toledo-Pereyra |
| 4,473,637 A | 9/1984 | Guibert |
| 4,474,016 A | 10/1984 | Winchell |
| 4,494,385 A | 1/1985 | Kuraoka et al. |
| 4,502,295 A | 3/1985 | Toledo-Pereyra |
| 4,559,298 A | 12/1985 | Fahy |
| 4,596,250 A | 6/1986 | Beisang, III et al. |
| 4,618,586 A | 10/1986 | Walker |
| 4,629,686 A | 12/1986 | Gruenberg |
| 4,657,532 A | 4/1987 | Osterholm |

| | | |
|---|---|---|
| 4,666,425 A | 5/1987 | Fleming |
| 4,704,029 A | 11/1987 | Van Heuvelen |
| 4,717,548 A | 1/1988 | Lee |
| 4,723,974 A | 2/1988 | Ammerman |
| 4,745,759 A | 5/1988 | Bauer et al. |
| 4,766,740 A | 8/1988 | Bradley et al. |
| 4,801,299 A | 1/1989 | Brendel et al. |
| 4,837,390 A | 6/1989 | Reneau |
| 4,879,283 A | 11/1989 | Belzer et al. |
| 4,951,482 A | 8/1990 | Gilbert |
| 4,958,506 A | 9/1990 | Guilhem et al. |
| 4,976,593 A | 12/1990 | Miyamoto |
| 5,003,787 A | 4/1991 | Zlobinsky |
| 5,013,303 A | 5/1991 | Tamari et al. |
| 5,028,588 A | 7/1991 | Hoffman et al. |
| 5,036,097 A | 7/1991 | Floyd et al. |
| 5,047,395 A | 9/1991 | Wu |
| 5,051,352 A | 9/1991 | Martindale et al. |
| 5,066,578 A | 11/1991 | Wikman-Coffelt |
| 5,085,630 A | 2/1992 | Osterholm et al. |
| 5,110,721 A | 5/1992 | Anaise et al. |
| 5,130,230 A | 7/1992 | Segall et al. |
| 5,141,847 A | 8/1992 | Sugimachi et al. |
| 5,145,771 A | 9/1992 | Lemasters et al. |
| 5,149,321 A | 9/1992 | Klatz et al. |
| 5,150,706 A * | 9/1992 | Cox et al. ................ 607/105 |
| 5,157,930 A * | 10/1992 | McGhee et al. ............ 62/78 |
| 5,200,176 A | 4/1993 | Wong et al. |
| 5,216,032 A | 6/1993 | Manning |
| 5,217,860 A | 6/1993 | Fahy et al. |
| 5,234,405 A | 8/1993 | Klatz et al. |
| 5,285,657 A | 2/1994 | Bacchi et al. |
| 5,326,706 A | 7/1994 | Yland et al. |
| 5,328,821 A | 7/1994 | Fisher et al. |
| 5,338,662 A | 8/1994 | Sadri |
| 5,356,771 A | 10/1994 | O'Dell |
| 5,362,622 A | 11/1994 | O'Dell et al. |
| 5,383,854 A | 1/1995 | Safar et al. |
| 5,385,821 A | 1/1995 | O'Dell et al. |
| 5,395,314 A | 3/1995 | Klatz et al. |
| 5,434,045 A | 7/1995 | Jost |
| 5,437,633 A | 8/1995 | Manning |
| 5,451,524 A | 9/1995 | Coble et al. |
| 5,472,876 A | 12/1995 | Fahy |
| 5,476,763 A | 12/1995 | Bacchi et al. |
| 5,494,822 A | 2/1996 | Sadri |
| 5,584,804 A | 12/1996 | Klatz et al. |
| 5,586,438 A | 12/1996 | Fahy |
| 5,599,659 A | 2/1997 | Brasile et al. |
| 5,622,429 A | 4/1997 | Heinze |
| 5,643,712 A | 7/1997 | Brasile |
| 5,681,740 A | 10/1997 | Messier et al. |
| 5,699,793 A | 12/1997 | Brasile |
| 5,702,881 A | 12/1997 | Brasile et al. |
| 5,712,084 A | 1/1998 | Osgood |
| 5,716,378 A | 2/1998 | Minten |
| 5,723,282 A | 3/1998 | Fahy et al. |
| 5,730,720 A | 3/1998 | Sites et al. |
| 5,821,045 A | 10/1998 | Fahy et al. |
| 5,823,986 A | 10/1998 | Peterson |
| 5,843,024 A | 12/1998 | Brasile |
| 5,856,081 A | 1/1999 | Fahy |
| 5,879,329 A | 3/1999 | Ginsburg |
| 5,894,266 A | 4/1999 | Wood, Jr. et al. |
| 5,928,182 A | 7/1999 | Kraus et al. |
| 5,965,433 A | 10/1999 | Gardetto et al. |
| 6,024,698 A | 2/2000 | Brasile |
| 6,046,046 A | 4/2000 | Hassanein |
| 6,100,082 A | 8/2000 | Hassanein |
| 6,238,908 B1 | 5/2001 | Armstrong et al. |
| 6,300,875 B1 | 10/2001 | Schafer |
| 6,642,045 B1 * | 11/2003 | Brasile ................ 435/284.1 |
| 6,673,594 B1 | 1/2004 | Owen et al. |
| 7,045,279 B1 | 5/2006 | Laske et al. |
| 7,678,563 B2 | 3/2010 | Wright et al. |
| 7,824,848 B2 | 11/2010 | Owen et al. |

FOREIGN PATENT DOCUMENTS

| | | |
|---|---|---|
| DE | 2 226 482 | 1/1973 |
| DE | 221 361 | 4/1985 |
| DE | 38 08 942 | 9/1989 |
| EP | 0 096 997 | 12/1983 |
| EP | 0 256 653 | 2/1988 |
| EP | 0 297 723 | 1/1989 |
| EP | 0 376 763 A2 | 7/1990 |
| EP | 376 763 | 7/1990 |
| EP | 376763 A * | 7/1990 |
| EP | 1 208 748 A1 | 5/2002 |
| EP | 1 929 863 A1 | 6/2008 |
| FR | 545332 | 10/1922 |
| FR | 2 592 306 | 12/1985 |
| FR | 2 718 643 | 10/1995 |
| GB | 1442356 A | 7/1976 |
| GB | 2 305 568 A | 4/1997 |
| JP | A-61-218501 | 9/1986 |
| JP | 1-213276 | 8/1989 |
| JP | A-01-308201 | 12/1989 |
| JP | 02069401 A * | 3/1990 |
| JP | 2-258701 | 10/1990 |
| SU | 760972 | 9/1980 |
| SU | 163 242 8 | 7/1991 |
| WO | WO 86/00812 | 2/1986 |
| WO | WO 88/05261 | 7/1988 |
| WO | WO 91/03934 | 4/1991 |
| WO | WO 91/09520 | 7/1991 |
| WO | WO 91/14364 | 10/1991 |
| WO | WO 92/19843 | 11/1992 |
| WO | 93/00808 | 1/1993 |
| WO | 94/06292 | 3/1994 |
| WO | WO 94/06292 | 3/1994 |
| WO | 96/05727 | 2/1996 |
| WO | WO 96/12191 | 4/1996 |
| WO | WO 96/13288 | 5/1996 |
| WO | 96/32074 | 10/1996 |
| WO | 96/32157 | 10/1996 |
| WO | WO 96/29865 | 10/1996 |
| WO | WO 96/30111 | 10/1996 |
| WO | WO 96/31779 | 10/1996 |
| WO | WO 96/41525 | 12/1996 |
| WO | WO 97/22003 | 6/1997 |
| WO | WO 97/28449 | 8/1997 |
| WO | WO 97/43899 | 11/1997 |
| WO | WO 97/45527 | 12/1997 |
| WO | WO 97/46091 | 12/1997 |
| WO | WO 98/09166 | 3/1998 |
| WO | WO 99/15011 | 4/1999 |
| WO | WO 00/18226 | 4/2000 |
| WO | WO 01/01774 A1 | 1/2001 |

OTHER PUBLICATIONS

Office Action issued in U.S. Appl. No. 12/662,930 on Mar. 28, 2011.

"Glutathione S-Transferase Predicts Outcome of Machine Preserved NHBD Kidneys", J.H. Loemen and C. Kootstra, Abstract submitted for presentation at XVIth International Congress of the Transplantation Society, Aug. 1996.

"Renal Preservation After Warm Ischemia Using Oxygen Free Radical Scavengers to Prevent Reperfusion Injury", Pedro Baron et al., *Journal of Surgical Research*, vol. 51, pp. 60-65, 1991.

"Organ Preservation", J.H. Southard, Ph.D. and F.O. Belzer, M.D., *Principles of Organ Transplantation*, Chapter 10, pp. 194-215, 1989.

"Organko Servierungsmachine OKM 82", Von Dietmer Scholz et al., East German Article, 1983.

"Arrest of Cerebral Blood Flow and Reperfusion of the Brain in the Rhesus Monkey", L.R. Wolin, L.C. Massopust, Jr., R.J. White and N. Taslitz, *Resuscitation*, vol. I 39, 1972.

"Nutritional Aspects of Ambulatory Care-Oxygen Radicals and Disease—No. 1", Hoffmann-La Roche, vol. 42, No. 3, pp. 557-558, Sep. 1990.

"Cerebral Ischemic Injury", Blaine C. White, *Emergency Medicine—A Comprehensive Study Guide*, Second Edition, pp. 9-10, 1988.

"Cerebral Blood Flow, Vasoreactivity, and Oxygen Consumption During Barbiturate Therapy in Severe Traumatic Brain Lesions"

Carl-Henrik Nordstrom et al., *J. Neurosurg.*, vol. 68, pp. 424-431, Mar. 1988.
"At Surgery's Frontier: Suspended Animation", *New York Times*, C1, C2, Nov. 13, 1990.
"Randomized Clinical Study of Thiopental Loading in Comatose Survivors of Cardiac Arrest", *The New England Journal of Medicine*, vol. 314, No. 7, pp. 397-403, Feb. 1996.
"Current Concepts in Brain Resuscitation", Mark C. Rodgers et al., *J. American Medical Assn.*, vol. 261, No. 21, pp. 3143-3147, Jun. 1989.
U.S. Appl. No. 60/459,986, filed Apr. 4, 2002, David W. Wright et al.
U.S. Appl. No. 60/459,981, filed Apr. 4, 2003, David W. Wright et al.
U.S. Appl. No. 60/460,875, filed Apr. 8, 2003, David W. Wright et al.
"Cerebrovascular Hypoxic and Autoregulatory Responses During Reduced Brain Metabolism", Judith H. Donegan et al., *Am. J. Physiol.*, vol. 249, pp. H421-H429, 1985.
"Regional Cerebral Blood Flow in Normal Blood Circulated and Perfluorocarbon Transfused Rats", P.A. Lee et al., *Adv. Exp. Med. Biol.*, vol. 200, pp. 59-65, 1986.
"Protection From Cerebral Air Emboli With Perfluorocarbons in Rabbits", Bruce D. Spiess, M.D. et al., *Stroke*, vol. 17, No. 6, pp. 1146-1149, 1986.
"Free Radicals and Myocardial Ischemia and Reperfusion Injury", Paul J. Simpson et al., *J Lab Cin Med.*, pp. 13-30, Jul. 1987.
"Increases in Brain Tumor and Cerebral Blood Flow by Blood-Perfluorochemical Emulsion (Fluosol-Da) Exchange", Shoju Hiraga et al., *Cancer Research*, vol. 47, pp. 3296-3302, Jun. 15, 1987.
"Polarographic Cerebral Oxygen Availability, Fluorcarbon Blood Levels and Efficacy of Oxygen Transport by Emulsions", Leland C. Clark Jr. et al., *Biomaterials*, vol. 16(1-3), pp. 375-393, 1988.
"Easier Breathing in RDS", J.C., *Medical Tribune*, Jan. 11, 1990.
"90's Could See Brain Injury Reversal", Rebecca Voelker, *American Medical News*, Nov. 17, 1989.
"Cooling Brain May Limit Stroke Damage", *American Medical News*, p. 66, Nov. 17, 1989.
"Drug May Preserve Heart Tissue After Attack", *The New York Times Company*, p. 3, Sep. 5, 1989.
"Radical Therapy", *Scientific American*, Sep. 1987.
"Resuscitation of the Rabbit Brain After Acute Complete Ischemia Lasting Up to One Hour: Pathophysiological and Pathomorphological Observations", Ryszard Pluta, *Resuscitation*, vol. 15, pp. 267-287, 1987.
"Diseases of the Nervous System", Arthur K. Asbury et al., vol. 2, pp. 1071 and 1083, 1986.
"In Situ Cadaver Kidney Perfusion", Robert T. Schweizer et al. *Transplantation*, vol. 32, No. 6, pp. 482-484, Dec. 1981.
"Use of Extracorporeal Cadaver Perfusion for Preparation of Organ Homografts", T.L. Marchioro et al., *Surgical Forum*, vol. XIV, pp. 174-176, 1963.
"Preservation of Cerebral Function During Circulatory Arrest and Resuscitation: Hypothermic Protective Considerations", Robert J. White, *Resuscitation*,, vol. I, pp. 107-115, 1972.
"In Situ Kidney Preservation for Transplantation With Use of Profound Hypothermia (5 to 20° C.) With an Intact Circulation", A. R. Moossa et al., *Society for Vascular Surgery*, vol. 79, No. 1, pp. 60-64, Jan. 1976.
"Annals of Clinical and Laboratory Science", F. William Sunderman, M.D., Ph.D., *Official Journal of the Association of Clinical Scientists*, vol. 20, No. 4, p. 292, Jul.-Aug. 1990.
"Extracorporeal Perfusion for Obtaining Postmorten Homografts", T.L. Marchioro et al., *Surgery*, vol. 54, No. 6, pp. 900-911, Jul.-Dec. 1963.
"The Nature of Fluorocarbon Enhanced Cerebral Oxygen Transport", Leland C. Clark et al., *Adv. Exp. Med. Biol.*, vol. 248, pp. 341-355, 1989.
"Storage and Transport of Heart and Heart-Lung Donor Organs With Inflatable Cushions and Eutectoid Cooling", D.R. Wheeldon et al., *The Journal of Heart Transplantation*, vol. 7, pp. 265-268, 1988.
"Decreased Nephrotoxicity After the Use of Microemulsion Formulation of Cyclosporine A Compared to Conventional Solution", J. Ahlmén et al., *Transplantation Proceedings*, vol. 27, No. 6, pp. 3432-3433, Dec. 1995.

"Development of an Isolated Perfused Dog Kidney With Improved Function", William H. Waugh et al., *American Journal of Physiology*, vol. 217, No. I, Jul. 1969.
"Low Cost Apparatus for Primer-Directed DNA Amplification Using *Thermus aquaticus*-DNA Polymerase", Helge Torgersen et al., *Analytical Biochemistry*, vol. 176, pp. 33-35, 1989.
"Simple Programmable Apparatus for Enzymatic DNA Amplification", Royal A. McGraw et al., *DNA and Protein Engineering Techniques*, vol. 1, No. 5, pp. 65-67, 1988.
"An Organ Cryopreservation Apparatus", Michael G. O'Callaghan et al., *IEEE Transactions on Biomedical Engineering*, vol. BME-24, No. 2, pp. 111-115, Mar. 1997.
"Transplantation of Rabbit Kidneys Perfused With Glycerol Solutions At 10° C.", I.A. Jacobsen et al., *Cryobiology*, vol. 15, pp. 18-26, 1978.
"Distribution of Removal of Glycerol by Vascular Albumin Perfusion in Rabbit Kidneys", IB A. Jacobsen, *Cryobiology*, vol. 15, pp. 302-311, 1978.
"Banking of Cells, Tissues, and Organs At Low Temperatures", David E. Pegg, *Current Trends in Cryobiology*, Plenum Press, NY, pp. 153-180, 1970.
"Activation of Alpha Adrenergic Vasoconstrictor Response in Kidneys Stored At −30° C. for Up to 8 Days", Gregory M. Fahy, *Cryo-Letters*, vol. 1, pp. 312-317, 1980.
"Histological Cryoprotection of Rat and Rabbit Brains", G.M. Fahy et al., *Cryo-Letters*, vol. 5, pp. 33-46, 1984.
"Vitrification As an Approach to Cryopreservation", G.M. Fahy et al., *Cryobiology*, vol. 21, pp. 407-426, 1984.
"A Fully Automated System for Treating Organs With Cryoprotective Agents", G.M. Fahy et al., *Cryobiology*, vol. 22, pp. 607-608, 1985.
"Perfusion of Rabbit Kidneys With Cryoprotective Agents", D.E. Pegg, *Cryobiology*, vol. 9, pp. 411-419, 1972.
"Perfusion of Rabbit Kidneys With Glycerol Solutions At 5° C.", D.E. Pegg et al., *Cryobiology*, vol. 14, pp. 168-178, 1977.
"MOX®-100 Renal Preservation System", Waters Instruments Medical Group, pp. 2-7, 1982.
"Engineering Aspects of Equipment Design for Subzero Organ Preservation", G.J. Sherwood et al., *Organ Preservation*, Chapter 15, pp. 152-174, 1973.
"Organ Perfusion Systems: An Evaluation Criteria", Fereydoon Sadri, Ph.D. *T.O.P.S. Medical Corporation*, pp. 1-8, 1987.
"Seleno-Dl-Methionine Reduces Freezing Injury in Hearts Protected With Ethanediol", W.J. Armitage et al., *Cryobiology*, vol. 18, pp. 370-377, 1981.
"Isolated Perfusion of Whole Organs", F.O. Belzer et al., *Preservation*, Chapter 1, pp. 3-12, 1968.
"Variations in Vascular Resistance of Isolated Rat Hearts During Normothermic and Hypotermic Experiments", C.G. Adem et al., *J. Biomed. Engng.*, vol. 3(2), pp. 128-133, 1981.
"Computer Control of a Modified Langendorff Perfusion Apparatus for Organ Preservation Using Cryoprotective Agents", C.G. Adem et al., *J. Biomed. Engng.*, vol. 3, pp. 134-139, Apr. 1981.
"Effect of Pharmacologic Agents on the Function of the Hypothermically Preserved Dog Kidney During Normothermic Reperfusion", Rutger J. Ploeg et al., *Surgery*, vol. 103, No. 6, pp. 676-682, Jun. 1988.
"Intermediate Normothermic Perfusion During Cold Storage of Ischemically Injured Kidneys", J.G. Maessen et al., *Transplantation Proceedings*, vol. 21, No. 1, pp. 1252-1253, Feb. 1989.
"The Beneficial Effect of Intermediate Normothermic Perfusion During Cold Storage of Ischemically Injured Kidneys", Jos G. Maessen et al., *Transplantation*, vol. 47, No. 3, pp. 409-414, Mar. 1989.
"The Asystolic, or Non-Heartbeating, Donor", Gauke Kootstra, *Transplantation*, vol. 63, No. 7, pp. 917-921, 1997.
"The Use of Hemoglobin Solutions in Kidney Perfusions", F.H. Daniels et al., *CRC Critical Reviews in Biomedical Engineering*, vol. 9, Issue 4, pp. 315-345, 1984.
"Normothermic Renal Artery Perfusion: A Comparison of Perfusates", John D. Hughes et al., *Annals of Vascular Surgery*, vol. 10, pp. 123-130, 1996.
"Is Normothermic Preservation an Alternative to Hypothermic Preservation?", R. N. Dunn et al., *Organ Preservation Basic and Applied Aspects*, Chapter 38, pp. 273-277, 1982.

"Mild Hypothermia Gives Better Functional Preservation Than Cold or Normothermic Perfusion of Rat Kidneys", B.L. Kasiske et al., *Transplantation Proceedings*, vol. 22, No. 2, pp. 472-473, Apr. 1990.

"Studies of Controlled Reperfusion After Ischemia", Pierre L. Julia, MD et al., *The Journal of Thoracic and Cardiovascular Surgery*, vol. 101, No. 2, pp. 303-313, Feb. 1991.

"Urinary π-Class Glutathione Transferase As an Indicator of Tubular Damage in the Human Kidney", Dr. Anders Sundberg et al., *Nephron*, vol. 67, pp. 308-316, 1994.

"Effect of Ischemia and 24 Hour Reperfusion on ATP Synthesis in the Rat Kidney", C.E. Irazu et al., *Journal of Experimental Pathology*, vol. 4, No. 1, pp. 29-36, 1989.

"Intermediate Normothermic Hemoperfusion of Rat Kidneys: Functional Aspects and a Study Into the Effect of Free Radical Scavengers", A.O. Gaber, *Transplantation Proceedings*, vol. XX, No. 5, pp. 896-898, Oct. 1998.

"Improvement of Postischemic Kidney Function by Reperfusion With a Specifically Developed Solution (BT01)", Pierre Julia, MD et al., *Annals of Vascular Surgery*, vol. 9, pp. s-81-s-88, 1995.

"Ischemia With Intermittent Reperfusion Reduces Functional and Morphologic Damage Following Renal Ischemia in the Rat", Richard S. Frank, MD et al., *Annals of Vascular Surgery*, vol. 7, No. 2, pp. 150-155, 1993.

"Graft Conditioning of Liver in Non-Heart-Beating Donors by an Artificial Heart and Lung Machine in Situ", T. Endoh et al., *Transplantation Proceedings*, vol. 28, No. 1, pp. 110-115, Feb. 1996.

"Machine Perfusion of Isolated Kidney At 37° C. Using Pyridoxalated Hemoglobin-Polyoxyethlene (PHP) Solution, UW Solution and Its Combination", T. Horiuchi et al., *Biomaterials, Art. Cells & Immob. Biotech*, vol. 20, Nos. 2-4,, pp. 549-555, 1992.

"Analysis of the Optimal Perfusion Pressure and Flow Rate of the Renal Vascular Resistance and Oxygen Consumption in the Hypothermic Perfused Kidney", R. Grundmann, M.D. et al., *Surgery*, vol. 77, No. 3, pp. 451-461, Mar. 1975.

"An Experimental Model for Assessment of Renal Recovery From Warm Ischemia", Paula Jablonski et al., *Transplantation*, vol. 35, No. 3, pp. 198-204, Mar. 1983.

"Preservation of the Isolated Kidney Under Normothermic Conditions by Perfusion With Perfluorotributylamine Emulsion", N.N. Kontuganov et al., Article published by Plenum Publishing Corporation, pp. 371-374, 1983.

B.G. Rijkmans et al., "Six-Day Canine Kidney Preservation, Hypothermic Perfusion Combined with Isolated Blood Perfusion," Feb. 1984, pp. 130-134.

Jan Van Der Wijk et al., "Six-Day Kidney Preservation in a Canine Model, Influence of a One-to-Four-Hour Ex Vivo Perfusion Interval," May 1983, pp. 408-411.

M.R. Buhl et al, "The Postanoxic Regeneration of 5'-Adenine Nucleotides in Rabbit Kidney Tissue during In Vitro Perfusion," 1976, pp. 175-181.

Gauke Kootstra et al, "A New Device Towards Intermediate Term Kidney Preservation—An Experimental Study," 1980, pp. 86-89.

Ilinskaja et al. "Alternations of the renal function in the isolated perfused rat kidney system after in vivo and in vitro application of S-(1,2-dichlorovinyl)-L-cysteine and S-2,2-dichinorovinyl)-L-cysteine," Archives of Toxicology 1996, pp. 224-229, vol. 70, No. 3-4.

Jul. 14, 2011 Office Action issued in U.S. Appl. No. 12/926,277.
Oct. 6, 2011 Office Action issued in U.S. Appl. No. 13/137,384.
Oct. 17, 2011 Office Action issued in U.S. Appl. No. 13/137,386.
Oct. 26, 2011 Office Action issued in U.S. Appl. No. 11/257,066.
Nov. 8, 2011 Office Action issued in U.S. Appl. No. 13/064,497.
Nov. 14, 2011 Office Action issued in U.S. Appl. No. 12/926,277.

Tabet, J. et al. "Non-Heart-Beating Donor Pigs: The Feasibility of Liver Donation." Transplantation Proceedings, vol. 29, pp. 1374-1375. (1997).

Das, S. et al. "Effects of Preliminary Normothermic Flushing of Hypothermic Renal Preservation." Urology, vol. 14, No. 5, pp. 505-508. (1979).

Pegg, D. et al. "The Functional State of Kidneys Perfused at 37° C. with a Bloodless Fluid." Journal of Surgical Research, vol. 15, pp. 218-225. (1973).

Yanaga et al. "A New Liver Perfusion and Preservation System for Transplantation Research in Large Animals." J. Invest. Surg. vol. 3, No. 1 (1990) pp. 65-75.

Sep. 15, 2011 Office Action issued in EP Application No. 06024444.9.
May 8, 2008 Search Report issued in EP Application No. 06024444.9.
Jul. 22, 2011 Search Report issued in EP Application No. 10184021.3.
Jun. 24, 2011 Search Report issued in EP Application No. 10179481.6.
Apr. 27, 2011 Search Report issued in EP Application No. 10183951.2.
Jun. 27, 2011 Search Report issued in EP Application No. 10179523.5.
Aug. 2, 2011 Search Report issued in EP Application No. 10179494.9.
Jun. 29, 2011 Search Report issued in EP Application No. 10179870.0.
Jun. 24, 2011 Search Report issued in EP Application No. 10180598.4.
Aug. 8, 2011 Search Report issued in EP Application No. 10180682.6.
Jul. 27, 2011 Search Report issued in EP Application No. 10181340.0.
Jul. 6, 2011 Search Report issued in EP Application No. 10182445.6.
Jun. 20, 2011 Search Report issued in EP Application No. 10182337.5.
Aug. 8, 2011 Search Report issued in EP Application No. 10181356.6.
Jun. 27, 2011 Search Report issued in EP Application No. 10183797.9.
Jul. 25, 2011 Search Report issued in EP Application No. 10183836.5.
Aug. 29, 2011 Office Action issued in U.S. Appl. No. 12/662,930.
Jan. 30, 2012 Office Action issued in U.S. Appl. No. 12/926,276.

Borgström, P. et al., "A servo-controlled roller pump for constant flow or constant pressure blood perfusion under normal pulsatile or non-pulsatile conditions," *Acta Physical Scandinavica*, Aug. 1981, pp. 437-442, vol. 112, No. 4.

Hoffman, B.F. et al., "A Pulsatile Roller Pump for Cardiac Bypass," *IEEE Transactions on Bio-Medical Engineering*, Jan. 1970, pp. 78-80, vol. 17, No. 1.

Kiuchi, T. et al., "Background and Prognostic Implications of Perireperfusion Tissue Injuries in Human Liver Transplants," *Transplantation*, Sep. 1998, pp. 737-747, vol. 66, No. 6.

Daemen, J.H.C. et al., "Short-term outcome of kidney transplants from non-heart-beating donors after preservation by machine perfusion," *Transpl Int*, 1996, pp. S76-S80.

Nov. 15, 2011 Extended European Search Report issued in European Patent Application No. 10183797.9.
Nov. 15, 2011 Extended European Search Report issued in European Patent Application No. 10179512.8.
Dec. 6, 2011 Partial European Search Report issued in European Patent Application No. 10179853.6.
Dec. 14, 2011 Office Action issued in U.S. Appl. No. 12/910,308.
Dec. 22, 2011 Office Action issued in U.S. Appl. No. 13/137,385.
Dec. 23, 2011 Office Action issued in U.S. Appl. No. 13/137,387.
Mar. 23, 2012 European Search Report issued in EP Application No. 10179853.6.
Apr. 5, 2012 Office Action issued in U.S. Appl. No. 12/910,308.
Apr. 18, 2012 Office Action issued in U.S. Appl. No. 12/926,277.
May 3, 2012 Office Action issued in U.S. Appl. No. 13/137,387.
Apr. 25, 2012 Office Action issued in U.S. Appl. No. 13/137,385.
Apr. 26, 2012 Office Action issued in U.S. Appl. No. 13/137,384.
May 2, 2012 Office Action issued in U.S. Appl. No. 13/137,383.
Feb. 16, 2012 Office Action issued in U.S. Appl. No. 12/662,930.
Jun. 21, 2012 Notice of Allowance issued in U.S. Appl. No. 13/137,386.
Jul. 16, 2012 Notice of Allowance issued in U.S. Appl. No. 11/257,066.
Dec. 7, 2012 Notice of Allowance issued in U.S. Appl. No. 12/926,277.

Aug. 16, 2012 Notice of Allowance issued in U.S. Appl. No. 12/910,308.
Sep. 4, 2012 Notice of Allowance issued in U.S. Appl. No. 13/064,497.
Linzell et al. "The Isolated Perfused Liver of the Sheep: An Assessment of its Metabolic, Synthetic and Excretory Functions." J. Exp. Physiol, vol. 56 (1971), pp. 53-71.
Aug. 27, 2012 Office Action issued in U.S. Appl. No. 13/137,387.
Aug. 31, 2012 Office Action issued in U.S. Appl. No. 13/137,385.
Aug. 28, 2012 Office Action issued in U.S. Appl. No. 12/296,277.
Jun. 15, 2012 Office Action issued in U.S. Appl. No. 12/662,930.
May 31, 2012 Office Action issued in U.S. Appl. No. 12/926,276.
Sep. 17, 2012 Office Action issued in U.S. Appl. No. 13/137,383.
Sep. 27, 2012 Notice of Allowance issued in U.S. Appl. No. 12/926,276.
Nov. 9, 2012 Office Action issued in U.S. Appl. No. 12/662,930.
Jan. 22, 2013 Notice of Allowance and Fees Due issued in U.S. Appl. No. 13/137,383.

* cited by examiner

*Primary Examiner* — William H Beisner
(74) *Attorney, Agent, or Firm* — Oliff & Berridge, PLC

(57) ABSTRACT

An organ perfusion apparatus and method monitor, sustain and/or restore viability of organs and preserve organs for storage and/or transport. Other apparatus include an organ transporter, an organ cassette and an organ diagnostic device. The method includes perfusing the organ at hypothermic and/or normothermic temperatures, preferably after hypothermic organ flushing for organ transport and/or storage. The method can be practiced with prior or subsequent static or perfusion hypothermic exposure of the organ. Organ viability is restored by restoring high energy nucleotide (e.g., ATP) levels by perfusing the organ with a medical fluid, such as an oxygenated cross-linked hemoglobin-based bicarbonate medical fluid, at normothermic temperatures. In perfusion, organ perfusion pressure is preferably controlled in response to a sensor disposed in an end of tubing placed in the organ, by a pneumatically pressurized medical fluid reservoir, providing perfusion pressure fine tuning, overpressurization prevention and emergency flow cut-off. In the hypothermic mode, the organ is perfused with a medical fluid, preferably a simple crystalloid solution containing antioxidants, intermittently or in slow continuous flow. The medical fluid may be fed into the organ from an intermediary tank having a low pressure head to avoid organ overpressurization. Preventing overpressurization prevents or reduces damage to vascular endothelial lining and to organ tissue in general. Viability of the organ may be automatically monitored, preferably by monitoring characteristics of the medical fluid perfusate. The perfusion process can be automatically controlled using a control program.

10 Claims, 29 Drawing Sheets

| OPERATION | SPEED | MOTOR DRIVE WAVEFORM | PRESSURE WAVEFORM |
|---|---|---|---|
| ① D.C. | CONSTANT | ⚬------------- | ∿∿∿ |
| ② ACTIVE CONTINUOUS | SLOW | ∿∿ | ⚬------------- |
| ② ACTIVE CONTINUOUS | FAST | ∿∿∿∿ | ⚬------------- |
| ③ ACTIVE WAVEFORM AMPLITUDE MODULATING | SLOW | { ∿∿ / ⊓⊔⊓ } | ⊓⊔⊓ |
| ③ ACTIVE WAVEFORM AMPLITUDE MODULATING | FAST | { ∿∿∿ / ⊓⊔⊓⊔ } | ⊓⊔⊓ |
| ④ ACTIVE WAVEFORM PULSE WIDTH MODULATING | SLOW | { ∿∿ / ⊓⊔⊓ } | ⊓⊔ |
| ④ ACTIVE WAVEFORM PULSE WIDTH MODULATING | FAST | { ∿∿∿ / ⊓⊔⊓⊔ } | ⊓⊔ |

FIG. 25A

APPARATUS AND METHOD FOR MAINTAINING AND/OR RESTORING VIABILITY OF ORGANS

This is a Division of application Ser. No. 12/662,930, filed May 12, 2010, which is a Division of application Ser. No. 10/617,130 filed Jul. 11, 2003, now U.S. Pat. No. 7,824,848, which in turn is a Division of application Ser. No. 09/645,525 filed Aug. 25, 2000, now U.S. Pat. No. 6,673,594, which is a Continuation-in-part of application Ser. No. 09/537,180 filed Mar. 29, 2000, now U.S. Pat. No. 6,977,140, and a Continuation-in-part of application Ser. No. 09/162,128 filed Sep. 29, 1998, now abandoned. The disclosure of the prior applications is hereby incorporated by reference herein in their entirety.

BACKGROUND OF THE INVENTION

1. Field of Invention

The invention relates to an apparatus and method for perfusing one or more organs to monitor, sustain and/or restore the viability of the organ(s) and/or for transporting and/or storing the organ(s).

2. Description of Related Art

Preservation of organs by machine perfusion has been accomplished at hypothermic temperatures with or without computer control with crystalloid perfusates and without oxygenation. See, for example, U.S. Pat. Nos. 5,149,321, 5,395,314, 5,584,804, 5,709,654 and 5,752,929 and U.S. patent application Ser. No. 08/484,601 to Klatz et al., which are hereby incorporated by reference. Hypothermic temperatures provide a decrease in organ metabolism, lower the energy requirements, delay the depletion of high energy phosphate reserves and accumulation of lactic acid and retard the morphological and functional deterioration associated with disruption of blood supply. Oxygen can not be utilized efficiently by mitochondria below approximately 20° C. to produce energy, and the reduction in catalase/superoxide dismutase production and ascorbyl and glutathione regeneration at low temperatures allows high free radical formation. The removal of oxygen from perfusates during low temperature machine perfusion has proven helpful in improving organ transplant results by some investigators.

Reduction in potential oxygen damage is also accomplished via the addition of antioxidants to the perfusate. In particular, this has proven useful in reducing organ damage after long warm ischemia times. Numerous other perfusate additives have also been reported to improve the outcome of machine perfusion.

Ideally organs would be procured in a manner that limits their warm ischemia time to essentially zero. Unfortunately, in reality, many organs, especially from non-beating heart donors, are procured after extended warm ischemia time periods (i.e., 45 minutes or more). The machine perfusion of these organs at low temperature has demonstrated significant improvement (Transpl Int 1996 Daemen). Further, prior art teaches that the low temperature machine perfusion of organs is preferred at low pressures (Transpl. Int 1996 Yland) with roller or diaphragm pumps delivering the perfusate at a controlled pressure. Numerous control circuits and pumping configurations have been utilized to achieve this objective and to machine perfuse organs in general. See, for example, U.S. Pat. Nos. 5,338,662 and 5,494,822 to Sadri; U.S. Pat. No. 4,745,759 to Bauer et al.; U.S. Pat. Nos. 5,217,860 and 5,472,876 to Fahy et al.; U.S. Pat. No. 5,051,352 to Martindale et al.; U.S. Pat. No. 3,995,444 to Clark et al.; U.S. Pat. No. 4,629,686 to Gruenberg; U.S. Pat. Nos. 3,738,914 and 3,892,628 to Thorne et al.; U.S. Pat. Nos. 5,285,657 and 5,476,763 to Bacchi et al.; U.S. Pat. No. 5,157,930 to McGhee et al.; and U.S. Pat. No. 5,141,847 to Sugimachi et al. However, in some situations the use of such pumps for machine perfusion of organs may increase the risk of overpressurization of the organ should the organ perfusion apparatus malfunction. High pressure perfusion (e.g., above about 60 mm Hg) can wash off the vascular endothelial lining of the organ and in general damages organ tissue, in particular at hypothermic temperatures where the organ does not have the neurological or endocrinal connections to protect itself by dilating its vasculature under high pressure.

Furthermore, the techniques used for assessment of the viability of these machine perfused organs have been a critical factor in limiting the organs from greater use. While increased organ resistance (i.e., pressure/flow) measurements during machine perfusion are a useful indicator, they demonstrate only the worst case situations.

During low temperature machine perfusion of organs that have been damaged by warm ischemia time or by the machine perfusion itself, the organs will elute intracellular and endothelial as well as membrane constituents. Over the years the appearance of various ubiquitous intracellular enzymes, such as lactic dehydrogenase (LDH) and alkaline phosphatase, in the perfusate has been used as a biomarker of organ damage. Recently, the determination of the presence of alpha glutathione-S-transferase (a-GST) and Pi glutathione-S-transferase (p-GST) in low temperature machine perfusion perfusates has proven a satisfactory indicator in predicting the functional outcome of non-beating heart donor kidney grafts before transplantation (Transpl 1997 Daemen).

The prior art has also addressed the need to restore or maintain an organ's physiological function after preservation for an extended period of time at hypothermic temperatures. In particular, U.S. Pat. No. 5,066,578 to Wikman-Coffelt discloses an organ preservation solution that contains large amounts of pyruvate. Wikman-Coffelt teaches that flooding of the organ with pyruvate bypasses glycosis, the step in the cell energy cycle that utilizes adenosine triphosphate (ATP) to produce pyruvate, and pyruvate is then available to the mitochondria for oxidative phosphorylation producing ATP. Wikman-Coffelt teaches perfusing or washing an organ at a warm temperature with a first preservation solution containing pyruvate for removal of blood or other debris from the organ's vessels and to vasodilate, increase flow and load the cells with an energy supply in the form of a clean substrate, namely the pyruvate. Wikman-Coffelt teaches that the pyruvate prevents edema, ischemia, calcium overload and acidosis as well as helps preserve the action potential across the cell membrane. The organ is then perfused with a second perfusion solution containing pyruvate and a small percentage of ethanol in order to stop the organ from working, vasodilate the blood vessels allowing for full vascular flow, continue to load the cells with pyruvate and preserve the energy state of the organ. Finally the organ is stored in a large volume of the first solution for 24 hours or longer at temperatures between 4° C. and 10° C.

However, the mitochondria are the source of energy in cells and need significant amounts of oxygen to function. Organs naturally have significant pyruvate levels, and providing an organ with additional pyruvate will not assist in restoring and/or maintaining an organ's full physiological function if the mitochondria are not provided with sufficient oxygen to function. Further, briefly flooding an organ with pyruvate may, in fact, facilitate tearing off of the vascular endothelial lining of the organ.

U.S. Pat. No. 5,599,659 to Brasile et al. also discloses a preservation solution for warm preservation of tissues, explants, organs and endothelial cells. Brasile et al. teaches disadvantages of cold organ storage, and proposes warm preservation technology as an alternative. Brasile et al. teaches that the solution has an enhanced ability to serve as a medium for the culture of vascular endothelium of tissue, and as a solution for organs for transplantation using a warm preservation technology because it is supplemented with serum albumin as a source of protein and colloid; trace elements to potentiate viability and cellular function; pyruvate and adenosine for oxidative phosphorylation support; transferrin as an attachment factor; insulin and sugars for metabolic support and glutathione to scavenge toxic free radicals as well as a source of impermeant; cyclodextrin as a source of impermeant, scavenger, and potentiator of cell attachment and growth factors; a high Mg++ concentration for microvessel metabolism support; mucopolysaccharides, comprising primarily chondroitin sulfates and heparin sulfates, for growth factor potentiation and hemostasis; and ENDO GRO™ as a source of cooloid, impermeant and specific vascular growth promoters. Brasile et al. further teaches warm perfusing an organ for up to 12 hours at 30° C., or merely storing the organ at temperatures of 25° C. in the preservation solution.

However, flooding an organ with such chemicals is insufficient to arrest or repair ischemic injury where the mitochondria are not provided with sufficient oxygen to function to produce energy. The oxygen needs of an organ at more than 20° C. are substantial and cannot be met by a simple crystalloid at reasonable flows. Further, assessment of the viability of an organ is necessary before the use of any type of solution can be determined to have been fruitful.

WO 88/05261 to Owen discloses an organ perfusion system including an organ chamber that is supplied with an emulsion fluid or physiological electrolyte that is transported through a perfusion system. The chamber contains a synthetic sac to hold the organ. Perfusate enters the organ through a catheter inserted into an artery. The perfusate is provided by two independent fluid sources, each of which includes two reservoirs.

SUMMARY OF THE INVENTION

The present invention focuses on avoiding damage to an organ during perfusion while monitoring, sustaining and/or restoring the viability of the organ and preserving the organ for storage and/or transport. The invention is directed to an apparatus and method for perfusing an organ to monitor, sustain and/or restore the viability of the organ and/or for transporting and/or storing the organ. More particularly, the organ perfusion apparatus and method according to the invention monitor, sustain and/or restore organ viability by perfusing the organ at hypothermic temperature (hypothermic perfusion mode) and/or normothermic temperatures (normothermic perfusion mode) preferably after flushing of the organ such as by hypothermic flushing followed by static organ storage and/or organ perfusion at hypothermic temperatures for transport and/or storage of the organ.

The restoring of organ viability may be accomplished by restoring high energy nucleotide (e.g., adenosine triphosphate (ATP)) levels and enzyme levels in the organ, which were reduced by warm ischemia time and/or hypoxia, by perfusing the organ with an oxygenated medical fluid, such as an oxygenated cross-linked hemoglobin-based bicarbonate medical fluid, at normothermic or near-normothermic temperatures. The organ may be flushed with a medical fluid prior to perfusion with the oxygenated medical fluid. Such perfusion can be performed at either normothermic or hypothermic temperatures, preferably at hypothermic temperatures. For hypothermic flush, static storage and hypothermic perfusion, the medical fluid preferably contains little or no oxygen and preferably includes antioxidants, both molecular (e.g., 2-ascorbic acid tocopherol) and enzymatic (e.g., catalase and superoxide dismutase (SOD)). Normothermic and/or hypothermic perfusion, and preferably hypothermic perfusion, can be performed in vivo as well as in vitro. Such perfusion arrests ischemic injury in preparation for transport, storage and/or transplant of the organ.

The normothermic treatment is preferably employed after an organ has been subjected to hypothermic temperatures, statically and/or under perfusion. Such initial hypothermic exposure can occur, for example, during transport and/or storage of an organ after harvesting. The treatment is also suitable for organs that will ultimately be stored and/or transported under hypothermic conditions. In other words, the treatment can be applied to organs prior to cold storage and/or transport.

In the normothermic perfusion mode, gross organ perfusion pressure is preferably provided by a pneumatically pressurized medical fluid reservoir controlled in response to a sensor disposed in an end of tubing placed in the organ, which may be used in combination with a stepping motor/cam valve or pinch valve which provides for perfusion pressure fine tuning, prevents overpressurization and/or provides emergency flow cut-off. Alternatively, the organ may be perfused directly from a pump, such as a roller pump or a peristaltic pump, with proper pump control and/or sufficiently fail-safe controllers to prevent overpressurization of the organ, especially as a result of a system malfunction. Substantially eliminating overpressurization prevents and/or reduces damage to the vascular endothelial lining and to the organ tissue in general. Viability of the organ may be monitored, preferably automatically, in the normothermic perfusion mode, preferably by monitoring organ resistance (pressure/flow) and/or pH, $pO_2$, $pCO_2$, LDH, T/GST, Tprotein, lactate, glucose, base excess and/or ionized calcium levels in the medical fluid that has been perfused through the organ and collected.

An organ viability index may be provided taking into account the various measured factors identified above, such as vascular resistance, pH etc. The index may be organ specific, or may be adaptable to various organs. The index compiles the monitored parameters into a diagnostic summary to be used for making organ therapy decisions and deciding whether to transplant the organ. The index may be automatically generated and provided to the physician.

Normothermic perfusion may be preceded by and/or followed by hypothermic perfusion. In the hypothermic mode, the organ is perfused with a medical fluid containing substantially no oxygen, preferably a simple crystalloid solution that may preferably be augmented with antioxidants, intermittently or at a slow continuous flow rate. Hypothermic perfusion also can be performed in vivo as well as in vitro prior to removal of the organ from the donor. Hypothermic perfusion reduces the organ's metabolic rate, allowing the organ to be preserved for extended periods of time. The medical fluid is preferably fed into the organ by pressure from an intermediary tank which has a low pressure head so overpressurization of the organ is avoided. Alternatively, in embodiments, gravity can be used to feed the medical fluid into the organ from the intermediary tank, if appropriate. Alternatively, the organ may be perfused directly from a pump, such as a roller pump or a peristaltic pump, with proper pump control and/or sufficiently fail-safe controllers to prevent overpressurization of the organ, especially as a result of a system malfunction.

Substantially eliminating overpressurization prevents or reduces damage to the vascular endothelial lining of the organ and to the organ tissue in general, in particular at hypothermic temperatures when the organ has less ability to protect itself by vascular constriction. Viability of the organ may also be monitored, preferably automatically, during the recovery process, preferably by monitoring organ resistance (pressure/flow) and/or pH, $pO_2$, $pCO_2$, LDH, T/GST, Tprotein, lactate, glucose, base excess and/or ionized calcium levels in the medical fluid that has been perfused through the organ and collected.

Embodiments of this invention include a control system for automatically controlling perfusion of one or more organs by selecting between perfusion modes and control parameters. Automatic perfusion may be based on sensed conditions in the system or manually input parameters. The system may be preprogrammed or programmed during use. Default values and viability checks are utilized.

The perfusion apparatus may be used for various organs, such as the kidneys, and may be adapted to more complex organs, such as the liver, having multiple vasculature structures, for example, the hepatic and portal vasculatures of the liver.

An organ diagnostic apparatus may also be provided to produce diagnostic data such as an organ viability index. The organ diagnostic apparatus includes features of an organ perfusion apparatus, such as sensors and temperature controllers, as well as cassette interface features, and provides analysis of input and output fluids in a perfusion system. Typically, the organ diagnostic apparatus is a simplified perfusion apparatus providing diagnostic data in a single pass, in-line perfusion.

The present invention also provides an organ cassette which allows an organ to be easily and safely moved between apparatus for perfusing, storing, analyzing and/or transporting the organ. The organ cassette may be configured to provide uninterrupted sterile conditions and efficient heat transfer during transport, recovery, analysis and storage, including transition between the transporter, the perfusion apparatus and the organ diagnostic apparatus.

The present invention also provides an organ transporter which allows for transportation of an organ over long distances. The organ transporter may be used for various organs, such as the kidneys, and may be adapted to more complex organs, such as the liver, having multiple vasculature structures, for example, the hepatic and portal vasculatures of the liver. The organ transporter includes features of an organ perfusion apparatus, such as sensors and temperature controllers, as well as cassette interface features.

The perfusion apparatus, transporter, cassette, and organ diagnostic apparatus may be networked to permit remote management, tracking and monitoring of the location and therapeutic and diagnostic parameters of the organ or organs being stored or transported. The information systems may be used to compile historical data of organ transport and storage, and provide cross-referencing with hospital and United Network for Organ Sharing (UNOS) data on the donor and recipient. The systems may also provide outcome data to allow for ready research of perfusion parameters and transplant outcomes.

BRIEF DESCRIPTION OF THE DRAWINGS

These and other aspects and advantages of the invention will become apparent from the following detailed description of embodiments when taken in conjunction with the accompanying drawings, in which:

FIGS. 25 and 25A show motor control of a perfusion pump according to the present invention;

DETAILED DESCRIPTION OF PREFERRED EMBODIMENTS

Figure 1:
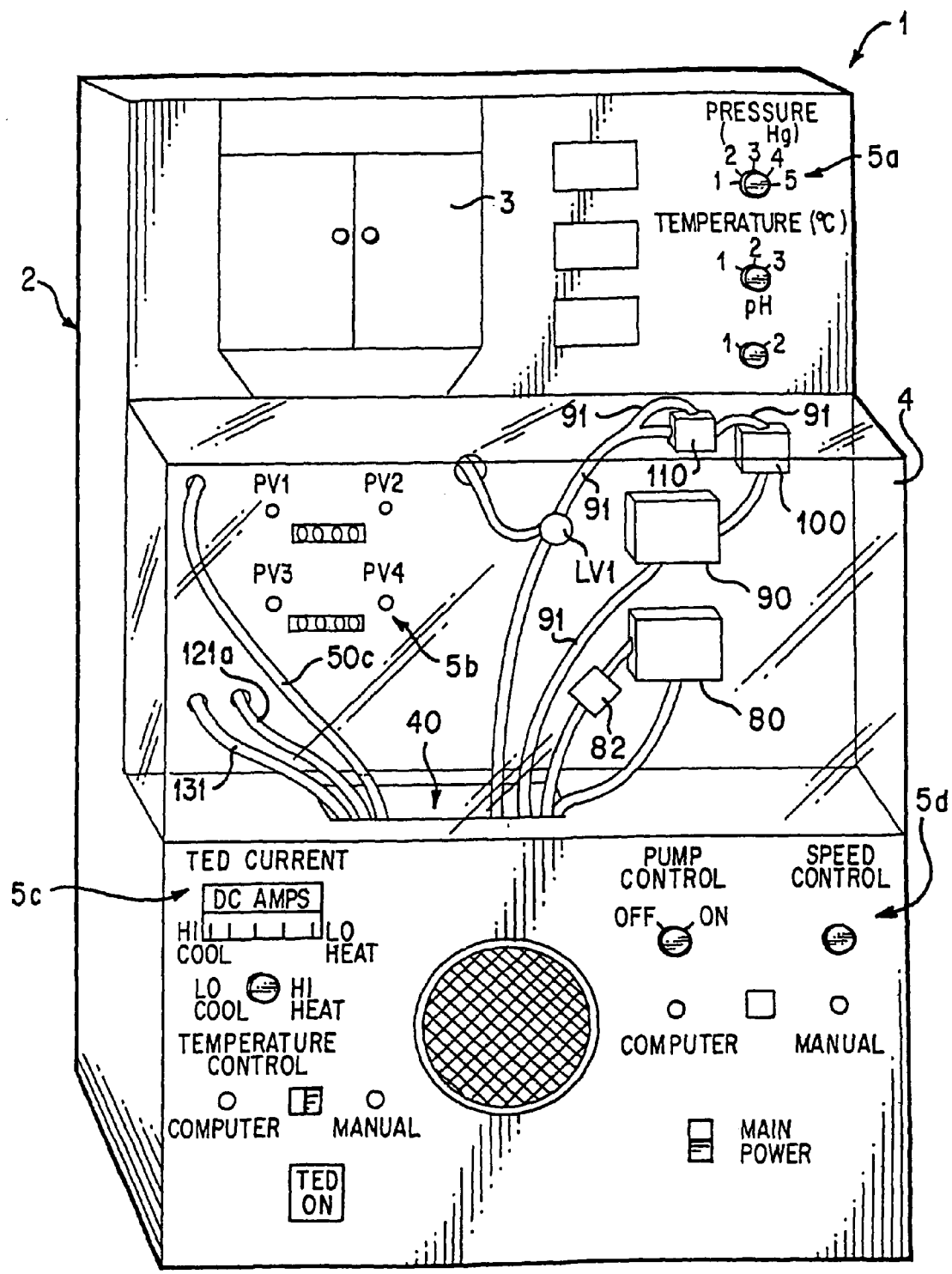
FIG. 1 is an organ perfusion apparatus according to the invention.

For a general understanding of the features of the invention, reference is made to the drawings. In the drawings, like reference numerals have been used throughout to designate like elements.

Figure 2:
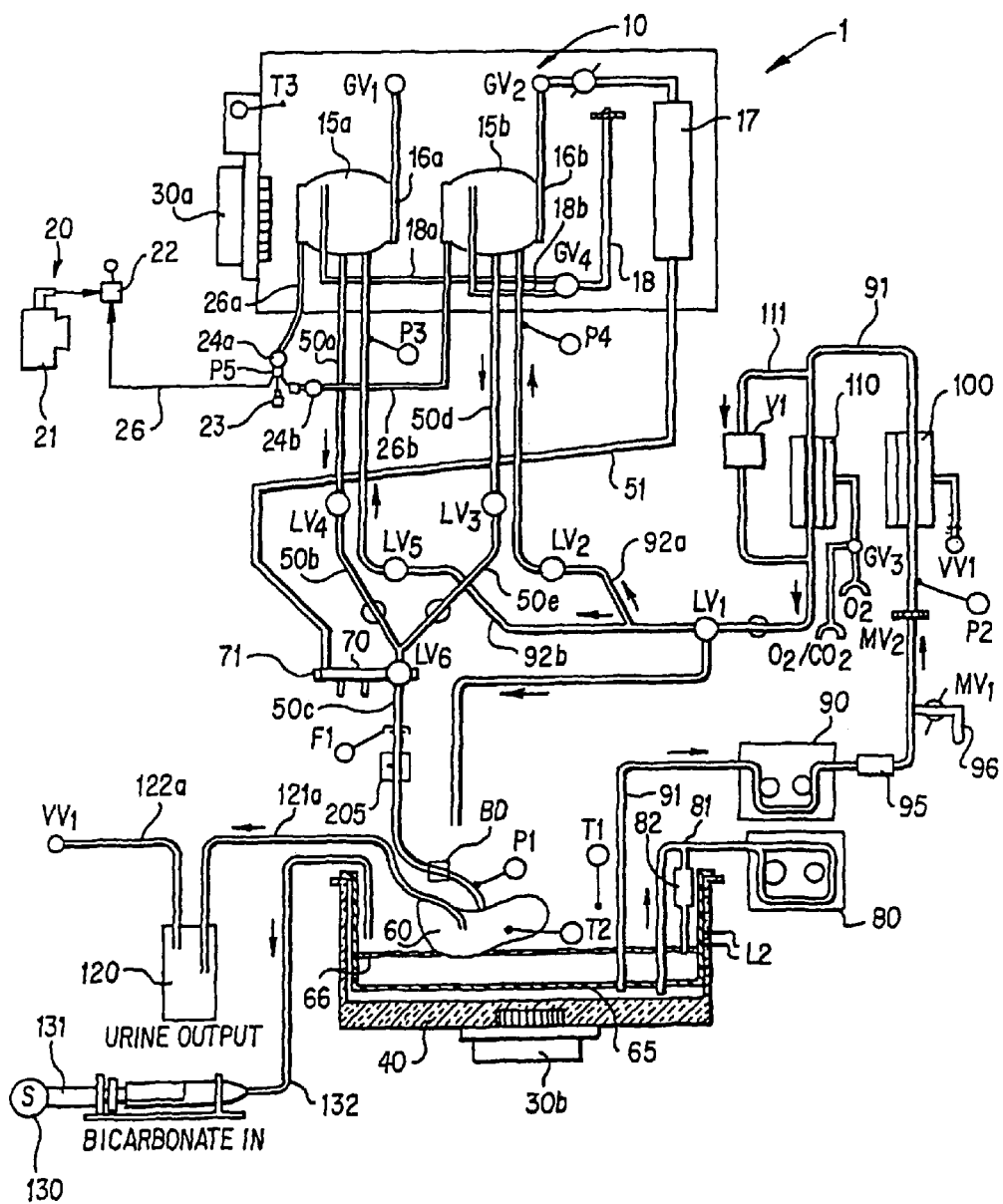
FIG. 2 is a schematic diagram of the apparatus of FIG. 1.
Figure 3:
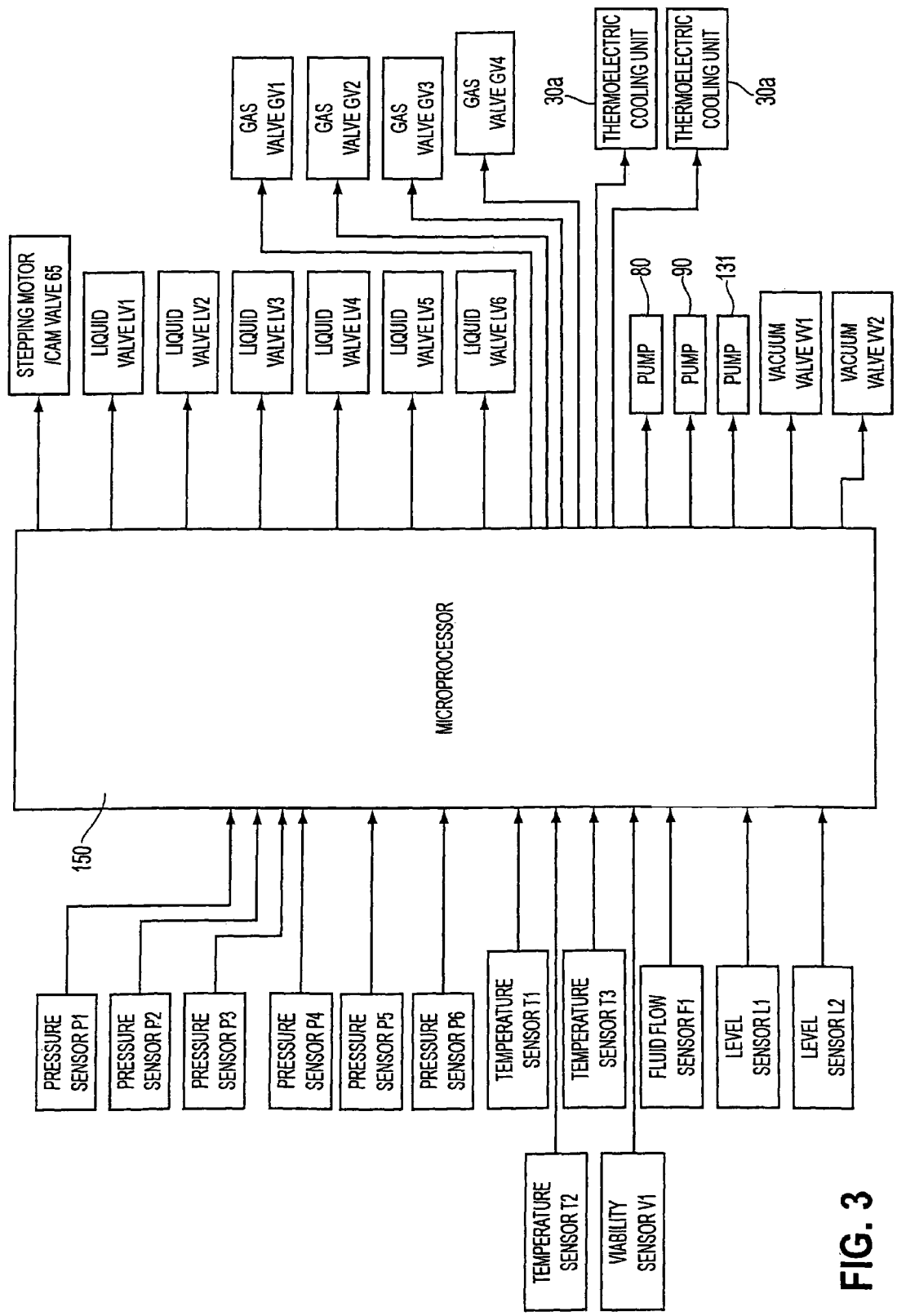
FIG. 3 is a diagram of the electronics of the apparatus of FIG. 1.

FIG. 1 shows an organ perfusion apparatus 1 according to the invention. FIG. 2 is a schematic illustration of the apparatus of FIG. 1. The apparatus 1 is preferably at least partially microprocessor controlled, and pneumatically actuated. The microprocessor 150 connection to the sensors, valves, thermoelectric units and pumps of the apparatus 1 is schematically shown in FIG. 3. Microprocessor 150 and apparatus 1 may be configured to and are preferably capable of further being connected to a computer network to provide data sharing, for example across a local area network or across the Internet.

The organ perfusion apparatus 1 is capable of perfusing one or more organs simultaneously, at both normothermic and hypothermic temperatures (hereinafter, normothermic and hypothermic perfusion modes). All medical fluid contact surfaces are preferably formed of or coated with materials compatible with the medical fluid used, more preferably non-thrombogenic materials. As shown in FIG. 1, the apparatus 1 includes a housing 2 which includes front cover 4, which is preferably translucent, and a reservoir access door 3. The apparatus preferably has one or more control and display areas 5a, 5b, 5c, 5d for monitoring and controlling perfusion.

As schematically shown in FIG. 2, enclosed within the housing 2 is a reservoir 10 which preferably includes three reservoir tanks 15a, 15b, 17. Two of the reservoir tanks 15a, 15b are preferably standard one liter infusion bags, each with a respective pressure cuff 16a, 16b. A pressure source 20 can be provided for pressurizing the pressure cuffs 16a, 16b. The pressure source 20 is preferably pneumatic and may be an on board compressor unit 21 supplying at least 10 LPM external cuff activation via gas tubes 26, 26a, 26b, as shown in FIG. 2. The invention, however, is not limited to use of an on board compressor unit as any adequate pressure source can be employed, for example, a compressed gas (e.g., air, $CO_2$, oxygen, nitrogen, etc.) tank (not shown) preferably with a tank volume of 1.5 liters at 100 psi or greater for internal pressurization. Alternatively, an internally pressurized reservoir tank (not shown) may be used. Reservoir tanks 15a, 15b, 17 may, in embodiments, be bottles or other suitably rigid reservoirs that can supply perfusate by gravity or can be pressurized by compressed gas.

Gas valves 22-23 are provided on the gas tube 26 to allow for control of the pressure provided by the onboard compressor unit 21. Anti-back flow valves 24a, 24b may be provided respectively on the gas tubes 26a, 26b. Pressure sensors P5, P6 may be provided respectively on the gas tubes 26a, 26b to relay conditions therein to the microprocessor 150, shown in FIG. 3. Perfusion, diagnostic and/or transporter apparatus may be provided with sensors to monitor perfusion fluid pressure and flow in the particular apparatus to detect faults in the particular apparatus, such as pressure elevated above a suitable level for maintenance of the organ. Gas valves $GV_1$ and $GV_2$ may be provided to release pressure from the cuffs 16a, 16b. One or both of gas valves $GV_1$ and $GV_2$ may be vented to the atmosphere. Gas valve $GV_4$ in communication with reservoir tanks 15a, 15b via tubing 18a, 18b may be provided to vent air from the reservoir tanks 15a, 15b through tubing 18. Tubing 18, 18a, 18b, 26, 26a and/or 26b may be configured with filters and/or check valves to prevent biological materials from entering the tubing or from proceeding further along the fluid path. The check valves and/or filters may be used to prevent biological materials from leaving one organ perfusion tubeset and being transferred to the tubeset of a subsequent organ in a multiple organ perfusion configuration. The check valves and/or filters may also be used to prevent biological materials, such as bacteria and viruses, from being transferred from organ to organ in subsequent uses of the perfusion apparatus in the event that such biological materials remain in the perfusion apparatus after use. The check valves and/or filters prevent contamination problems associated with reflux in the gas and/or vent lines. For example, the valves may be configured as anti-reflux valves to prevent reflux. The third reservoir tank 17 is preferably pressurized by pressure released from one of the pressure cuffs via gas valve $GV_2$.

The medical fluid is preferably synthetic and may, for example, be a simple crystalloid solution, or may be augmented with an appropriate oxygen carrier. The oxygen carrier may, for example, be washed, stabilized red blood cells, cross-linked hemoglobin, pegolated hemoglobin or fluorocarbon based emulsions. The medical fluid may also contain antioxidants known to reduce peroxidation or free radical damage in the physiological environment and specific agents known to aid in tissue protection. As discussed in detail below, an oxygenated (e.g., cross-linked hemoglobin-based bicarbonate) solution is preferred for the normothermic mode while a non-oxygenated (e.g., simple crystalloid solution preferably augmented with antioxidants) solution is preferred for the hypothermic mode. The specific medical fluids used in both the normothermic and hypothermic modes are designed to reduce or prevent the washing away of or damage to the vascular endothelial lining of the organ. For the hypothermic perfusion mode, as well as for flush and/or static storage, a preferred solution is the solution disclosed in U.S. patent application Ser. No. 09/628,311, filed Jul. 28, 2000, the entire disclosure of which is incorporated herein by reference. Examples of additives which may be used in perfusion solutions for the present invention are also disclosed in U.S. Pat. No. 6,046,046 to Hassanein, the entire disclosure of which is incorporated by reference. Of course, other suitable solutions and materials may be used, as is known in the art.

The perfusion solution may be provided in a perfusion solution kit, for example, a saleable package preferably containing at least one first container holding a first perfusion solution for normothermic perfusion and at least one second container holding a second, different perfusion solution for hypothermic perfusion, optionally the box 10 shown in FIG. 2. The first perfusion solution may contain at least one oxygen carrier, may be oxygenated and/or may be selected from the group consisting of a cross-linked hemoglobin and stabilized red blood cells. The second perfusion solution may be non-oxygenated, may contain at least one anti-oxidant, and/or may contain at least one vasodilator. Additionally, the solution preferably contains no more than 5 mM of dissolved pyruvate salt. Also, the first container and the second container may be configured to be operably connected to a perfusion machine as perfusion fluid reservoirs in fluid communication with perfusate conduits of said perfusion machine. Further, one of the first and second containers may be compressible to apply pressure to the perfusion solution therein. Furthermore, at least one of the first and second containers may include a first opening for passage of a contained perfusion solution out of the container and a second opening passage of a compressed gas into the container. The package may be a cassette configured to be operably connected to a perfusion machine for connection of the first and second containers within the cassette in fluid communication with perfusate conduits or tubing of the perfusion machine.

In other embodiments, the perfusion solution kit may contain at least one first container holding a first perfusion solution for hypothermic perfusion at a first temperature and at least one second container holding a second, different perfusion solution for hypothermic perfusion at a second temperature lower than the first temperature. In the kit, the first perfusion solution may contain at least a crystalloid and may contain at least one vasodilator. The second perfusion solution may be oxygen carrier enhanced, where the oxygen carrier is selected from the group consisting of a hemoglobin and stabilized red blood cells. In addition, the second perfusion solution may, if desired, contain at least one anti-oxidant or free radical scavenger. Preferably, the second solution contains no more than 5 mM of dissolved pyruvate salt. As above, the first container and the second container may be configured to be operably connected to a perfusion machine as perfusion fluid reservoirs in fluid communication with perfusate conduits of said perfusion machine. Further, one of the first and second containers may be compressible to apply pressure to the perfusion solution therein. Furthermore, at least one of the first and second containers may include a first opening for passage of a contained perfusion solution out of the container and a second opening passage of a compressed gas into the container. The package may be a cassette configured to be operably connected to a perfusion machine for connection of the first and second containers within the cassette in fluid communication with perfusate conduits or tubing of the perfusion machine.

The medical fluid within reservoir 10 is preferably brought to a predetermined temperature by a first thermoelectric unit 30a in heat transfer communication with the reservoir 10. A temperature sensor T3 relays the temperature within the reservoir 10 to the microprocessor 150, which adjusts the thermoelectric unit 30a to maintain a desired temperature within the reservoir 10 and/or displays the temperature on a control and display areas 5a for manual adjustment. Alternatively or in addition, and preferably where the organ perfusion device is going to be transported, the medical fluid within the hypothermic perfusion fluid reservoir can be cooled utilizing a cryogenic fluid heat exchanger apparatus such as that disclosed in co-pending application Ser. No. 09/039,443, which is hereby incorporated by reference.

Figure 11A:
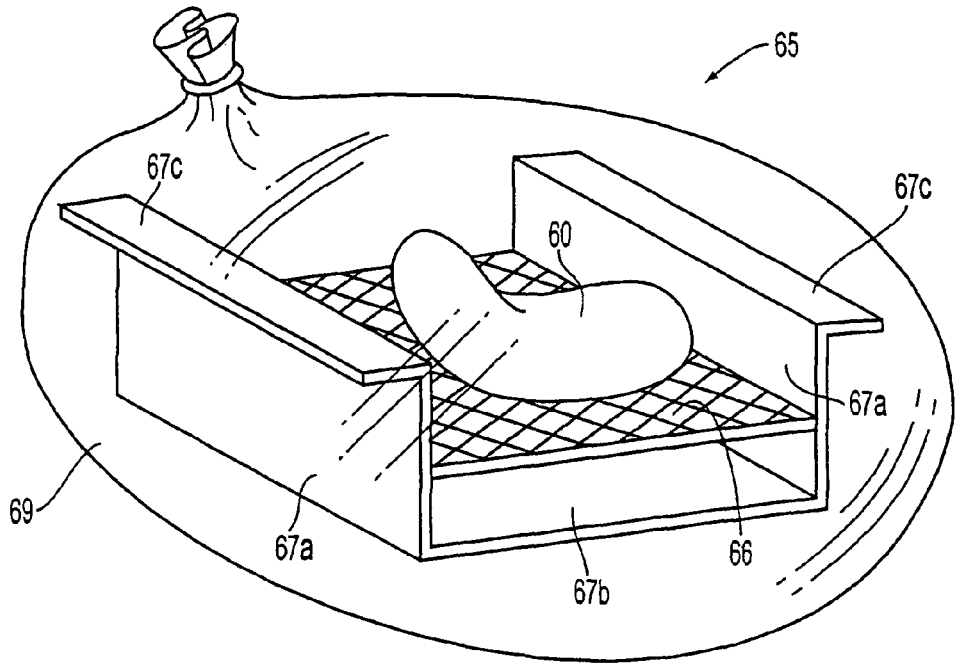
FIGS. 11A-11D show side perspective views of various embodiments of an organ cassette according to the invention.
Figure 11B:
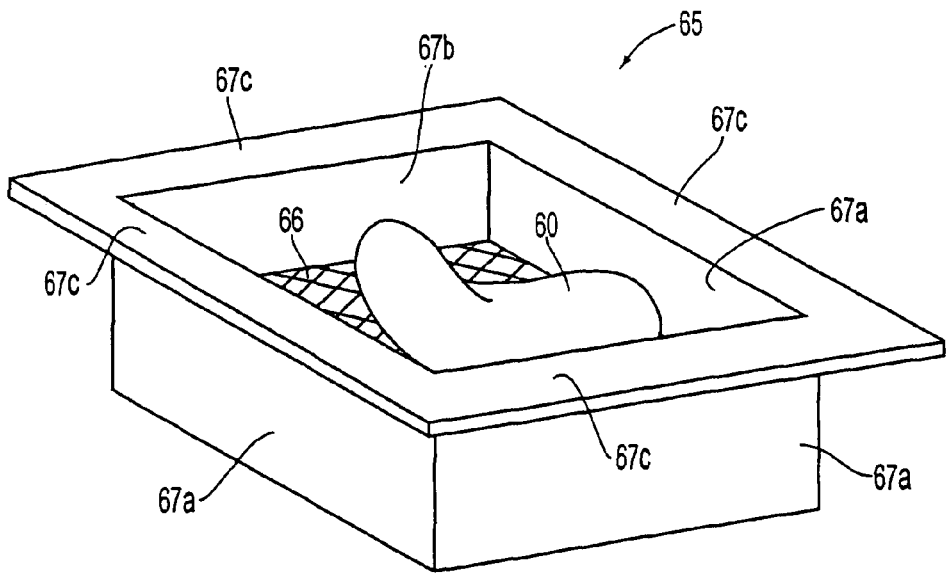
Figure 11D:
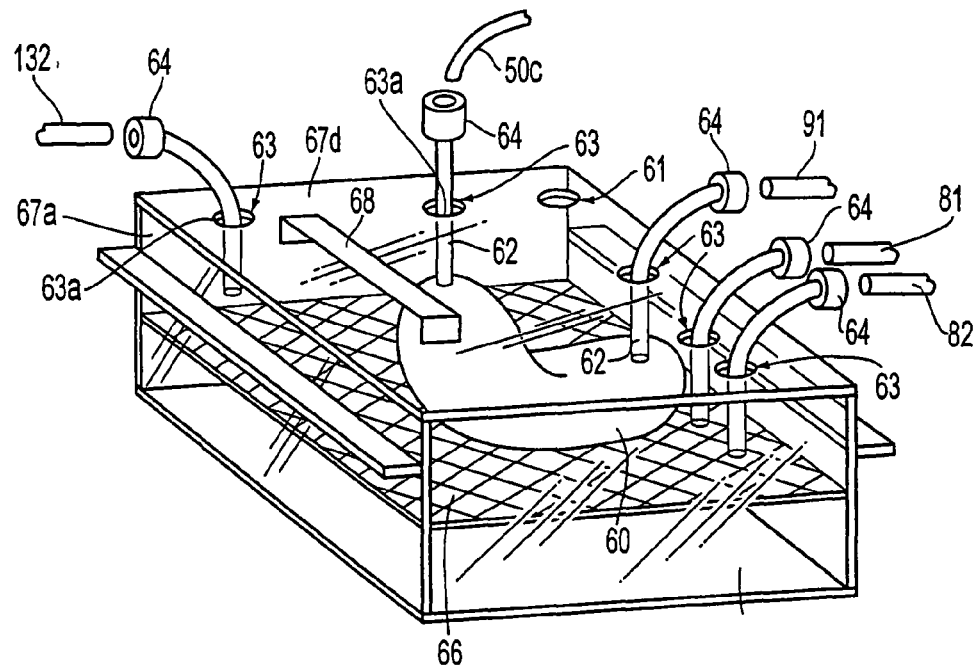
Figure 11C:
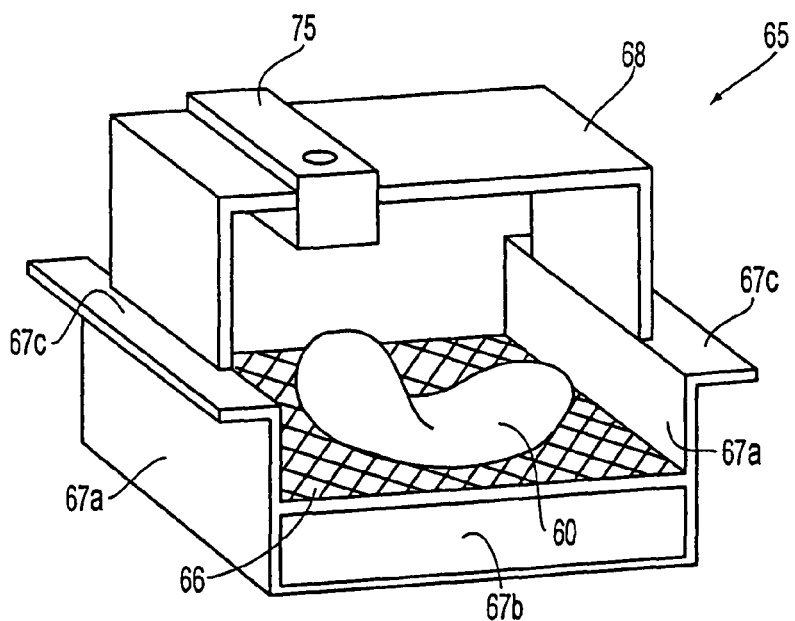
Figure 12:
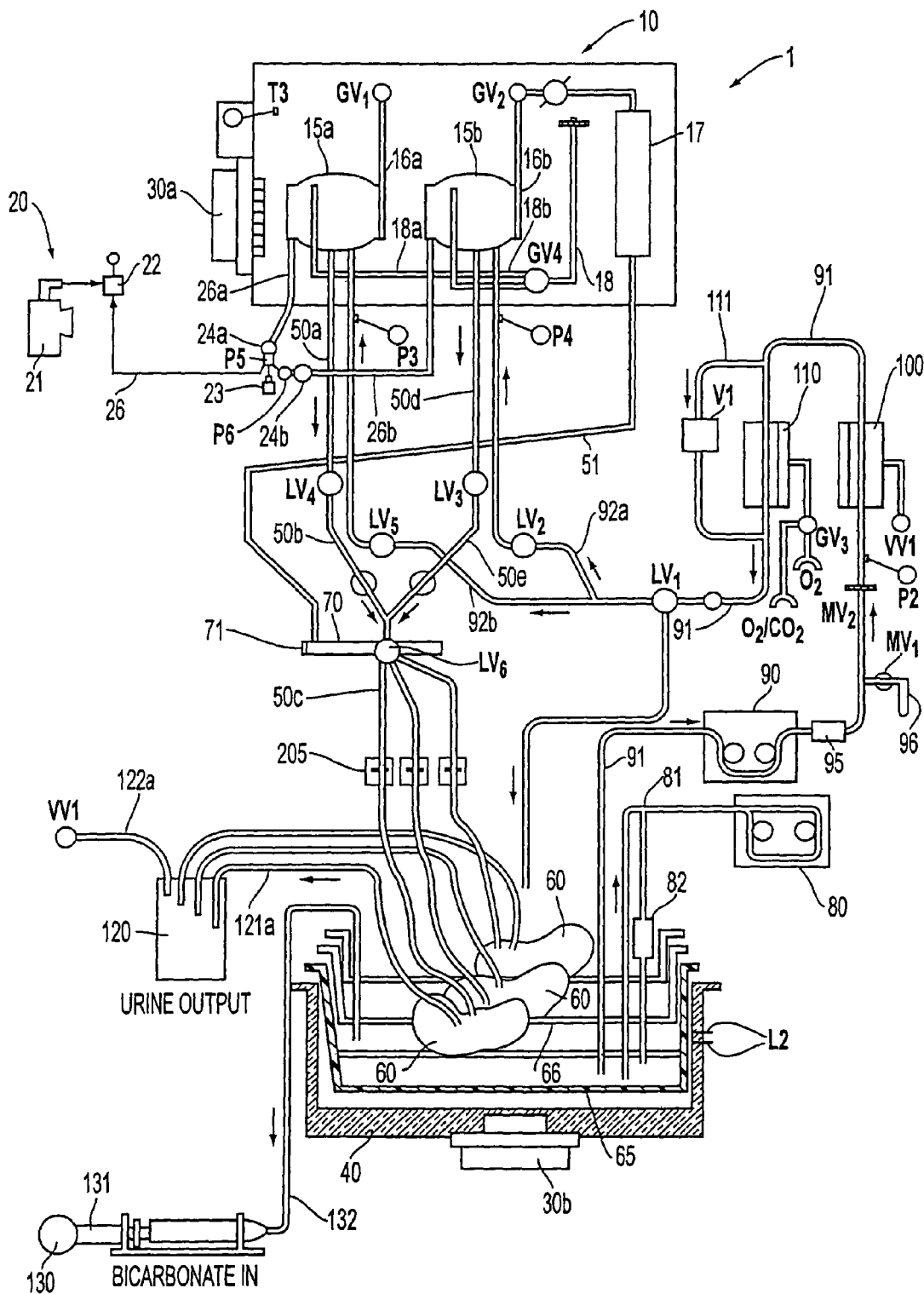
FIG. 12 is a schematic diagram of an organ perfusion apparatus configured to simultaneously perfuse multiple organs.

An organ chamber 40 is provided which supports a cassette 65, as shown in FIG. 2, which holds an organ to be perfused, or a plurality of cassettes 65, 65, 65, as shown in FIG. 12, preferably disposed one adjacent the other. Various embodiments of the cassette 65 are shown in FIGS. 11A-11D. The cassette 65 is preferably formed of a material that is light but durable so that the cassette 65 is highly portable. The material may also be transparent to allow visual inspection of the organ.

Preferably the cassette 65 includes side walls 67a, a bottom wall 67b and an organ supporting surface 66, which is preferably formed of a porous or mesh material to allow fluids to pass therethrough. The cassette 65 may also include a top 67d and may be provided with an opening(s) 63 for tubing (see, for example, FIG. 11D). The opening(s) 63 may include seals 63a (e.g., septum seals or o-ring seals) and optionally be provided with plugs (not shown) to prevent contamination of the organ and maintain a sterile environment. Also, the cassette 65 may be provided with a closeable air vent 61 (see, for example, FIG. 11D). Additionally, the cassette 65 may be provided with tubing for connection to the organ or to remove medical fluid from the organ bath and a connection device(s) 64 for connecting the tubing to, for example, tubing 50c, 81, 82, 91 and/or 132 (see, for example, FIG. 11D). The cassette 65, and more particularly the organ support, opening(s), tubing(s) and/or connection(s), may be specifically tailored to the type of organ and/or size of organ to be perfused. Outer edges 67c of the side support walls 67a can be used to support the cassette 65 disposed in the organ chamber 40. The cassette 65 may further include a handle portion 68 which allows the cassette 65 to be easily handled, as shown, for example, in FIGS. 11C and 11D. Each cassette 65 may also be provided with its own stepping motor/cam valve 75 (for example, in the handle portion 68, as shown in FIG. 11C) for fine tuning the pressure of medical fluid perfused into the organ 60 disposed therein, discussed in more detail below. Alternatively, pressure may, in embodiments, be controlled by way of a pneumatic chamber, such as an individual pneumatic chamber for each organ (not shown), or by any suitable variable valve such as a rotary screw valve or a helical screw valve.

Figure 17:
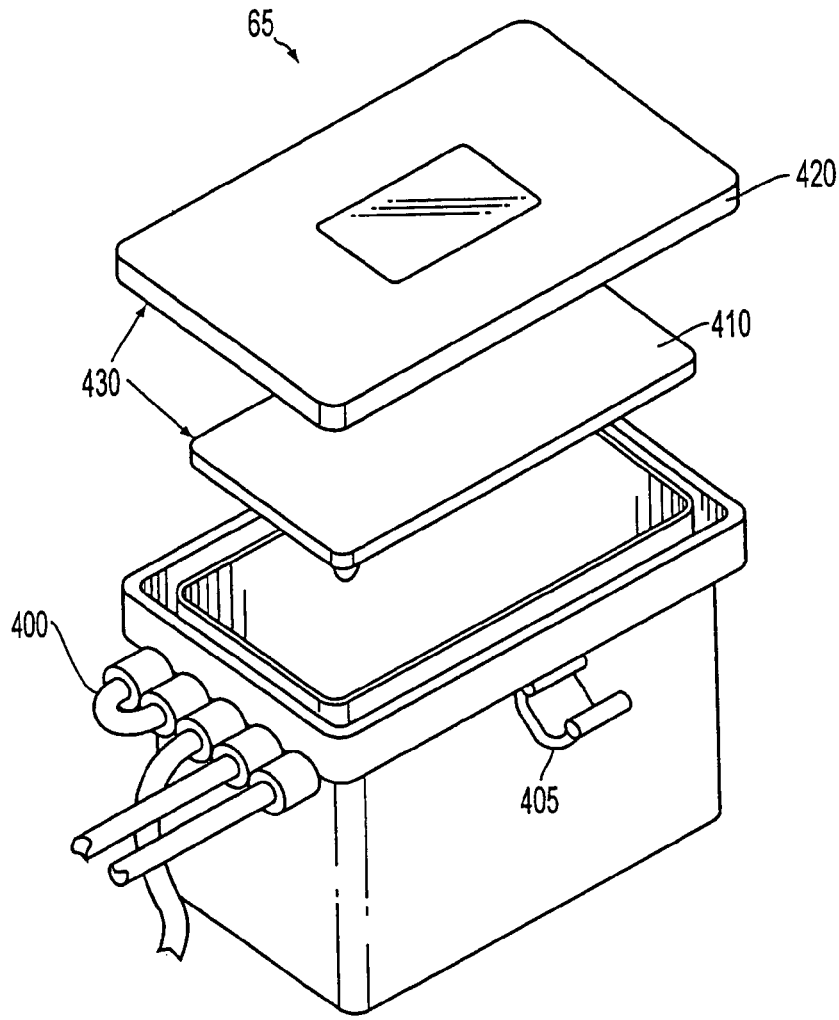
FIGS. 17 and 17A show an embodiment of an organ cassette of the present invention.
Figure 17A:
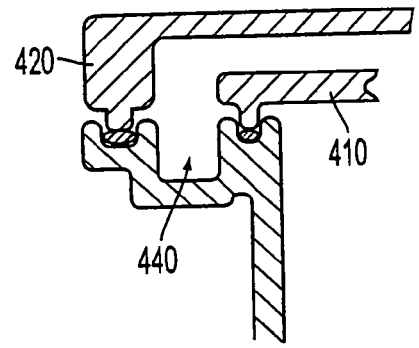

FIG. 17 shows an alternative embodiment of cassette 65. In FIG. 17, cassette 65 is shown with tubeset 400. Tubeset 400 can be connected to perfusion apparatus 1 or to an organ transporter or an organ diagnostic apparatus, and allows cassette 65 to be moved between various apparatus without jeopardizing the sterility of the interior of cassette 65. Preferably, cassette 65 is made of a sufficiently durable material that it can withstand penetration and harsh impact. Cassette 65 is provided with a lid, preferably two lids, an inner lid 410 and an outer lid 420. The lids 410 and 420 may be removable or may be hinged or otherwise connected to the body of cassette 65. Clasp 405 provides a mechanism to secure lids 410 and 420 to the top of cassette 65. Clasp 405 may additionally be configured with a lock to provide further security and stability. A biopsy port 430 may additionally be included in inner lid 410 or both inner lid 410 and outer lid 420. Biopsy port 430 provides access to the organ to allow for additional diagnosis of the organ with minimal disturbance of the organ. Cassette 65 may also have an overflow trough 440 (shown in FIG. 17A). Overflow trough 440 is a channel present in the top of cassette 65. When lids 410 and 420 are secured on cassette 65, overflow trough 440 provides a region that is easy to check to determine if the inner seal is leaking. Perfusate may be poured into and out of cassette 65 and may be drained from cassette 65 through a stopcock or removable plug.

Cassette 65 and/or both lids 410 and 420 may be constructed of an optically clear material to allow for viewing of the interior of cassette 65 and monitoring of the organ and to allow for video images or photographs to be taken of the organ. Perfusion apparatus 1 or cassette 65 may be wired and fitted with a video camera or a photographic camera, digital or otherwise, to record the progress and status of the organ. The captured images may be made available over a computer network such as a local area network or the Internet to provide for additional data analysis and remote monitoring. Cassette 65 may also be provided with a tag that would signal, e.g., through a bar code, magnetism, radio frequency, or other means, the location of the cassette, that the cassette is in the apparatus, and/or the identity of the organ to the perfusion apparatus or transporter. Cassette 65 may be sterile packaged and/or may be packaged or sold as a single-use disposable cassette, such as in a peel-open pouch. A single-use package containing cassette 65 may also include tubeset 400.

Figure 18:
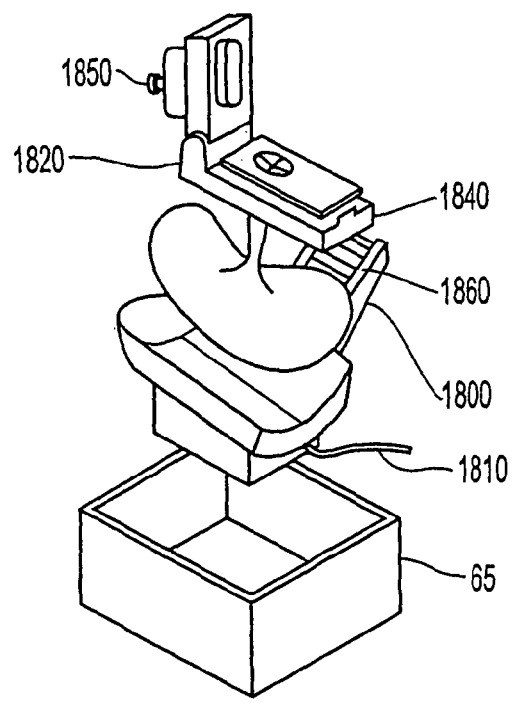
FIGS. 18 and 18A show an embodiment of an organ chair according to the present invention.
Figure 18A:
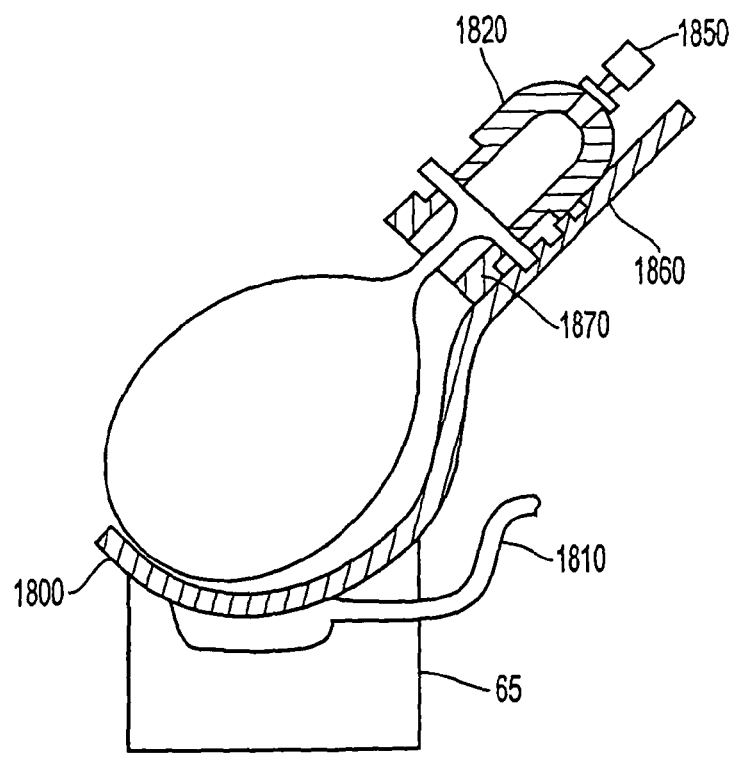

Cassette 65 may additionally be provided with an organ chair 1800 shown in FIGS. 18 and 18A. Organ chair 1800 is removable and provides a support surface for the organ within cassette 65. Utilizing a removable organ chair 1800 allows the organ to be cannulated and secured under cold conditions when the organ is recovered from a donor before being placed into cassette 65. Organ chair 1800 may be reusable or single-use. Organ chair 1800 may be constructed specifically to correspond to each type of organ, such as the kidney, heart or liver. Organ chair 1800 is preferably designed to be form fitting to the organ but to allow for the full anthropometric range of organ sizes.

Preferably, organ chair 1800 is at least partially perforated to allow fluids to pass through organ chair 1800. The perforations in organ chair 1800 may be sized to catch organ debris, or an additional filter layer, preferably constructed of cloth, fabric, nylon, plastic, etc., to catch organ debris of at least 15 microns in diameter. In addition, a separate filter may be used on the tubing that intakes fluid directly from the perfusate bath to prevent organ debris of a predetermined size, for example at least 10 to 15 microns in diameter, from entering the perfusion tubing.

Organ chair 1800 may also be configured with a venous outflow sampler 1810. Organ chair 1800 funnels the venous outflow into venous outflow sampler 1810. Venous outflow sampler 1810 provides a readily available source for capturing the venous outflow of the organ. Capturing the venous outflow in this manner permits analysis of the perfusate leaving the organ without cannulating a vein and enables organ viability to be measured with a high degree of sensitivity by analyzing differentially the perfusate flowing into and out of the organ. Alternatively, venous outflow may be captured directly by cannulating a vein, but this method increases the risk of damaging the vein or the organ. Organ chair 1800 may also be raised and lowered within cassette 65 to facilitate sampling from venous outflow sampler 1810. Alternatively, a sufficient amount of the organ bath may be drained from cassette 65 to obtain access to venous outflow sampler 1810 or to capture venous outflow before the outflow mixes with the rest of the perfusate in the organ bath.

Organ chair 1800 is preferably additionally configured with a cannula 1820 that attaches to the perfused artery, such as the renal artery. Cannula 1820 may be reusable or may be suitable for single-use, preferably provided in a sterile package with cassette 65, organ chair 1800 and tubeset 400. Cannula 1820 is provided with a cannula clamp 1830 to secure cannula 1820 around the perfused artery and to preferably provide leak-tight perfusion. A straight-in flanged cannula may also be used, however clamping around the artery is preferable to prevent contact with the inner surface of the artery, which is easily damaged. Cannula 1820 may also be configured with additional branching connections for accessory arteries. Multiple cannula and cannula clamp sizes may be used to accommodate various artery sizes or an adjustable cannula and cannula clamp may be used to accommodate various sized arteries. Cannula clamp 1830 may be a clamshell configuration or may be a two-part design. Cannula clamp 1830 may be configured with integral or separate means for tightening cannula clamp 1830 to the proper pressure to provide leak-tight perfusion. In addition, cannula 1820 may be provided with a snap 1840 to hold cannula 1820 closed. Cannula 1820 may also be provided with a vent 1850 to remove air bubbles from cannula 1820.

Organ chair 1800 preferably has a detented region 1860 that corresponds to protrusions 1870 on cannula 1820. Such detents, tracks or grooves on organ chair 1800 allow cannula 1820 to be positioned at several locations to provide various tensions on the perfused artery. This allows the ideal minimum tension to be set for each artery. Cannula clamp 1830 secures the perfusate tubing to the perfused artery. Cannula 1820 is adjustably secured to organ chair 1800 to provide for positioning the perfused artery to accommodate variations in organ size and artery length to prevent stretching, twisting, sagging or kinking of the artery. The combination of organ chair 1800, cannula 1820 and additional straps or wide belts provides a secure platform to transport the organ and to transfer the organ between the cassette and the surgical field.

Organ chair 1800, cannula 1820 and/or cannula clamp 1830 may be constructed of an optically clear material to facilitate monitoring of the organ and perfusion status.

The cassette 65 is configured such that it may be removed from the organ perfusion apparatus 1 and transported to another organ perfusion apparatus in a portable transporter apparatus, such as, for example, a conventional cooler or a portable container such as that disclosed in simultaneously filed co-pending U.S. application Ser. No. 09/161,919, or U.S. Pat. No. 5,586,438 to Fahy, which are hereby incorporated by reference in their entirety.

In embodiments, when transported, the organ is disposed on the organ supporting surface 66 and the cassette 65 is preferably enclosed in a preferably sterile bag 69, as shown, for example, in FIG. 11A. When the organ is perfused with medical fluid, effluent medical fluid collects in the bag 69 to form an organ bath. Alternatively, the cassette 65 can be formed with a fluid tight lower portion in which the effluent medical fluid may collect, or the effluent medical fluid may collect in the organ chamber 40 to form the organ bath. In either alternative case, the bag 69 would preferably be removed prior to inserting the cassette into the organ chamber 40. Further, where a plurality of organs are to be perfused, an organ chamber may be provided for each organ. Alternatively, cassette 65 can be transported in the dual-lid cassette of FIG. 17 and additionally carried within a portable organ transporter.

Figure 19:
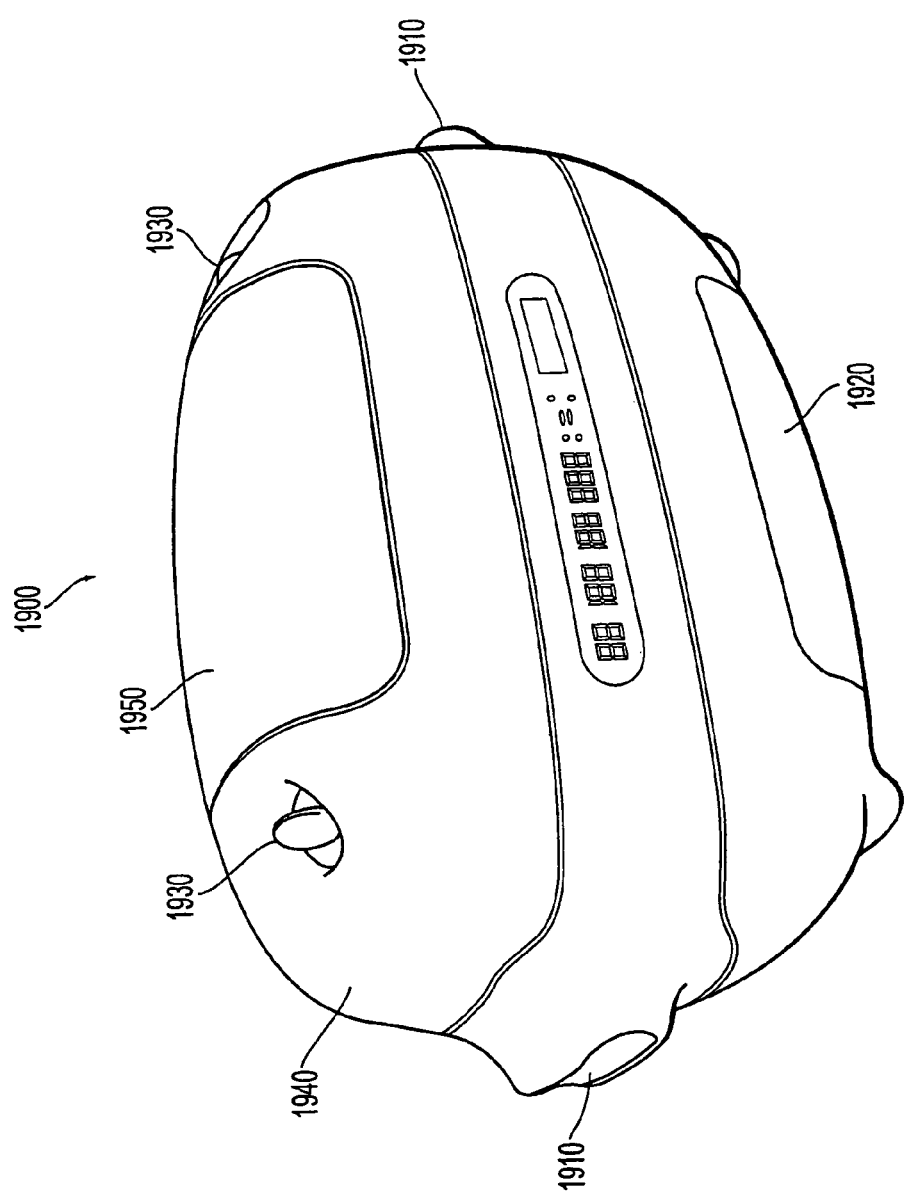
FIG. 19 shows an exterior perspective view of an organ transporter according to the present invention.

FIG. 19 shows an external view of an embodiment of transporter 1900 of the invention. The transporter 1900 of FIG. 19 has a stable base to facilitate an upright position and handles 1910 for carrying transporter 1900. Transporter 1900 may also be fitted with a shoulder strap and/or wheels to assist in carrying transporter 1900. A control panel 1920 is preferably also provided. Control panel 1920 may display characteristics, such as, but not limited to infusion pressure, power on/off, error or fault condition, flow rate, flow resistance, infusion temperature, bath temperature, pumping time, battery charge, temperature profile (maximums and minimums), cover open or closed, history log or graph, and additional status details and messages, which are preferably further transmittable to a remote location for data storage and/or analysis. Flow and pressure sensors or transducers in transporter 1900 may be used to calculate various organ characteristics including pump pressure and vascular resistance of an organ, which can be stored in computer memory to allow for analysis of, for example, vascular resistance history, as well as to detect faults in the apparatus, such as elevated pressure.

Transporter 1900 has latches 1930 that require positive user action to open, thus avoiding the possibility that transporter 1900 inadvertently opens during transport. Latches 1930 hold top 1940 in place on transporter 1900. Top 1940 or a portion thereof may be constructed with an optically clear material to provide for viewing of the cassette and organ perfusion status. Transporter 1900 may be configured with a cover open detector that monitors and displays if the cover is open or closed. Transporter 1900 may be configured with an insulating exterior of various thicknesses to allow the user to configure transporter 1900 for varying extents and distances of transport. In embodiments, compartment 1950 may be provided to hold patient and organ data such as charts, testing supplies, additional batteries, hand-held computing devices and/or other accessories for use with transporter 1900. Transporter 1900 may also be configured with means for displaying a UNOS label and/or identification and return shipping information.

Figure 20:
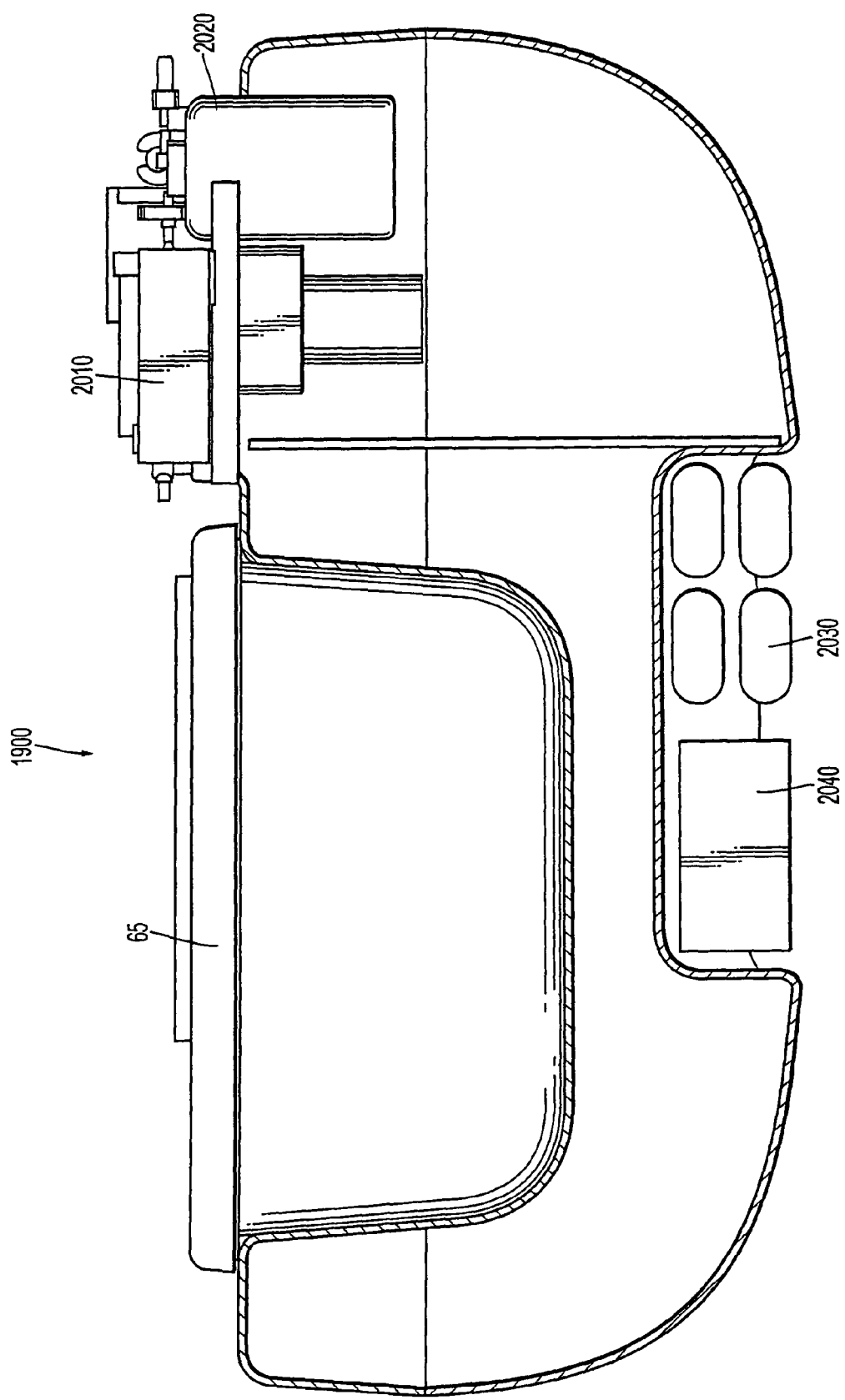
FIG. 20 shows a cross-section view of an organ transporter of FIG. 19.

FIG. 20 shows a cross-section view of a transporter 1900. Transporter 1900 contains cassette 65 and pump 2010. Cassette 65 may be placed into and taken out of transporter 1900 without disconnecting tubeset 400 from cassette 65, thus maintaining sterility of the organ. Sensors in transporter 1900 can detect the presence of cassette 65 in transporter 1900, and depending on the sensor, can read the organ identity from a barcode or radio frequency or other smart tag that may be integral to cassette 65. This allows for automated identification and tracking of the organ and helps monitor and control the chain of custody. A global positioning system may be added to transporter 1900 and/or cassette 65 to facilitate tracking of the organ. Transporter 1900 can be interfaced to a computer network by hardwire connection to a local area network or by wireless communication while in transit. This interface allows perfusion parameters, vascular resistance, and organ identification and transporter and cassette location to be tracked and displayed in real-time or captured for future analysis.

Transporter 1900 also preferably contains a filter 2020 to remove sediment and other particulate matter, preferably ranging in size from 0.05 to 15 microns in diameter or larger, from the perfusate to prevent clogging of the apparatus or the organ. Transporter 1900 also contains batteries 2030, which may be located at the bottom of transporter 1900 or beneath pump 2010 or at any other location that provides easy access to change batteries 2030. Batteries 2030 may be rechargeable outside of transporter 1900 or while intact within transporter 1900 and/or are preferably hot-swappable one at a time. Batteries 2030 are preferably rechargeable rapidly and without full discharge. Transporter 1900 may also provide an additional storage space 2040 at the bottom of transporter 1900 for power cords, batteries and other accessories. Transporter 1900 may also include a power port for a DC hookup to a vehicle such as an automobile or airplane and/or for an AC hookup.

Figure 21:
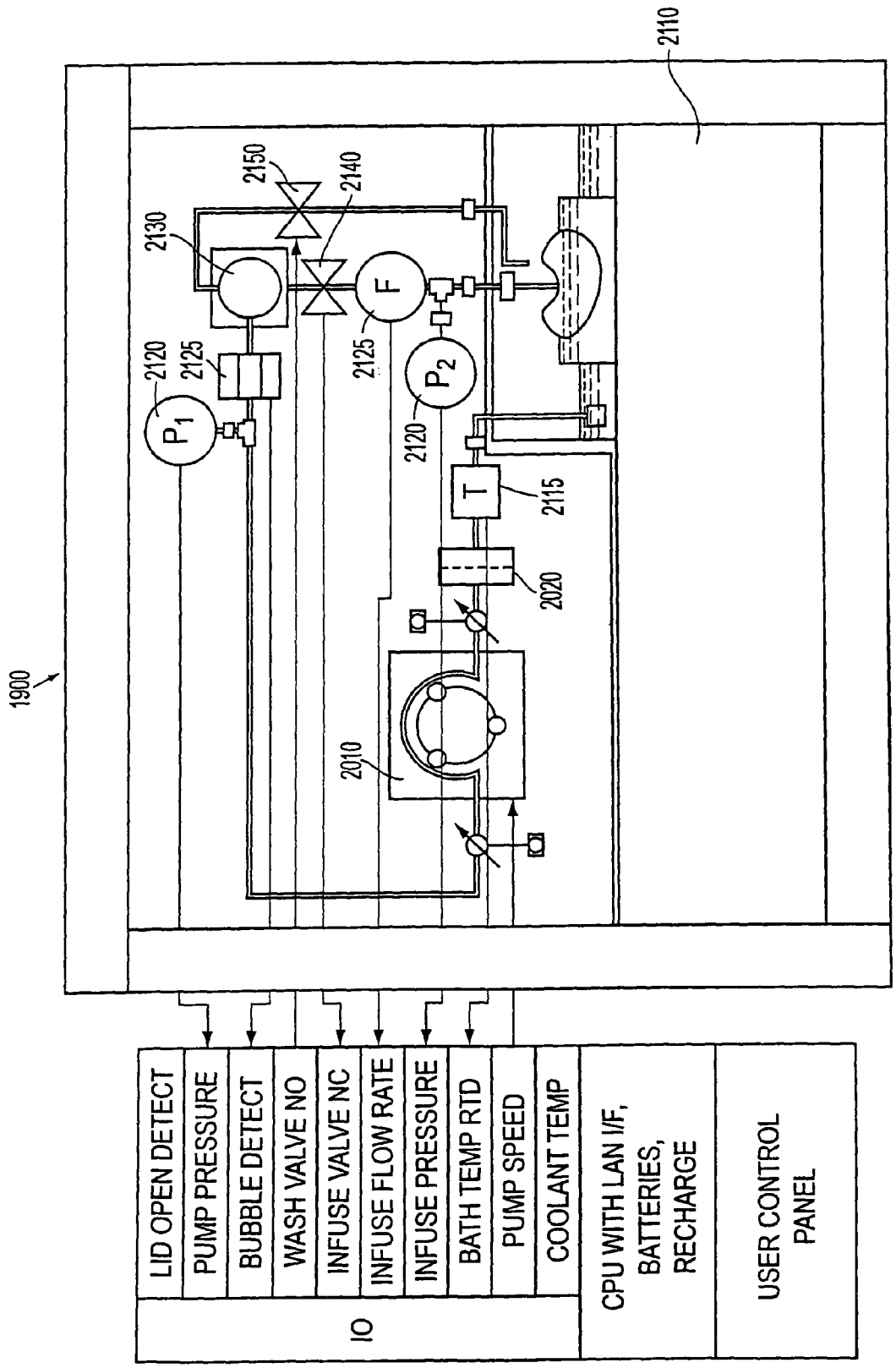
FIG. 21 shows a block diagram of an organ transporter of FIG. 19.

FIG. 21 shows a block diagram of transporter 1900. Transporter 1900 of FIG. 21 is intended to provide primarily hypothermic perfusion, and may operate at any temperatures, for example in the range of −25 to 60° C., approximately 0 to 8° C., preferably approximately 4° C. The temperature may be adjusted based on the particular fluids used and adapted to the particular transport details, such as length of time of transport. Transporter 1900 is cooled by coolant 2110, which may be an ice and water bath or a cryogenic material. In embodiments using cryogenic materials, the design should be such that organ freezing is prevented. The temperature of the perfusate bath surrounding the organ is monitored by temperature transducer 2115. Transporter 1900 also contains filters 2020 to remove sediment and particulate, ranging in size from 0.05 to 15 microns in diameter or larger, from the perfusate to prevent clogging of the apparatus or the organ. Using a filter 2020 downstream of pump 2010 allows for capturing inadvertent pump debris and also dampens pressure spikes from pump 2010.

The flow of perfusate within transporter 1900 is controlled by pump 2010, which is preferably a peristaltic or roller pump. Pump 2010 is preferably not in contact with the perfusate to help maintain sterility. In addition, tubeset 400 may be attached to pump 2010 without opening the tubing circuit. Pump 2010 is controlled by a computer or microcontroller. The computer can actively modulate the angular velocity of pump 2010 to reduce the natural pulse actions of pump 2010 to a low level, resulting in essentially non-pulsatile flow. Further computer control can impose a synthesized pressure pulse profile that can be sinusoidal or physiological or otherwise. The average flow rate and pressure can be made independent of pulse repetition rate by pulse width modulating or amplitude modulating the synthesized pressure pulses. Control over some or all of the pulse parameters can be made available to users through control panel 1920 or over a network. Pulse control can be organ specific. In the case of a liver, a single pump can provide continuous flow to the portal vein at, for example, 1 to 3 liters per minute while providing pulsatile flow to the hepatic artery at, for example, 100 to 300 ml per minute. Synchronizing the shunt valves to the pump controller allows independent pressure regulation of the two flows.

The flow of the perfusate into the organ is monitored by flow sensor 2125. Pressure transducers 2120 may be present to monitor the pressure the perfusate places on the tubing. Pressure transducers 2120 may be used to monitor the pump pressure and/or the infusion pressure. A pressure transducer 2120 may be present just upstream of the organ to monitor the organ infusion pressure. Transporter 1900 may be configured with a bubble detector 2125 to detect bubbles before the perfusate enters bubble trap 2130. Bubble detectors, such as bubble detector 2125, may be used to detect bubbles in, for example, the infuse line and/or in the pump output line. Bubble trap 2130 removes air bubbles from the perfusate and vents the bubbles into the wash tube. Bubble trap 2130 may be disposable and may be constructed integral to tubeset 400. Perfusate exiting bubble trap 2130 can either continue through infuse valve 2140 or wash valve 2150. Wash valve 2150 is normally open and infuse valve 2140 is normally closed. Preferably, wash valve 2150 and infuse valve 2140 operate dependently in an on/off manner, such that if one valve is open, the other valve is closed. Although infuse valve 2140 is normally closed, if the sensor and monitors all report suitable perfusion parameters present in transporter 1900, then infuse valve 2140 may be opened to allow organ perfusion. In the occurrence of a fault, such as elevated perfusion pressure above a suitable level for the organ, infuse valve 2140 switches back to closed and wash valve 2150 is opened to divert fluid flow into the perfusate bath surrounding the organ. This provides a failsafe mechanism that automatically shunts perfusate flow and prevents organ perfusion in case of a power failure or computer or electronics malfunction. A pressure transducer 2120, such as designated by $P_2$, may be hardwired, redundant to the computer and software control, to wash valve 2150 and infuse valve 2140 to quickly deliver a default message to the valves in the case of a pressure malfunction. In embodiments, the diverted fluid may be separately collected in another container or compartment.

Figure 22:
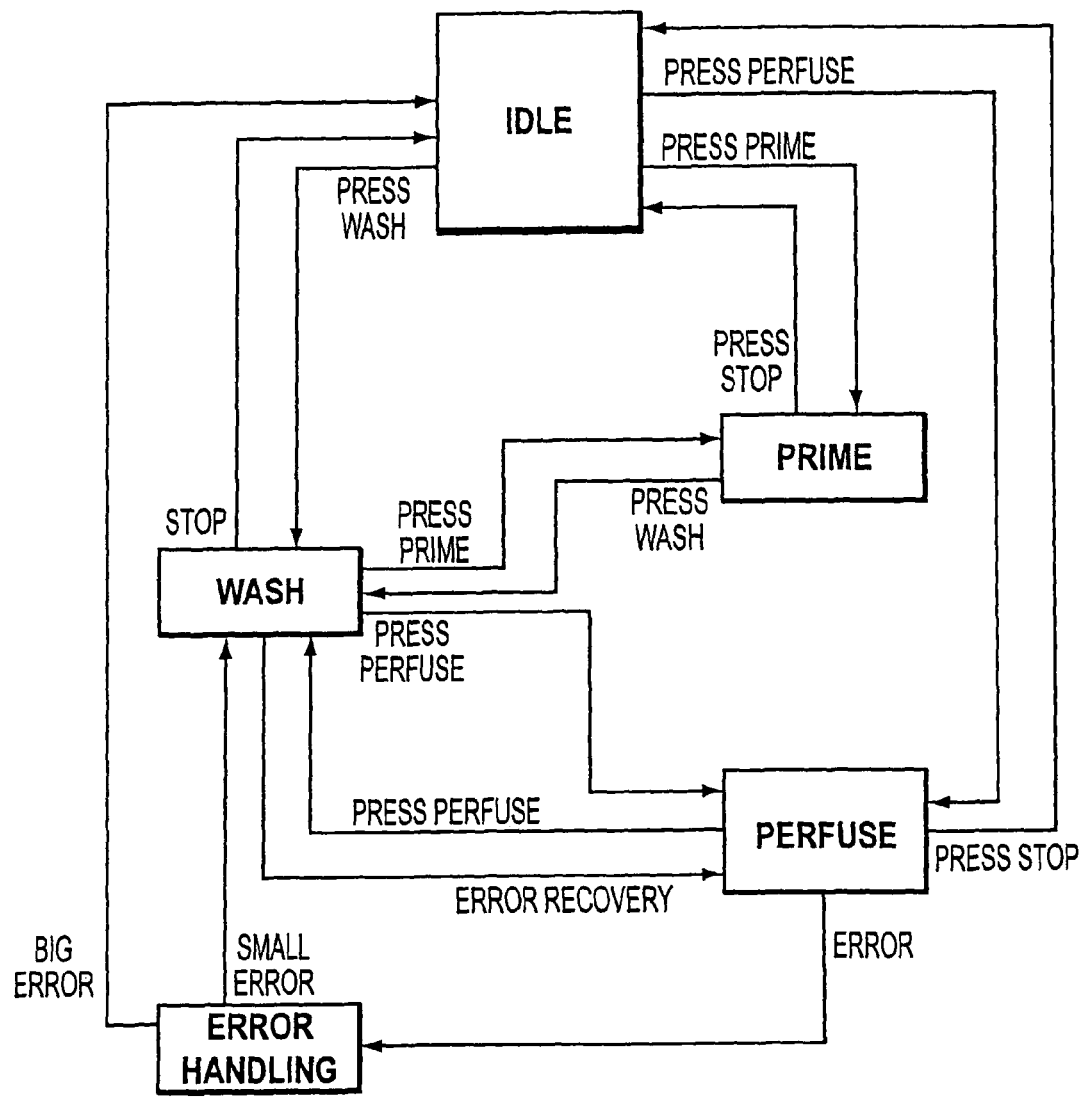
FIG. 22 shows operation states of an organ transporter of FIG. 19.

FIG. 22 shows various operation states of transporter 1900. For example, using the controls provided on control panel 1920, a user may select operations such as perfuse, idle, wash and prime. FIG. 22 shows various options depending on the present state of transporter 1900. The labels idle, prime, wash, perfuse and error handling indicate the state of transporter 1900 that is preferably displayed on control panel 1920 during the corresponding operation. For example, when transporter 1900 is in a wash operation, control panel 1920 displays the wash operation indicator, such as an LED display. The arrows connecting the various operations of transporter 1900 indicate the manual and automatic actions that may occur to transition transporter 1900 between operation states. Manual actions require the user to act, for example by pressing a button or turning a knob or dial. FIG. 22 exemplifies pressing a button or other indicator, for example, to move from a perfusion operation to an idle operation by pressing the stop button (Press Stop). To move directly into a perfuse operation from an idle operation, a user presses the perfuse button (Press Perfuse).

Automatic operations may be controlled by the passage of time and/or by an internal monitor within transporter 1900. Such automatic operation is shown in FIG. 22, for example, connecting the prime operation to the idle operation. If the prime operation has been completed according to the internal transporter program parameters before the wash button has been pressed, transporter 1900 returns to an idle operation. Another automatic operation occurs during a perfuse operation if a fault or error occurs, such as overpressurization of the organ. When an error or fault occurs, transporter 1900 can move to an error handling operation to determine the extent or degree of the fault or error. If the fault or error is determined to be a small or correctable error, transporter 1900 moves into a wash operation. If transporter 1900 can then adjust the system parameters to handle the fault or error, transporter 1900 moves back to perfuse (Error Recovery). If transporter 1900 can not adjust the system parameters to handle the fault or error, transporter 1900 moves to an idle operation. If the error or fault detected is determined to be substantial, transporter 1900 may move directly into an idle operation.

Figure 23:
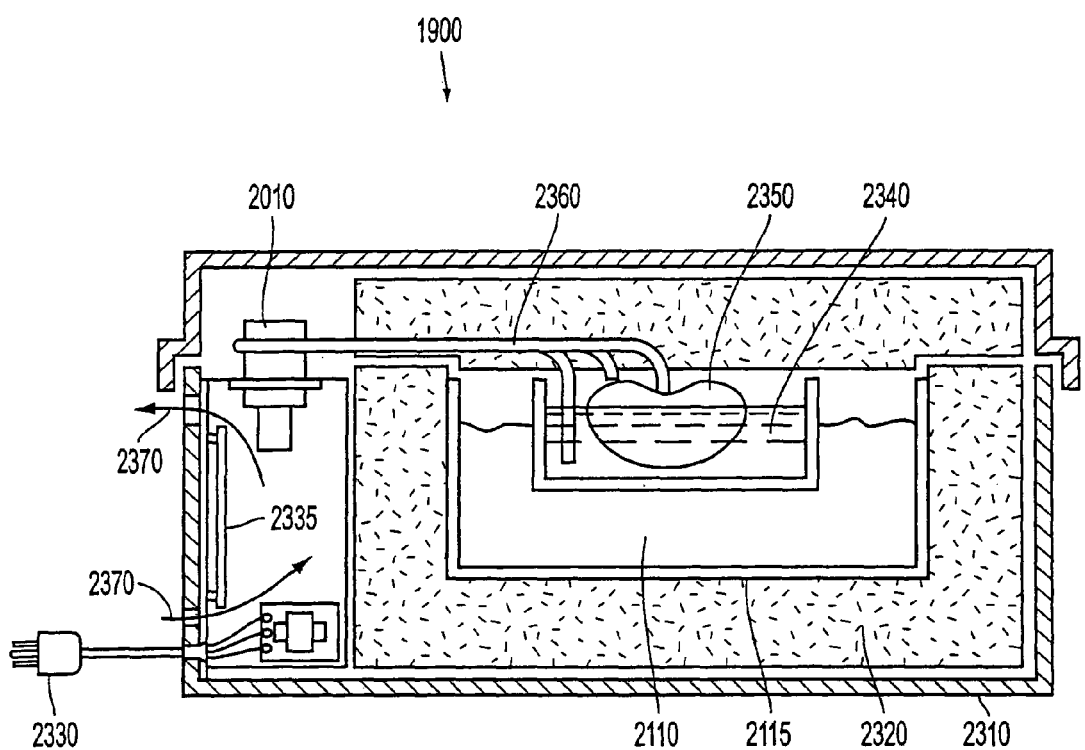
FIG. 23 shows an alternative cross-section view of an organ transporter of FIG. 19.

FIG. 23 shows an alternative cross-section of transporter 1900. Transporter 1900 may have an outer enclosure 2310 constructed of metal, or preferably a plastic or synthetic resin that is sufficiently strong to withstand penetration and impact. Transporter 1900 contains insulation 2320, preferably a thermal insulation made of, for example, glass wool or expanded polystyrene. Insulation 2320 may be various thicknesses ranging from 0.5 inches to 5 inches thick or more, preferably 1 to 3 inches, such as approximately 2 inches thick. Transporter 1900 is cooled by coolant 2110, which may be, e.g., an ice and water bath or a cryogenic material. In embodiments using cryogenic materials, the design should be such that organ freezing is prevented. An ice and water mixture is preferably in an initial mixture of approximately 1 to 1, however, in embodiments the ice and water bath may be frozen solid. Transporter 1900 can be configured to hold various amounts of coolant, preferably up to 10 to 12 liters. An ice and water bath is preferable because it is inexpensive and can not get cold enough to freeze the organ. Coolant 2110 preferably lasts for a minimum of 6 to 12 hours and more preferably lasts for a minimum of 30 to 50 hours without changing coolant 2110. The level of coolant 2110 may be viewed through a transparent region of transporter 1900 or may be automatically detected and monitored by a sensor. Coolant 2110 can be replaced without stopping perfusion or removing cassette 65 from transporter 1900. Coolant 2110 is maintained in a watertight compartment 2115 of transporter 1900. Compartment 2115 prevents the loss of coolant 2110 in the event transporter 1900 is tipped or inverted. Heat is conducted from the walls of the perfusion reservoir and cassette 65 into coolant 2110 enabling control within the desired temperature range. Coolant 2110 is a failsafe cooling mechanism because transporter 1900 automatically reverts to cold storage in the case of power loss or electrical or computer malfunction. Transporter 1900 may also be configured with a heater to raise the temperature of the perfusate.

Transporter 1900 may be powered by batteries or by electric power provided through plug 2330. An electronics module 2335 is also provided in transporter 1900. Electronics module 2335 is cooled by vented air convection 2370, and may further be cooled by a fan. Preferably, electronic module 2335 is positioned separate from the perfusion tubes to prevent the perfusate from wetting electronics module 2335 and to avoid adding extraneous heat from electronics module 2335 to the perfusate. Transporter 1900 has a pump 2010 that provides pressure to perfusate tubing 2360 to deliver perfusate 2340 to organ 2350. Transporter 1900 may be used to perfuse various organs such as a kidney, heart, liver, small intestine and lung. Transporter 1900 and cassette 65 may accommodate various amounts of perfusate 2340, for example up to 3 to 5 liters. Preferably, approximately 1 liter of a hypothermic perfusate 2340 is used to perfuse organ 2350. Organ 2350 may be various organs, including but not limited to a kidney, heart, lung, liver or small intestine.

Cassette 65 and transporter 1900 are preferably constructed to fit or mate such that efficient heat transfer is enabled. The geometric elements of cassette 65 and transporter 1900 are preferably constructed such that when cassette 65 is placed within transporter 1900, the elements are secure for transport.

Figure 24:
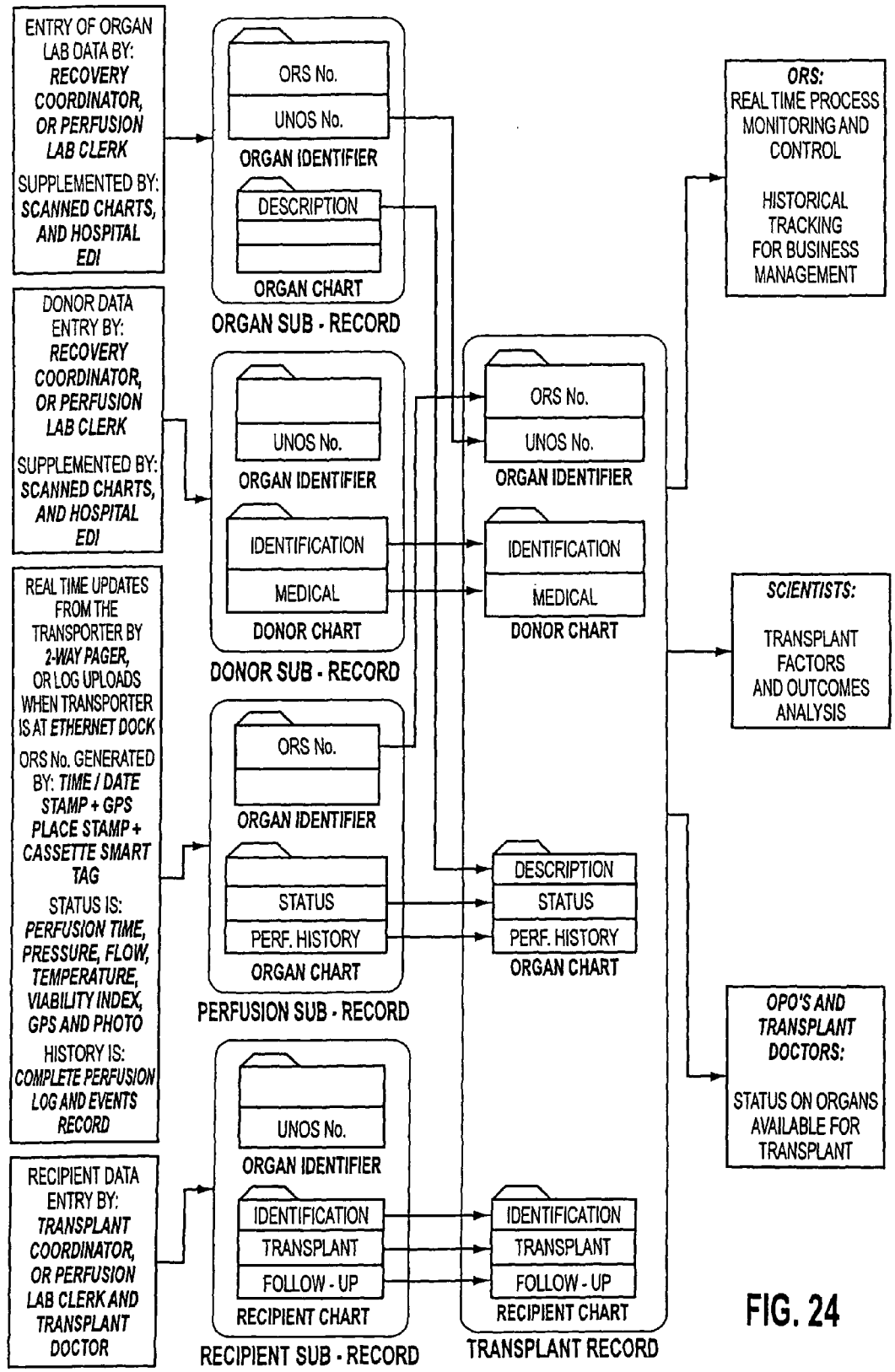
FIG. 24 shows data structures and information transfer schemes of a perfusion and organ transplant system of the present invention.

FIG. 24 shows various data structures and information connections that can be facilitated to assist in the overall communication and data transfers that may be beneficial before, during and after organ transplantation. The perfusion apparatus, transporter, cassette, and organ diagnostic apparatus may be networked to permit remote management, tracking and monitoring of the location and therapeutic and diagnostic parameters of the organ or organs being stored or transported. The information systems may be used to compile historical data of organ transport and storage, and provide cross-referencing with hospital and UNOS data on the donor and recipient. The systems may also provide outcome data to allow for ready research of perfusion parameters and transplant outcomes. For example, information regarding the donor may be entered at the location where an organ is recovered from a donor. Information may also be directly recovered from the perfusion, diagnostic or transporter apparatus to monitor organ status and location. Various types of information may be grouped into sub-records or sub-directories to assist in data management and transfer. All the sub-records may be combined to form an overall transplant record, which may be disseminated to or retrievable by physicians, scientists or other organizations for tracking and monitoring purposes.

Preferred embodiments of transporter 1900 can automatically log much or all of the perfusion process data and transporter 1900 events into an internal database. A radio frequency or barcode labeled tag or the like for each cassette 65 allows transporter 1900 to reference the data uniquely to each organ. When transporter 1900 reaches a docking port, transporter 1900 can upload data to a main database computer over a LAN. Transporter 1900 can also provide real-time status whenever transporter 1900 is connected to the LAN. Transporter 1900 can also be configured with a wireless communications setup to provide real-time data transfer during transport. Perfusion apparatus 1 can also be connected to the LAN and since perfusion apparatus is generally stationary, data uploads can occur continuously and in real-time. The data can be cross-referenced with UNOS data to utilize the UNOS data on organ identification, donor condition, donor logistics, recipient logistics and recipient outcomes. Data may be displayed and accessed on the Internet to facilitate monitoring from any location.

Within the perfusion, diagnostic and/or transporter apparatus, the organ bath is preferably cooled to a predetermined temperature by a second thermoelectric unit 30b, as shown in FIG. 2, in heat transfer communication with the organ chamber 40. Alternatively and preferably where the organ perfusion device is going to be transported, the medical fluid within reservoir 10 can be cooled utilizing a heat transfer device such as an ice and water bath or a cryogenic fluid heat exchanger apparatus such as that disclosed in co-pending application Ser. No. 09/039,443, which is hereby incorporated by reference. A temperature sensor T2 within the organ chamber 40 relays the temperature of the organ 60 to the microprocessor 150, which adjusts the thermoelectric unit 30b to maintain a desired organ temperature and/or displays the temperature on the control and display areas 5c for manual adjustment.

Medical fluid may be fed from the bag 15a directly to an organ 60 disposed in the organ chamber 40 through tubing 50a, 50b,50c or from bag 15b through tubing 50d,50e,50c by opening valve $LV_4$ or $LV_3$, respectively. Conventional medical fluid bag and tubing connections may be utilized. All tubing is preferably disposable, easily replaceable and interchangeable. Further, all tubing is preferably formed of or coated with materials compatible with the medical fluids used, more preferably non-thrombogenic materials. An end of the tubing 50c is inserted into the organ 60. The tubing may be connected to the organ(s) with conventional methods, for example, with sutures. The tubing may include a lip to facilitate connection to the organ. Alternatively, cannula 1820 described above may be used with or without connection to an organ chair 1800. However, the specific methods and connection depend on the type of organs(s) to be perfused.

The microprocessor 150 preferably controls the pressure source 20 in response to signals from the pressure sensor P1 to control the pressure of the medical fluid fed into the organ 60. The microprocessor 150 may display the pressure on the control and display areas 5a, optionally for manual adjustment. A fluid flow monitor F1 may also be provided on the tubing 50c to monitor the flow of medical fluid entering the organ 60 to indicate, for example, whether there are any leaks present in the organ.

Alternatively, the medical fluid may be fed from the reservoir tank 17 via tubing 51 into an intermediary tank 70 preferably having a pressure head of approximately 5 to 40 mm Hg. Medical fluid is then fed by gravity or, preferably, pressure, from the intermediary tank 70 to the organ 60 along tubing 50c by activating a valve $LV_6$. A level sensor 71 may be provided in the intermediary tank 70 in order to maintain the pressure head. Where a plurality of organ chambers 40 and organs 60 are provided, the organs 60 are connected in parallel to the reservoir 10 utilizing suitable tubing duplicative of that shown in FIG. 2. See, for example, FIG. 12. The use of pneumatically pressurized and gravity fed fluid pumps configured to avoid overpressurization even in cases of system failure reduces or prevents general tissue damage to the organ and the washing away of or damage to the vascular endothelial lining of the organ. Thus, organ perfusion in this system can be performed, e.g., with either hydrostatic perfusion (gravity or pressure fed flow) or peristaltic perfusion by introducing flow to the organ from a peristaltic (roller) pump.

A bubble detection system may be installed to sense bubbles in the perfusate. An air sensor and sensor board are preferably used. The output of the sensor activates a debubbler system, such as an open solenoid valve, to rid bubbles from the perfusate flow prior to organ introduction. As with all of the sensors and detectors in this system, the bubble detector may be positioned at any point in the system that is effective based on the particular parameters or design characteristics of the system. For example, a bubble detector and debubbler system BD may be positioned between the cam valve 205 and pressure sensor P1, as shown in FIG. 1.

Figure 13A:
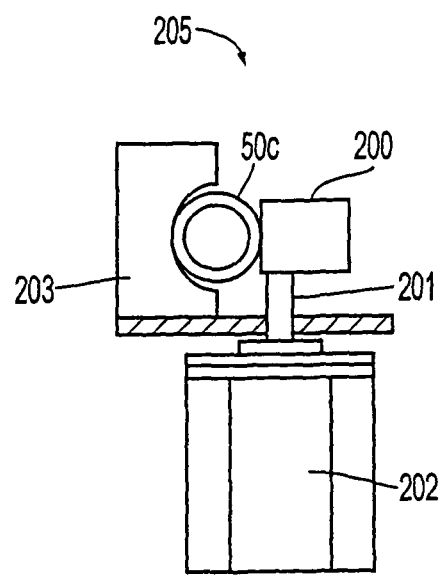
FIGS. 13A and 13B show a stepping motor/cam valve according to the invention.
Figure 13B:
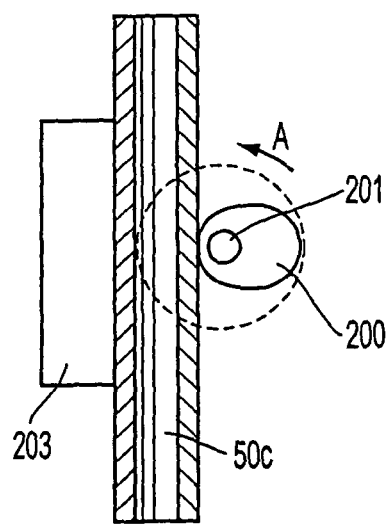

A stepping motor/cam valve 205, or other suitable variable valve such as a rotary screw valve, may be arranged on the tubing 50c to provide pulsatile delivery of the medical fluid to the organ 60, to decrease the pressure of the medical fluid fed into the organ 60, and/or to stop flow of medical fluid into the organ 60 if the perfusion pressure exceeds a predetermined amount. Alternatively, a flow diverter or shunt line may be provided in the perfusion apparatus to which the fluid flow is diverted in the occurrence of a fault, such as excess pressure, for example by opening and closing a valve or a series of valves. Specific embodiments of the stepping motor/cam valve are shown in FIGS. 13A-13B and 14A-14F. FIGS. 13A-13B show a stepping motor/rotational type cam valve.

FIG. 13A is a top view of the apparatus. Tubing, for example, tubing 50c, is interposed between a support 203 and cam 200. Cam 200 is connected by a rod 201 to stepping motor 202. FIG. 13B is a side view of the apparatus. The dashed line shows the rotational span of the cam 200. In FIG. 13B, the cam 200 is in its non-occluding position. Rotated 180 degrees, the cam 200 totally occludes the tubing 50c with varying degrees of occlusion therebetween. This stepping motor/cam valve is relatively fast, for example, with respect to the embodiment shown in FIGS. 14A-14F; however, it requires a strong stepping motor.

Figure 14A:
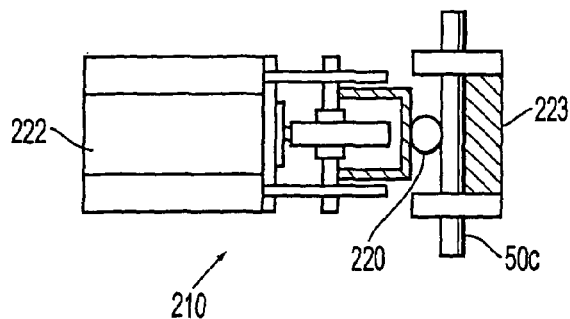
FIGS. 14A-14F show another stepping motor/cam valve according to the invention.
Figure 14B:
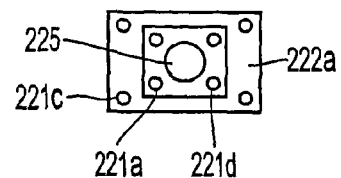
Figure 14C:
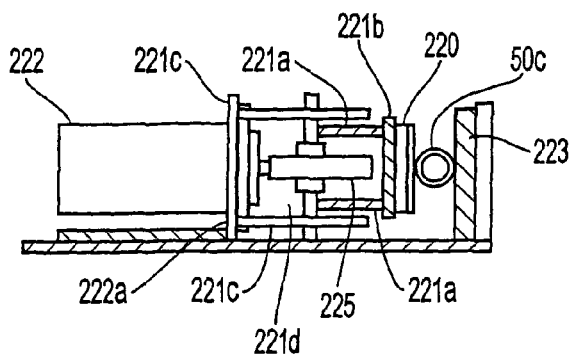
Figure 14D:
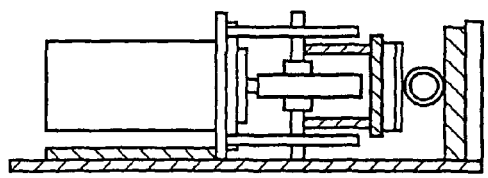
Figure 14E:
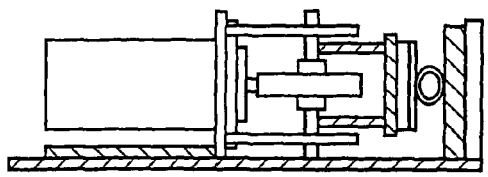
Figure 14F:
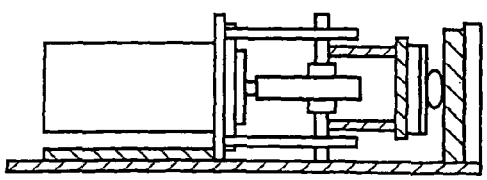

FIGS. 14A-14F disclose another stepping motor/cam valve 210 according to the invention. FIG. 14A is a side view of the apparatus while FIG. 14C is a top view. Tubing, for example, tubing 50c, is interposed between cam 220 and support 223. The cam 220 is connected to stepping motor 222 by supports 221a-221d and helical screw 225, which is connected to the stepping motor 222 via plate 222a. FIG. 14B shows the supports 221a and plate 222a in front view. As shown in FIG. 14D, where the support 221d is to the left of the center of the helical screw 225, the tubing 50c is not occluded. However, as the helical screw 225 is turned by the stepping motor 222, the support 221d moves to the left (with respect to FIGS. 14D-14F) toward a position where the cam 220 partially or fully occludes the tubing 50c. Such apparatus is slower than the apparatus of FIGS. 13A-13B, but is more energy efficient.

Medical fluid expelled from the organ 60 which has collected in the bottom of the bag 69 (the cassette 65 or the organ chamber 40) is either pumped out through tubing 81 by a pump 80 for filtration, passing through a filter unit 82 and being returned to the organ bath, or is pumped out by a pump 90 for circulation through tubing 91. The pumps 80, 90 are preferably conventional roller pumps or peristaltic pumps; however, other types of pumps may also be appropriate.

Figure 25:
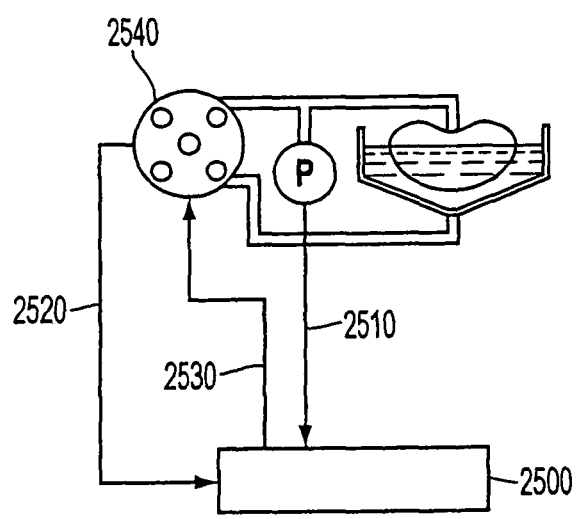

FIG. 25 shows a simplified schematic of a pump and pulse controller 2500 and the interaction of the pump and pulse controller with a perfusion apparatus, such as shown in FIG. 1. Pump and pulse controller 2500 receives pressure sensor data input 2510 from pressure sensor P and tachometer data input 2520. A tachometer may be used to set the phase angle of the active wave. Pump and pulse controller 2500 converts this information to motor drive output 2530, which powers pump 2540. FIG. 25A shows various modes of operation that pump and pulse controller 2500 can provide and how pump and pulse controller 2500 eliminates pressure pulse waves from the perfusate flow and how it modulates perfusate flow rate while maintaining a constant pressure pulse rate.

A peristaltic pump driven at a constant speed provides a constant pressure wave in the associated tubing. FIG. 25A shows in the first mode of operation the waveforms that result from a constant drive speed applied to a peristaltic pump. The second mode of operation, called active continuous, shows how the pressure pulse wave can be eliminated or canceled out by applying a motor drive wave that is opposite to the pressure wave of the pump. In the third mode of operation, called active waveform amplitude modulating, the pump pressure pulse wave is canceled by the motor drive wave, and a selected wave is added with a new amplitude as compared to the original pressure pulse wave amplitude. In the fourth mode of operation, called active waveform pulse width modulating, the pump pressure pulse wave is canceled by the motor drive wave, and a selected wave is added with a new pulse width as compared to the original pressure pulse wave width. In an alternative mode of operation, the frequency may be modulated by adding a new frequency wave to the canceled waves.

A level sensor L2 in communication with the microprocessor 150 (see FIG. 3) ensures that a predetermined level of effluent medical fluid is maintained within the organ chamber 40. As shown in FIG. 2, a temperature sensor T1 disposed in the tubing 91 relays the temperature of the medical fluid pumped out of the organ bath along tubing 91 to the microprocessor 150, which monitors the same. A pressure sensor P2 disposed along the tubing 91 relays the pressure therein to the microprocessor 150, which shuts down the system if the fluid pressure in the tubing 91 exceeds a predetermined limit, or activates an alarm to notify the operator that the system should be shut down, for example, to clean filters or the like.

As the medical fluid is pumped along tubing 91 it preferably passes through a filter unit 95 (e.g., 25μ, 8μ, 2μ, 0.8μ, 0.2μ and/or 0.1μ filters); a $CO_2$ scrubber/$O_2$ membrane 100 and an oxygenator 110, for example, a JOSTRA™ oxygenator. The $CO_2$ scrubber/$O_2$ membrane 100 is preferably a hydrophobic macroporous membrane with a hydrophilic (e.g., Hypol) coating in an enclosure. A vacuum source (not shown) is utilized to apply a low vacuum on a side opposite the hydrophilic coating by the activation of valve $VV_1$. A hydrostatic pressure of approximately 100 mm Hg is preferred for aqueous passage through the membrane. The mechanical relief valve (not shown) prevents the pressure differential from attaining this level. Immobilized pegolated carbonic anhydrase may be included in the hydrophilic coating. This allows bicarbonate to be converted to $CO_2$ and subsequently removed by vacuum venting. However, with organs such as kidneys which have the ability to eliminate bicarbonate, this may be unnecessary except in certain cases.

The oxygenator 110 is preferably a two stage oxygenator which preferably includes a hydrophilically coated low porosity oxygen permeable membrane. A portion of the medical fluid is diverted around the oxygenator along tubing 111 in which is disposed a viability sensor V1, which senses fluid characteristics, such as organ resistance (pressure/flow), pH, $pO_2$, $pCO_2$, LDH, T/GST, Tprotein, lactate, glucose, base excess and ionized calcium levels indicative of an organ's viability. The viability sensor V1 is in communication with the microprocessor 150 and allows the organ's viability to be assessed either automatically or manually. One of two gases, preferably 100% oxygen and 95/5% oxygen/carbon dioxide, is placed on the opposite side of the membrane depending on the pH level of the diverted medical fluid. Alternatively, another pump (not shown) may be provided which pumps effluent medical fluid out of the organ chamber 40 and through a viability sensor before returning it to the bath, or the viability sensor can be placed on tubing 81 utilizing pump 80. In embodiments, the fluid characteristics may be analyzed in a separate diagnostic apparatus and/or analyzer as shown in FIGS. 28-31.

The sensed fluid characteristics, such as organ resistance (pressure/flow), pH, $pO_2$, $pCO_2$, LDH, T/GST, Tprotein, lactate, glucose, base excess and ionized calcium levels may be used to analyze and determine an organ's viability. The characteristics may be analyzed individually or multiple characteristics may be analyzed to determine the effect of various factors. The characteristics may be measured by capturing the venous outflow of the organ and comparing its chemistry to the perfusate inflow. The venous outflow may be captured directly and measured or the organ bath may be measured to provide a rough approximation of the fluid characteristics for comparisons over a period of time.

In embodiments, an organ viability index is provided taking into account the various measured factors identified above, such as vascular resistance, pH, etc. The index may be organ specific, or may be adaptable to various organs. The index compiles the monitored parameters into a diagnostic summary to be used for making organ therapy decisions and deciding whether to transplant the organ. The index may be automatically generated and provided to the physician. The index is preferably computer generated via a connection to the perfusion apparatus, transporter, cassette and/or organ diagnostic apparatus. The additional information, such as donor specific information, may be entered into a single computer at the site of the perfusion apparatus, transporter, cassette and/or organ diagnostic apparatus or may be entered in a remote computer and linked to the perfusion apparatus, etc. In embodiments, the index may be made available over a computer network such as a local area network or the Internet for quick comparison, remote analysis and data storage.

The organ viability index provides measurements and normal ranges for each characteristic, such as vascular resistance and perfusate chemistry characteristics based on pH, $pO_2$, $pCO_2$, LDH, T/GST, Tprotein, lactate, glucose, base excess and ionized calcium levels. For example, at approximately 5° C., normal pH may be from 7.00 and 8.00, preferably from 7.25 and 7.75 and more preferably from 7.50 and 7.60 and base excess may be in the range of from −10 to −40, preferably from −15 to −30, and more preferably from −20 to −25. Measurements that are outside the normal range may be indicated visually, e.g., by an asterisk or other suitable notation, aurally or by machine perceivable signals. The characteristics give the physician insight into the metabolism of the organ, such as stability of the metabolism, consumption of glucose, creation of lactic acid and oxygen consumption.

The index may also provide identifying information, such as age, gender, blood type of the donor and any expanded criteria; organ information, such as organ collection date and time, warm ischemia time, cold ischemia time and vascular resistance; apparatus information, such as flow rate, elapsed time the pump has been operating and pressure; and other identifiers such as UNOS number and physician(s) in charge. The index may additionally provide temperature corrections if desired.

Returning to FIG. 2 and the flow and/or treatment of the medical fluid or perfusate in perfusion apparatus 1, alternative to the pump 90, filter unit 95, the $CO_2$ scrubber/$O_2$ membrane 100 and/or the oxygenator 110, a modular combined pump, filtration, oxygenation and/or debubbler apparatus may be employed such as that described in detail in simultaneously filed co-pending U.S. patent application Ser. No. 09/039,318, which is hereby incorporated by reference. As shown in FIGS. 4-10, the apparatus 5001 is formed of stackable modules. The apparatus 5001 is capable of pumping a fluid through a system as well as oxygenating, filtering and/or debubbling the fluid. The modules are each formed of a plurality of stackable support members and are easily combinable to form a compact apparatus containing desired components. Filtration, oxygenation and/or degassing membranes are disposed between the support members.

Figure 7:
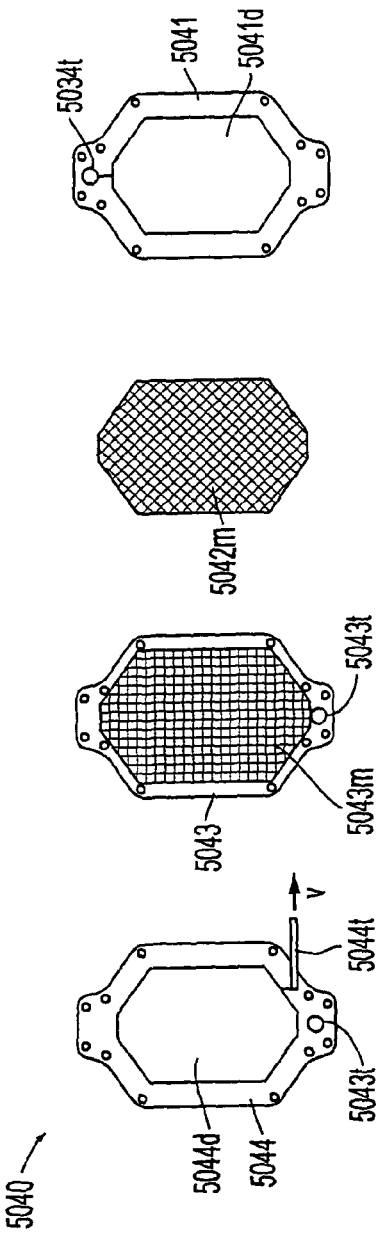
FIG. 7 is an exploded view of a debubbler module of a combined pump, filtration, oxygenation and/or debubbler apparatus according to the invention.
Figure 8:
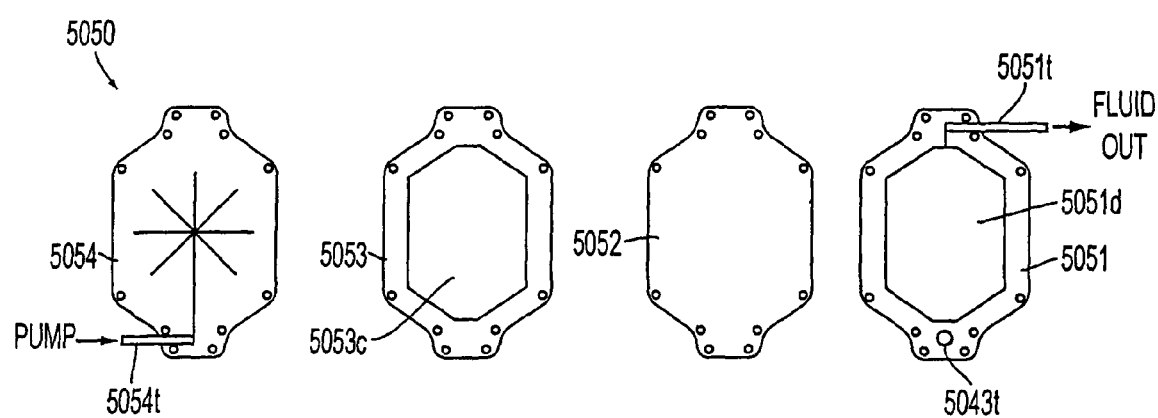
FIG. 8 is an exploded view of a second pump module of a combined pump, filtration, oxygenation and/or debubbler apparatus according to the invention.
Figure 9:
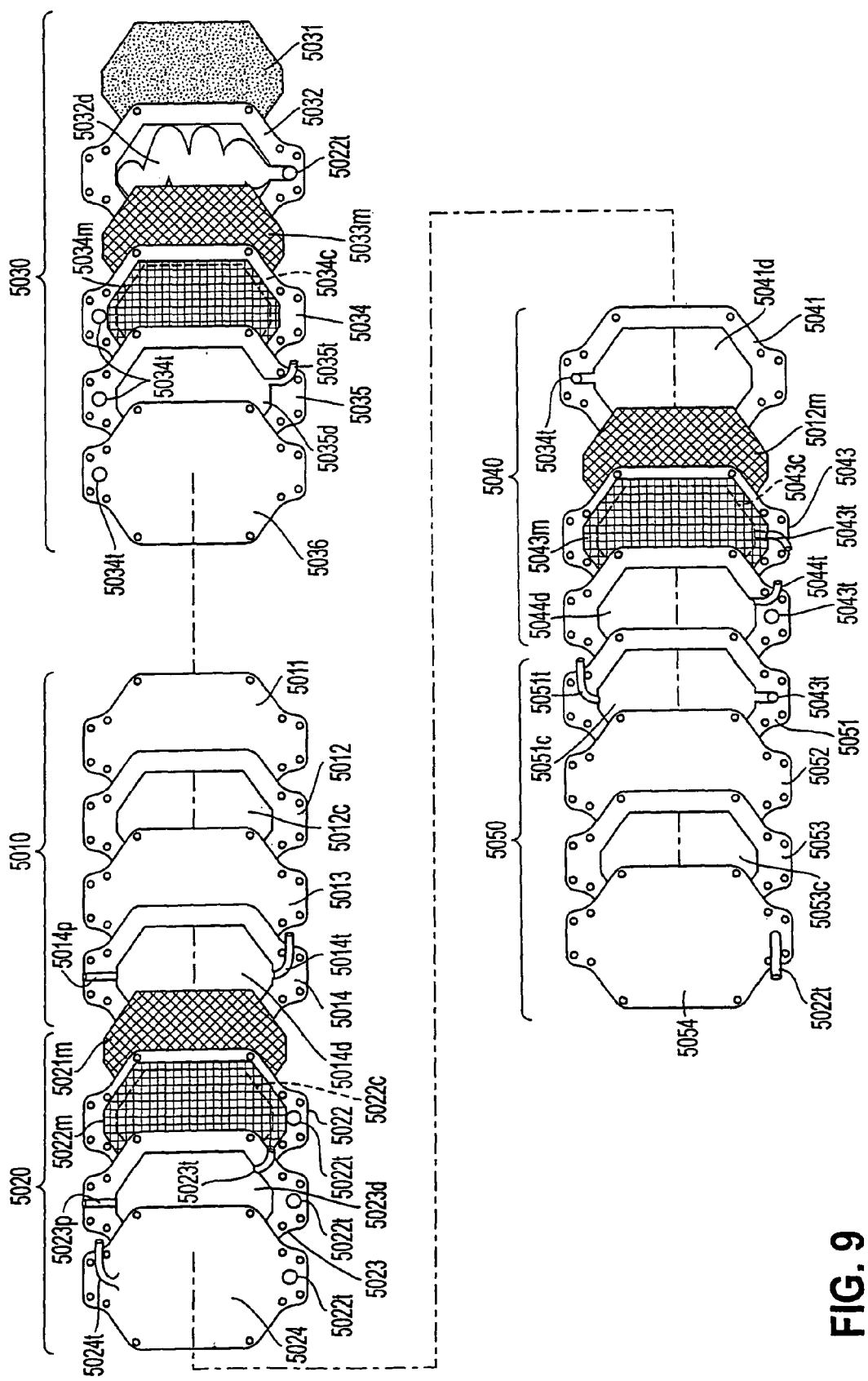
FIG. 9 is an exploded perspective view showing the modules of FIGS. 4-8 assembled together.
Figure 10:
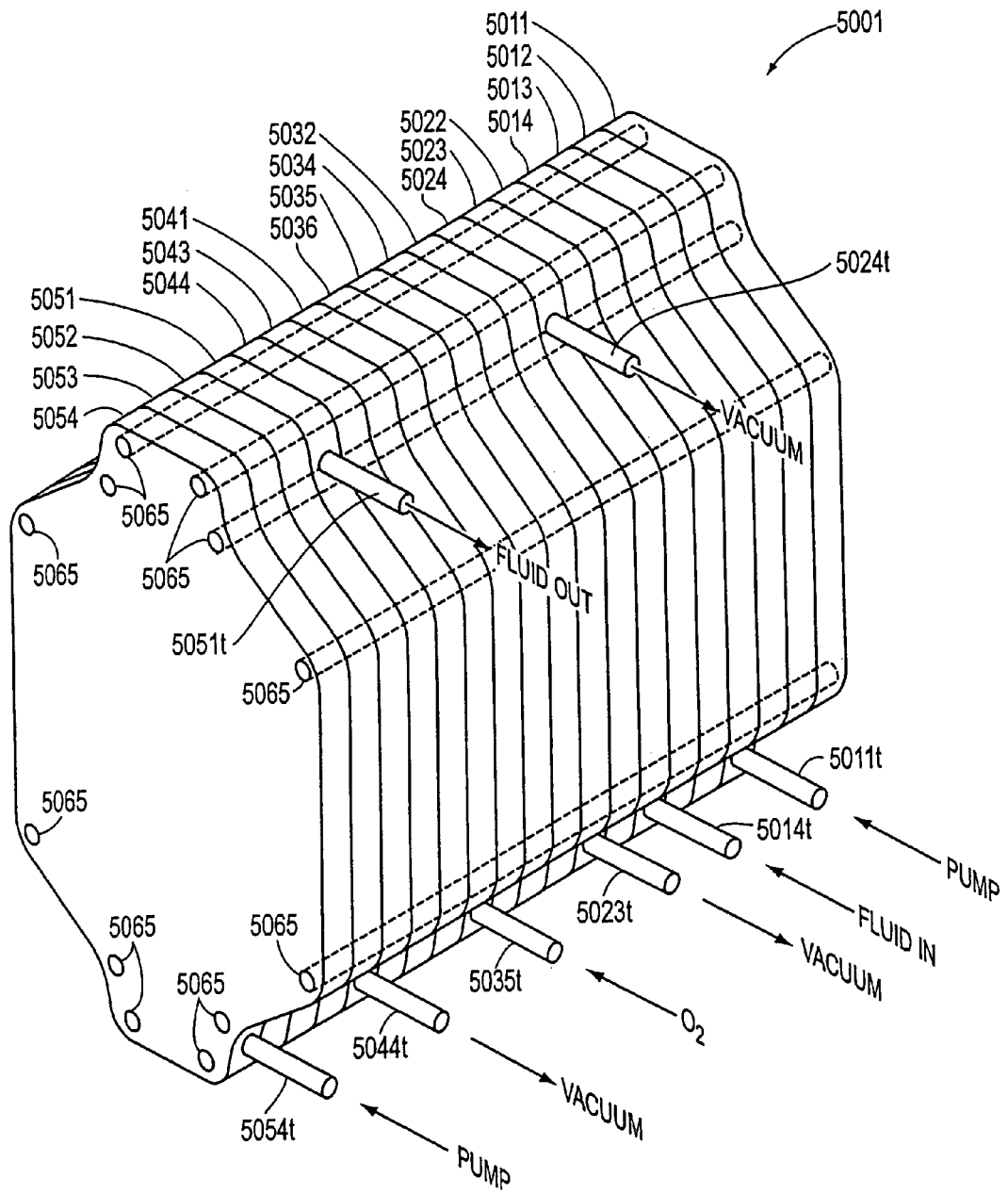
FIG. 10 is a front perspective view of an assembled modular combined pump, filtration, oxygenation and/or debubbler apparatus according to the invention.

FIGS. 4-8 show various modules that may be stacked to form a combined pump, filtration, oxygenation and/or debubbler apparatus, such as the combined pump, filtration, oxygenation and debubbler apparatus 5001 shown in FIGS. 9-10. As depicted in these figures, the combined pump, filtration, oxygenation and debubbler apparatus 5001 is preferably formed of a plurality of stackable support members groupable to form one or more modules.

Interposed between the plurality of stackable support member are filtration, oxygenation and/or degassing membranes depending on a particular user's needs. The filtration, oxygenation and/or degassing membranes are preferably commercially available macro-reticular hydrophobic polymer membranes hydrophilically grafted in a commercially known way, such as, for example, ethoxylation, to prevent protein deprivation, enhance biocompatibility with, for example, blood and to reduce clotting tendencies. The filtration membrane(s) is preferably hydrophilically grafted all the way through and preferably has a porosity (pore size) within a range of 15 to 35μ, more preferably 20 to 30μ, to filter debris in a fluid, preferably without filtering out cellular or molecular components of the fluid. The degassing membrane(s) and oxygenation membrane(s) are hydrophilically surface treated to maintain a liquid-gas boundary. The degassing membrane(s) and oxygenation membrane(s) preferably have a porosity of 15μ or less, more preferably 10μ or less.

Figure 4:
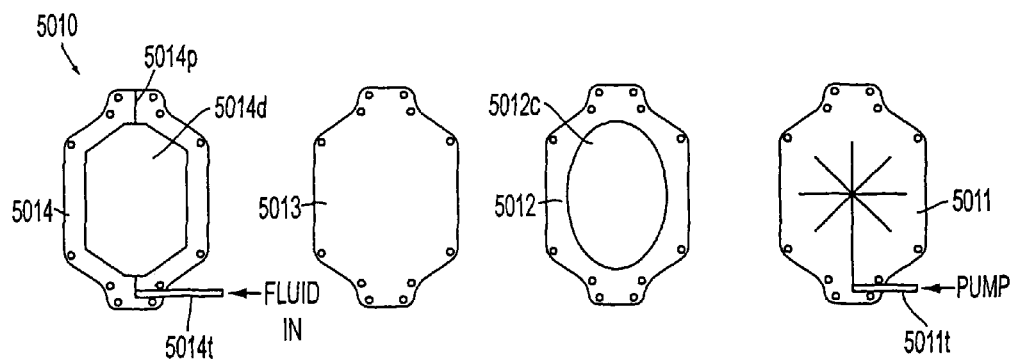
FIG. 4 is an exploded view of a first pump module of a combined pump, filtration, oxygenation and/or debubbler apparatus according to the invention.
Figure 5:
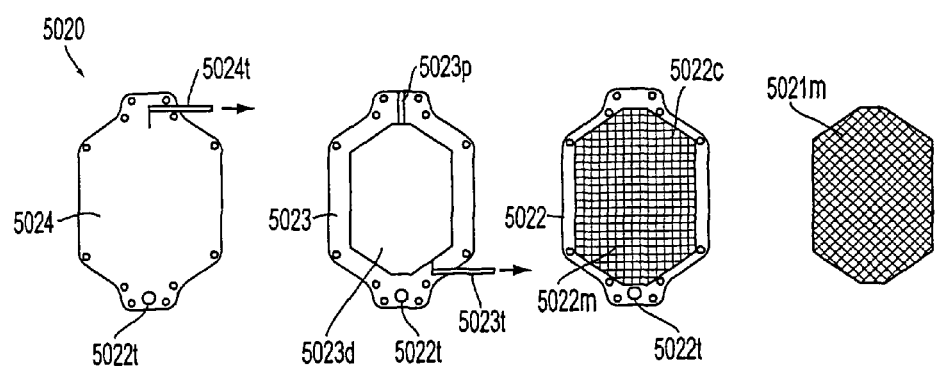
FIG. 5 is an exploded view of a filtration module of a combined pump, filtration, oxygenation and/or debubbler apparatus according to the invention.
Figure 6:
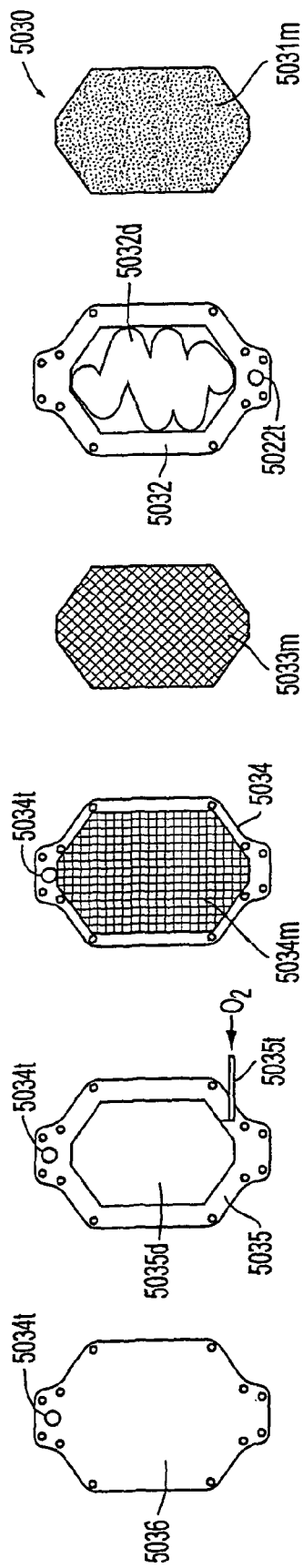
FIG. 6 is an exploded view of an oxygenation module of a combined pump, filtration, oxygenation and/or debubbler apparatus according to the invention.

The modules may include a first pump module 5010, as shown in exploded view in FIG. 4; a filtration module 5020, as shown in exploded view in FIG. 5; an oxygenation module 5030, as shown in exploded view in FIG. 6; a debubbler module 5040, as shown in exploded view in FIG. 7; and a second pump module 5050, as shown in exploded view in FIG. 8. The pump modules are each connected to a source of pump fluid and are actuated either manually or by the microprocessor. The support members are preferably similarly shaped. For example, the support members may each be plate-shaped; however, other shapes may also be appropriate. As shown in FIG. 10, the support members are preferably removably connected by screws or bolts 5065; however, other fasteners for assembling the apparatus may also be appropriate.

The first pump module 5010 preferably includes a first (end) support member 5011, a second support member 5012 with a cut-out center area 5012$c$, a diaphragm 5013 and a third support member 5014. The support members of this module and each of the other modules are preferably thin and substantially flat (plate-like), and can be formed of any appropriate material with adequate rigidity and preferably also biocompatibility. For example, various resins and metals may be acceptable. A preferred material is an acrylic/polycarbonate resin.

The first (end) support member 5011 is preferably solid and provides support for the pump module 5010. The first (end) support member 5011 preferably includes a domed-out cavity for receiving pump fluid such as air. Tubing 5011$t$ is provided to allow the pump fluid to enter the pump module 5010. The diaphragm 5013 may be made of any suitable elastic and preferably biocompatible material, and is preferably polyurethane. The third support member 5014 includes a domed-out fluid cavity 5014$d$ and tubing 5014$t$ for receiving fluid, such as, for example, blood or an artificial perfusate, into the cavity 5014$d$ of the pump module 5010. The first pump module, or any of the other modules, may also include a port 5014$p$ for sensors or the like. Preferably hemocompatible anti-backflow valves serve to allow unidirectional flow through the pump module 5010.

The filtration module 5020 preferably includes a filtration membrane 5021$m$ which forms a boundary of cavity 5014$d$, a first support member 5022 with a cut-out center area 5022$c$, a degassing membrane 5022$m$ and second and third support members 5023 and 5024. The filtration membrane 5021$m$ is preferably a 25μ macro-reticular filtration membrane modified to enhance biocompatibility with, for example, blood and to reduce clotting tendencies (like the other supports, filters and membranes in the device). The degassing membrane 5022$m$ is preferably a 0.2-3μ macro-reticular degassing membrane with a reverse flow aqueous pressure differential of at least 100 mmHg for $CO_2$ removal surface modified to enhance biocompatibility.

The first support 5022 includes tubing 5022$t$ for forwarding fluid into the oxygenation module 30, or another adjacent module, if applicable, after it has passed through the filtration membrane 5021$m$ and along the degassing membrane 5022$m$. The second support member 5023 of the filtration module 5020 includes a domed-out fluid cavity 5023$d$ and tubing 5023$t$ through which a vacuum may be applied to the cavity 5023$d$ to draw gas out of the fluid through degassing membrane 5022$m$. The fourth support member 5024 is preferably solid and provides support for the filtration module 5020. The third support member can also include tubing 5024$t$ through which a vacuum may be applied to draw gas out of the fluid through the degassing membrane 5031$m$ of the oxygenation module 5030 as discussed below. The filtration module 5020, or any of the other modules, may also include a port 5023$p$ for sensors or the like.

The oxygenation module 5030 includes a degassing membrane 5031$m$, a first support member 5032, a filtration membrane 5033$m$, an oxygenation membrane 5034$m$, a second support member 5034 with a cut-out center area 5034$c$, and third and fourth support members 5035, 5036. The degassing membrane 5031$m$ is preferably a 0.2-3μ macro-reticular degassing membrane with a reverse flow aqueous pressure differential of at least 100 mmHg surface modified to enhance biocompatibility.

The first support member 5032 includes a domed-out fluid cavity 5032$d$. The surface of the domed-out fluid cavity 5032$d$ preferably forms a tortuous path for the fluid, which enhances the oxygenation and degassing of the fluid. The filtration membrane 5033$m$ is preferably a 25μ macro-reticular filtration membrane modified to enhance biocompatibility. The oxygenation membrane 5034$m$ is preferably a 0.2-1μ macro-reticular oxygenation membrane with a reverse flow aqueous pressure differential of at least 100 mmHg surface modified to enhance biocompatibility.

The second support member 5034 includes tubing 5034$t$ for forwarding fluid out of the oxygenation module 5030 into the debubbler module 5040, or another adjacent module, if applicable. The third support member 5035 includes a domed-out cavity 5035$d$ and tubing 5035$t$ for receiving oxygen from an external source. The fourth support member 5036 is preferably solid and provides support for the oxygenation module 5030.

The debubbler module 5040 includes a first support member 5041, a filtration membrane 5042$m$, a degassing membrane 5043$m$, a second support member 5043 having a cut-out center area 5043$c$, and a third support member 5044. The first support member 5041 has a domed-out fluid cavity 5041$d$.

The filtration membrane 5042$m$ is preferably a 25μ macro-reticular filtration membrane modified to enhance biocompatibility. The degassing membrane 5043$m$ is preferably a 0.2-3μ macro-reticular degassing membrane with a reverse flow aqueous pressure differential of at least 100 mmHg surface modified to enhance biocompatibility. The second support member 5043 has tubing 5043$t$ for forwarding fluid out of the debubbler module 5040 into the pump module 5050, or another adjacent module, if applicable. The third support member 5044 includes a domed-out cavity 5044d and tubing 5044t through which a vacuum may be applied to draw gas out of the fluid through the degassing membrane 5043m.

The second pump module 5050 may correspond to the first pump module 5010. It preferably includes a first support member 5051, a diaphragm 5052, a second support member 5053 with a cut-out center area 5053c, and a third (end) support member 5054. The first support member 5051 includes a domed out fluid cavity 5051d and tubing 5051t for allowing fluid to exit the pump module. The diaphragm 5052 is preferably a polyurethane bladder.

The third (end) support piece member 5054 is preferably solid and provides support for the pump module 5050. Support member 5054 preferably includes a domed out cavity (not shown) for receiving pump fluid. Tubing 5054a is provided to allow the pump fluid such as air to enter the pump module 5050. Preferably hemocompatible anti-backflow valves may serve to allow unidirectional flow through the pump module 5050.

In operation, blood and/or medical fluid enters the first pump module 5010 through tube 5014t passes through the filtration membrane 5021m and along the degassing membrane 5022m. A small vacuum is applied through tubing 5023t to draw gas through the degassing membrane 5022m. Next, the blood and/or medical fluid travels into the oxygenation module 5030 via internal tubing 5022t, passing along the degassing membrane 5031m, through the filtration membrane 5033m and along the oxygenation membrane 5034m. Oxygen is received into the domed-out cavity 5035d of the third support member of the oxygenation module 5030 via tubing 5035t and passes through the oxygenation membrane 5034m into the blood and/or medical fluid as the blood and/or medical fluid travels along its surface.

After being oxygenated by the oxygenation module 5030, the blood and/or medical fluid then travels via internal tubing 5034t into the debubbler module 5040. The blood and/or medical fluid passes through the filtration membrane 5042m and along the degassing membrane 5043m. A small vacuum force is applied through tubing 5044t to draw gas out of the blood and/or medical fluid through the degassing membrane 5043m. After passing through the degassing module 5040, the blood and/or medical fluid travels into the second pump module 5050 through tubing 5041t, and exits the second pump module 5050 via tubing 5051t.

After passing through the oxygenator 110, or alternatively through the combined pump, oxygenation, filtration and/or degassing apparatus 5001, the recirculated medical fluid is selectively either directed to the reservoir 15a or 15b not in use along tubing 92a or 92b, respectively, by activating the respective valve $LV_2$ and $LV_5$ on the tubing 92a or 92b, or into the organ chamber 40 to supplement the organ bath by activating valve $LV_1$. Pressure sensors P3 and P4 monitor the pressure of the medical fluid returned to the bag 15a or 15b not in use. A mechanical safety valve $MV_2$ is provided on tubing 91 to allow for emergency manual cut off of flow therethrough. Also, tubing 96 and manual valve $MV_1$ are provided to allow the apparatus to be drained after use and to operate under a single pass mode in which perfusate exiting the organ is directed to waste rather than being recirculated (recirculation mode.)

A bicarbonate reservoir 130, syringe pump 131 and tubing 132, and an excretion withdrawal unit 120, in communication with a vacuum (not shown) via vacuum valve $VV_2$, and tubing 121a, 122a are also each provided adjacent to and in communication with the organ chamber 40.

Figure 26:
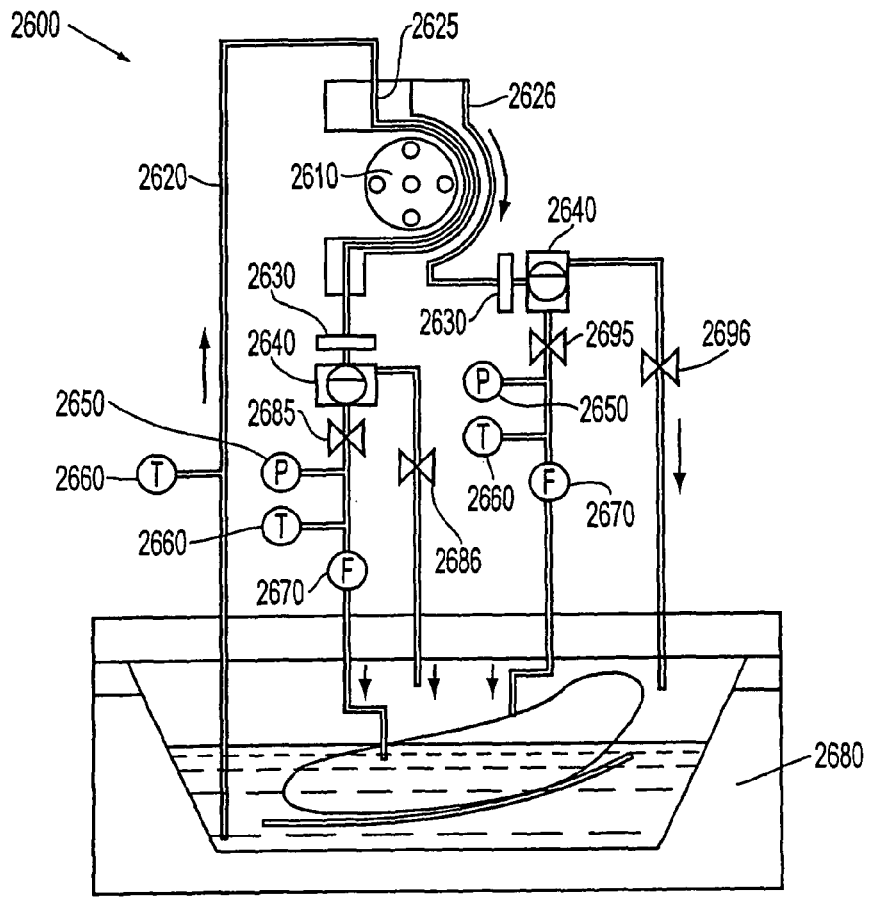
FIG. 26 shows a liver perfusion apparatus according to the present invention.
Figure 27:
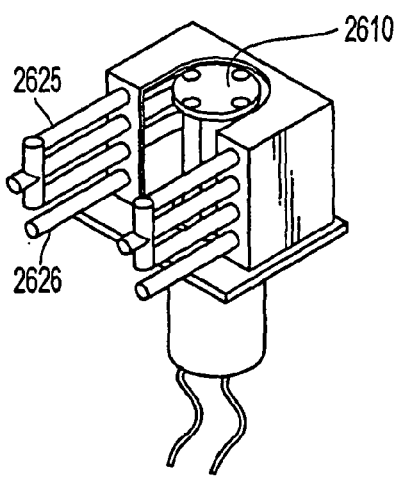
FIG. 27 shows a close-up view of a peristaltic pump for use in a perfusion apparatus according to FIG. 26.

The present invention also provides for perfusion apparatus adapted for organs with complex vasculature structures, such as the liver. Using the liver as an example, FIG. 26 shows perfusion apparatus 2600. Perfusion apparatus 2600 has a single pump 2610, which is preferably a roller pump or peristaltic pump. The tubing splits into two or more directions with, for example, three tubes going toward the portal vein side of the liver (portal tubing 2625) and one tube going toward the hepatic artery side of the liver (hepatic tubing 2626). The portal side of perfusion apparatus 2600 has more tubes because the portal side of the liver uses three to ten times the flow that the hepatic side uses. FIG. 27 shows a perspective view of pump 2610 and the tubing split into portal tubing 2625 and hepatic tubing 2626.

Both the portal side and the hepatic side of perfusion apparatus 2600 preferably have a filter 2630, bubble trap 2640, pressure transducer 2650, temperature transducer 2660, and flow sensor 2670. An additional temperature transducer 2660 may be present in fluid return tubing 2620. The organ may be cooled as discussed above, for example by an ice and water bath 2680 or by a cryogenic fluid. In embodiments using cryogenic fluids, the design should be such that organ freezing is prevented.

Multiple pumps may be used; however, utilizing multiple pumps generally increases the size and cost of the apparatus. Utilizing a single pump 2610 for both vasculature systems provides a variety of modes that can be used to perfuse a liver. After each bubble trap 2640, the tubing splits into two directions. On the hepatic side, hepatic infusion valve 2685 controls the flow to the hepatic side of the liver and hepatic wash valve 2686 controls the flow into the organ bath. On the portal side, portal infusion valve 2695 controls the flow to the portal side of the liver and portal wash valve 2696 controls the flow into the organ bath. Preferably, each pair of infusion valves and wash valves operates in an on/off or either/or manner. In other words, when, for example, the portal side is set to infuse, the portal wash valve 2696 is closed. The following table shows various modes of operation for perfusion apparatus 2600.

| MODES OF OPERATION | PORTAL VALVES | HEPATIC VALVES | DOMINANT PRESSURE | NOTES |
| --- | --- | --- | --- | --- |
| Portal Only | Infuse | Wash | Portal | No hepatic perfusion |
| Portal Priority | Infuse | Infuse | Portal | Hepatic slave to portal |
| Hepatic Only | Wash | Infuse | Hepatic | No portal perfusion |
| Hepatic Priority | Infuse | Infuse | Hepatic | Portal slave to hepatic |
| Alternating | Infuse | Switching | Alternating | Wavy portal flow; pulsed hepatic flow |

The modes of operation identified in the table above show options for infusing a liver. In the first mode, Portal Only, the portal side of the liver is infused. Therefore, the portal valves are set to infuse, which means that portal infusion valve 2695 is open and portal wash valve 2696 is closed. Also, in a Portal Only mode, hepatic infusion valve 2685 is closed and hepatic wash valve 2686 is open. In a Portal Only mode, the portal pressure is dominant, which means the pressure is controlled by the pressure transducer 2650 on the portal side. In this mode, there is no hepatic infusion.

In a Portal Priority mode, the portal valves and the hepatic valves are set to infuse. The portal pressure is dominant; and therefore, the hepatic side is a slave to the portal side. In an Alternating mode, the portal valves are set to infuse and the hepatic valves switch between an infuse setting and a wash setting. In an Alternating mode, when the hepatic valves are set to infuse, the hepatic side provides the dominant pressure. When the hepatic valves are set to wash, the portal side provides the dominant pressure. This type of alternating pressure control provides the portal side with a wavy flow and provides the hepatic side with a pulsed flow.

Figure 28:
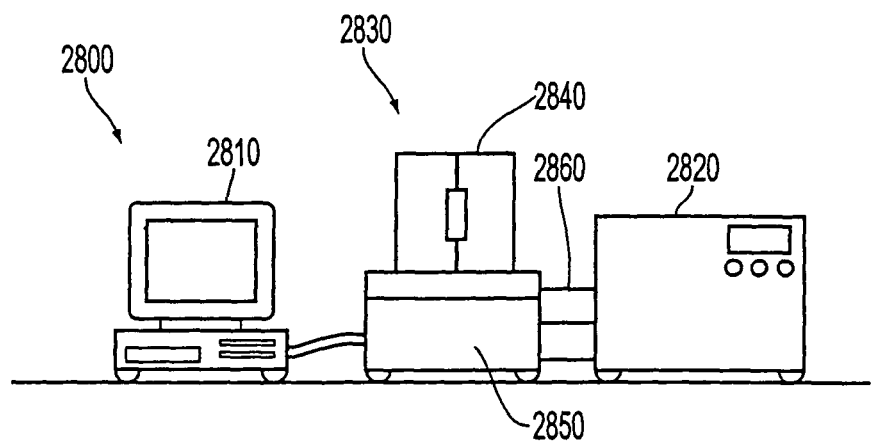
FIG. 28 shows an overall view of an organ diagnostic system according to the present invention.

The present invention also provides an organ diagnostic system 2800 shown in FIG. 28. Organ diagnostic system 2800 has a computer 2810 and an analyzer 2820. Connected to both computer 2810 and analyzer 2820 is an organ evaluation instrument 2830, also shown in FIG. 29. Organ diagnostic system 2800 is preferably provided with suitable displays to show the status of the system and the organ. Organ evaluation instrument 2830 has a perfusate chamber 2840 and an organ chamber 2850. Connecting analyzer 2820 and organ evaluation instrument 2830 is a transfer line 2860. Organ diagnostic system 2800 provides analysis of an organ and produces an organ viability index quickly and in a sterile cassette, preferably transferable from perfusion apparatus 1 and/or transporter 1900. The organ viability index is preferably produced by flow and temperature programmed single-pass perfusion and in-line automatic analysis. The analysis may be performed in a multi-pass system, although a beneficial aspect of the single-pass system is that it can be configured with a limited number of sensors and requires only enough perfusate to perform the analysis. Single-pass perfusion also allows for an organ inflow with a perfusate having a known and predetermined chemistry. This increases the flexibility of types and contents of perfusates that may be delivered, which can be tailored and modified to the particular analysis in process.

Figure 29:
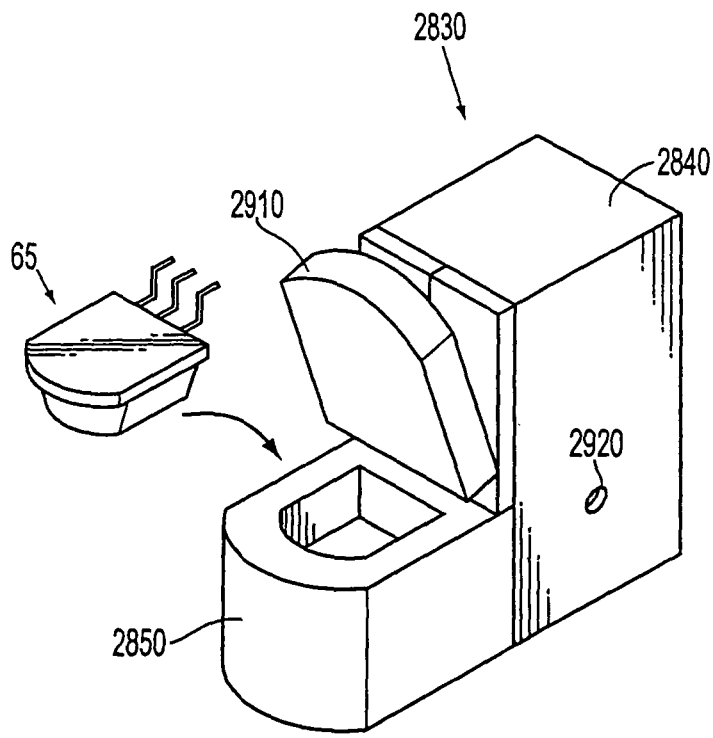
FIG. 29 shows a perspective view of an organ evaluation instrument for use in an organ diagnostic system according to FIG. 28.

FIG. 29 shows a perspective view of organ evaluation instrument 2830. Organ evaluation instrument 2830 has a perfusate chamber 2840 and an organ chamber 2850. Organ chamber 2850 may be insulated and preferably has a lid 2910 that may be removable or may be hinged. Organ chamber 2850 is preferably configured to receive cassette 65, preferably without opening cassette 65 or jeopardizing the sterility of the interior of cassette 65. Cassette 65 and organ chamber 2850 are preferably constructed to fit or mate such that efficient heat transfer is enabled. The geometric elements of cassette 65 and organ chamber 2850 are preferably constructed such that when cassette 65 is placed within organ chamber 2850, the elements are secure for analysis. A port 2920 is also provided to connect transfer line 2860.

Figure 30:
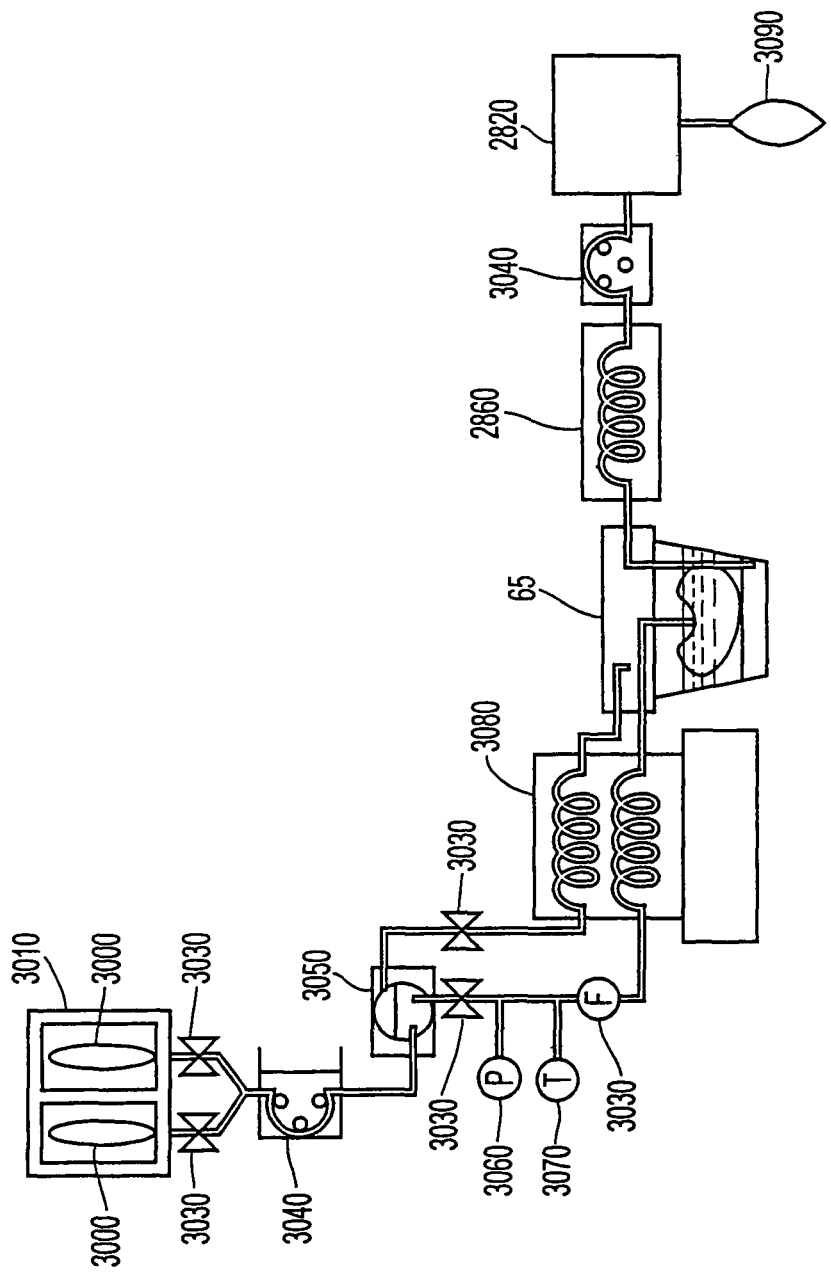
FIG. 30 shows an in-line perfusion system for use in an organ diagnostic system according to FIG. 28.

FIG. 30 shows a single-pass fluid system of organ diagnostic system 2800. The initial perfusion fluids 3000 are contained in a chamber 3010. Chamber 3010 is preferably temperature controlled by a heating and cooling system. Fluid flow within the system is monitored by flow sensor 3020 and controlled by signaling to pinch valves 3030 and pumps 3040. The fluid system also provides a bubble trap 3050, a pressure transducer 3060 and a temperature transducer 3070. Heat exchanger 3080 provides temperature control and heating and cooling to the fluid within the system prior to organ perfusion. The organ is perfused in cassette 65. The fluid in the organ bath may be collected, or the venous outflow may be captured, to be analyzed. The fluid is collected and passed via transfer line 2860 to analyzer 2820. Transfer line 2860 may also be provided with a separate heating and cooling unit. After the fluid is analyzed, it may be collected in a waste receptacle 3090.

Figure 31:
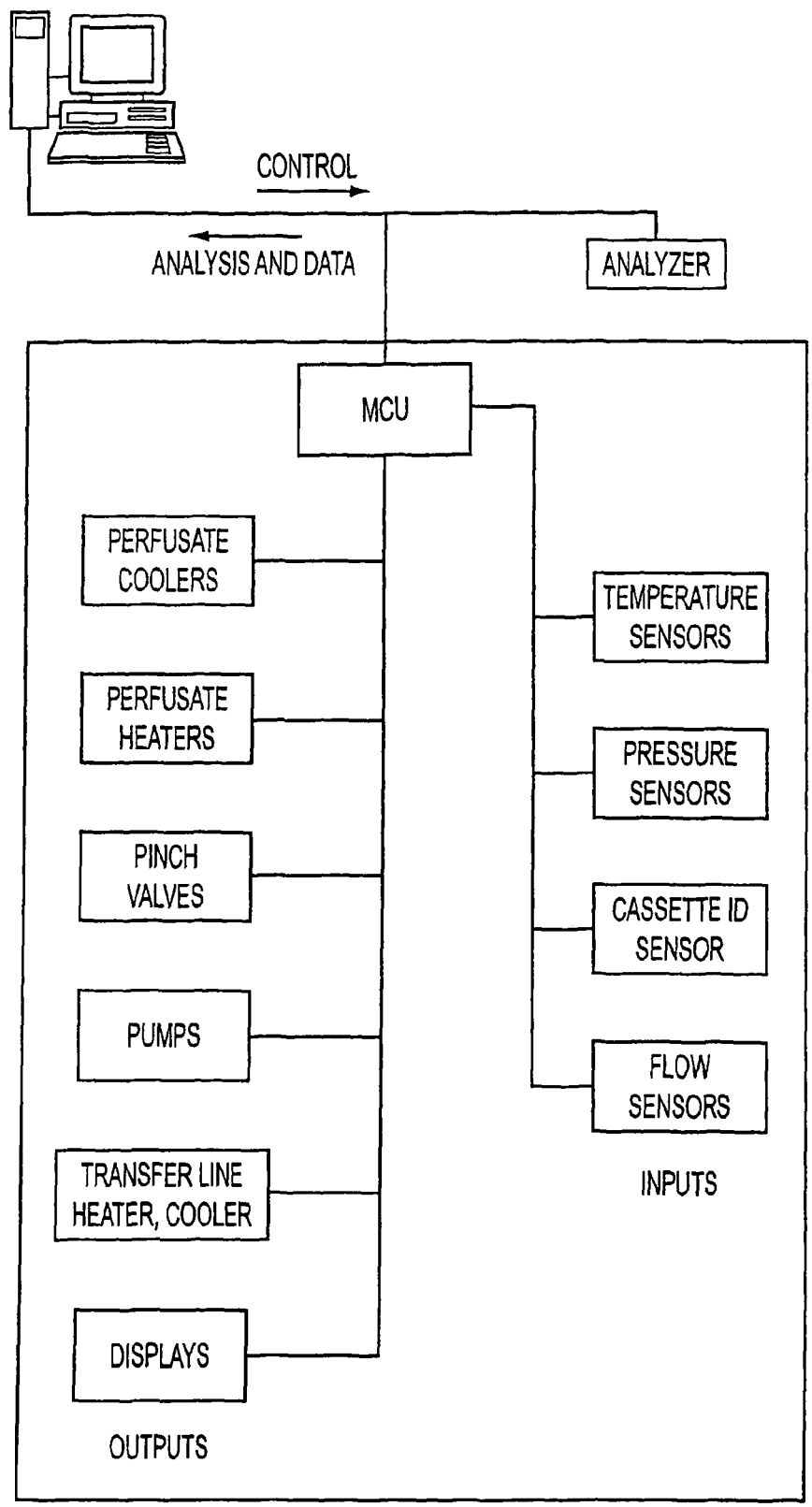
FIG. 31 shows a logic circuit for an organ diagnostic system according to FIG. 28.

FIG. 31 shows a logic circuit for organ diagnostic system 2800. The computer provides control parameters and receives results and data from the analyzer. The logic circuit shows inputs from the sensors to the microcontroller and outputs to hardware elements, such as perfusate coolers, perfusate heaters, pinch valves, pumps, transferline heater/cooler and displays.

The method according to the invention preferably utilizes apparatus such as that discussed above to perfuse an organ to sustain, monitor and/or restore the viability of an organ and/or to transport and/or store the organ. Preservation of the viability of an organ is a key factor to a successful organ transplant. Organs for transplant are often deprived of oxygen (known as ischemia) for extended periods of time due to disease or injury to the donor body, during removal of the organ from the donor body and/or during storage and/or transport to a donee body. The perfusion, diagnostic, and/or transporter apparatus of the present invention have the ability to detect the cell chemistry of an organ to be transplanted in order to adjust the perfusate and control the cellular metabolism to repair ischemic damage to the organ and to prevent reperfusion injury. One specific outcome of ischemic injury may be apoptosis or programmed cell death. Specific agents and additives provided to an organ by the perfusion, diagnostic and/or transporter apparatus, under conditions controlled by the particular apparatus, may interrupt, decrease and/or reverse apoptosis.

In preferred methods of the present invention, an organ or tissue is treated ex vivo by mechanical, physical, chemical or genetic manipulation and/or modification to treat disease and/or treat damage to and/or enhance the properties of the organ or tissue. An organ or tissue sample may be removed from a first body, modified, treated and/or analyzed outside the first body and either returned to the first body or transplanted to a second body. An advantage of the apparatus is that it enlarges the time that an organ may be available for ex vivo treatment, e.g., for hours (e.g. 2, 4, 6, 8, 10, 12 or more hours) or even days (e.g. 2, 4, 6, 8, 10, 12 or more days) or weeks (e.g. 1, 2, 3, 4, 5, 6, 7, 8 or more weeks). In preferred embodiments, the perfusion, diagnostic and/or transporter apparatus of the present invention may be used to provide particular solutions or chemicals to an organ or tissue or may be used to perform particular treatments including flushing or washing an organ or tissue with particular solutions or chemicals. Ex vivo treatments may be performed on tissue or an organ to be transplanted or may be performed on tissue or an organ that has been removed from a patient and is to be returned to the patient after the desired procedure is performed. Ex vivo treatments include but are not limited to treatment of tissue or an organ that has endured a period or periods of ischemia and/or apoxia. Ex vivo treatments may involve performing surgical techniques on an organ, such as cutting and suturing an organ, for example to remove necrotic tissue. Any surgical or other treatment technique that may be performed on tissue or an organ in vivo may also be performed on tissue or an organ ex vivo. The benefit of such ex vivo treatment may be seen, for example, in the application of radiation or chemotherapy to treat a tumor present in or on an organ, to prevent other portions of the patient from being subjected to extraneous radiation or chemotherapy during treatment. The perfusion and transporter apparatus of the present invention also provide additional time for a physician to maintain the tissue or organ before, during and/or after performing a particular technique on the tissue or organ.

Particles trapped in an organ's vasculature may prevent the organ from perfusing properly, or may cause the organ to function improperly, before and/or after transplantation. Perfusion, diagnostic and transporter apparatus of the invention provide ex vivo techniques include perfusing, flushing or washing an organ with suitable amounts of a thrombolytic agent, such as streptokinase, to dissolve blood clots that have formed or to prevent the formation of blood clots in an organ and to open the vasculature of the organ. Such techniques are disclosed, for example, in U.S. Provisional patent application Ser. No. 60/227,843, filed Aug. 25, 2000, the entire disclosure of which is hereby incorporated by reference.

Another concern with organ transplantation is the degree to which a recipient may be medicated to prevent organ rejection. In organ transplantation, a further ex vivo technique involves modifying the organ to avoid having it activate the immune system of the donee to prevent or reduce organ rejection and to limit or prevent the need to suppress the donee's immune system before, during and/or after organ transplantation so as to increase the tolerance of the donee to the transplanted organ. Modifications of an organ may, for example, encourage the donee body to recognize the transplanted organ as autologous. The perfusion, diagnostic and/or transporter apparatus of the present invention may deliver substances such as chemical compounds, natural or modified antibodies, immunotoxins or the like, to an organ and may assist the organ to adsorb, absorb or metabolize such substances to increase the likelihood that the organ will not be rejected. These substances may also mask the organ by blocking, killing, depleting and/or preventing the maturation of allostimulatory cells (dendritic cells, passenger leukocytes, antigen presenting cells, etc.) so that the recipient's immune system does not recognize it or otherwise recognizes the organ as autologous. An organ may be treated just prior to transplantation or may be pretreated hours, days or weeks before transplantation. Such techniques are further described in U.S. Provisional patent application Ser. No. 60/227,841, filed Aug. 25, 2000, the entire disclosure of which is hereby incorporated by reference.

Substances, such as modified or unmodified immunoglobulin, steroids and/or a solution containing polyethylene glycol (PEG) and an antioxidant such as glutathione, may also be provided to an organ or tissue to mask the organ or to treat the onset of intimal hyperplasia during cryopreservation and/or organ or tissue transplantation. These solutions may be provided to an organ or tissue by perfusion, diagnostic and/or transporter apparatus of the invention. Exemplary such solutions and methods are disclosed in U.S. patent application Ser. No. 09/499,520, the entire disclosure of which is hereby incorporated by reference.

The perfusion, diagnostic and transporter apparatus of the invention may be used in conjunction with the above techniques and methods and/or in conjunction with further techniques and methods, to perform research on an organ or tissue. The various apparatus may enlarge the time that an organ may be available for ex vivo treatment, e.g., for hours (e.g. 2, 4, 6, 8, 10, 12 or more hours) or even days (e.g. 2, 4, 6, 8, 10, 12 or more days) or weeks (e.g. 1, 2, 3, 4, 5, 6, 7, 8 or more weeks). During the period in which the organ is preserved and/or maintained, various drug research and development may be performed on and/or with the organ. Further treatments may be performed for research purposes, such as developing immunomodification parameters. Since the organ or tissue may be maintained and/or analyzed at or near physiologic parameters, an organ may be tested for the effects of various treatments and/or substances on the organ or tissue ex vivo. The perfusion, diagnostic and/or transporter apparatus may be used to perfuse blood or a synthetic blood substitute through an organ while monitoring the organ and the organ outflow to analyze the condition of the organ and/or to determine the effect on it of the various treatments.

Preferred methods according to the present invention focus on three concepts in order to preserve an organ's viability prior to transplant of the organ into a donee body—treating the cellular mitochondria to maintain and/or restore pre-ischemia energy and enzyme levels, preventing general tissue damage to the organ, and preventing the washing, away of or damage to the vascular endothelial lining of the organ.

The mitochondria are the energy source in cells. They need large amounts of oxygen to function. When deprived of oxygen, their capacity to produce energy is reduced or inhibited. Additionally, at temperatures below 20° C. the mitochondria are unable to utilize oxygen to produce energy. By perfusing the organ with an oxygen rich medical fluid at normothermic temperatures, the mitochondria are provided with sufficient amounts of oxygen so that pre-ischemia levels of reserve high energy nucleotide, that is, ATP levels, in the organ reduced by the lack of oxygen are maintained and/or restored along with levels of enzymes that protect the organ's cells from free radical scavengers. Pyruvate rich solutions, such as that disclosed in U.S. Pat. No. 5,066,578, are incapable of maintaining and/or restoring an organ's pre-ischemia energy levels and only function in the short term to raise the level of ATP a small amount. That is, organs naturally have significant pyruvate levels. Providing an organ with additional pyruvate will not assist in restoring and/or maintaining the organ's pre-ischemia energy levels if the mitochondria are not provided with sufficient oxygen to produce energy. Thus, the normothermic perfusion fluid may contain pyruvate but may also contain little or no pyruvate. For example, it can contain less than 6 mM of pyruvate, 5 mM, 4 mM, or even no pyruvate. Other known preservation solutions, such as that disclosed in U.S. Pat. No. 5,599,659, also fail to contain sufficient oxygen to restore and/or maintain pre-ischemia energy and enzyme levels.

After maintaining and/or restoring the organ's pre-ischemia energy levels by perfusing the organ with an oxygen rich first medical fluid at normothermic or near-normothermic temperatures (the normothermic mode), the organ is perfused with a second medical fluid at hypothermic temperatures (the hypothermic mode). The hypothermic temperatures slow the organ's metabolism and conserve energy during storage and/or transport of the organ prior to introduction of the organ into a donee body. The medical fluid utilized in the hypothermic mode contains little or no oxygen, which cannot be utilized by mitochondria to produce energy below approximately 20° C. The medical fluid may include antioxidants and other tissue protecting agents, such as, for example, ascorbic acid, glutathione, water soluble vitamin E, catalase, or superoxide dismutase to protect against high free radical formation which occurs at low temperatures due to the reduction in catalase/superoxide dismutase production. Further, various drugs and agents such as hormones, vitamins, nutrients, antibiotics and others may be added to either solution where appropriate. Additionally, vasodilators, such as, for example, peptides, may be added to the medical fluid to maintain flow even in condition of injury.

Prior to any normothermic perfusion with the oxygen rich first medical fluid at normothermic temperatures, the organ may be flushed with a medical solution containing little or no oxygen and preferably containing antioxidants. The flushing is usually performed at hypothermic temperatures but can, if desired and/or as necessary, be performed at normothermic or near-normothermic temperatures. Flushing can be followed by one or more of hypothermic perfusion, normothermic perfusion, and/or static storage, in any necessary and/or desired order. In some cases, normothermic perfusion may not be necessary.

The normothermic perfusion, with or without prior hypothermic flushing, may also be performed on an organ that has already been subjected to hypothermic temperatures under static or perfusion conditions, as well as on normothermic organs.

The organ may be perfused at normothermic or near-normothermic temperatures to sustain, monitor and/or restore its viability prior and/or subsequent to being perfused at hypothermic temperatures for storage and then may be transported without or preferably with hypothermic perfusion. Also, the normothermic perfusion may be performed in vivo prior to removal of the organ from the donor body. Further, the organ may be perfused at normothermic temperatures to sustain, monitor and/or restore its viability prior to being perfused at hypothermic temperatures preparatory to storage and/or transport. Then the organ may be transplanted into a donee body while remaining at hypothermic temperatures, or it may first be subjected to normothermic perfusion to help it recover from the effects of storage and/or transport. In the latter case, it may then be transplanted at normothermic temperatures, or preferably, be hypothermically perfused again for transplantation at hypothermic temperatures. After transplant, the organ may optionally again be perfused at normothermic temperatures in vivo, or allowed to warm up from the circulation of the donee.

Figure 16:
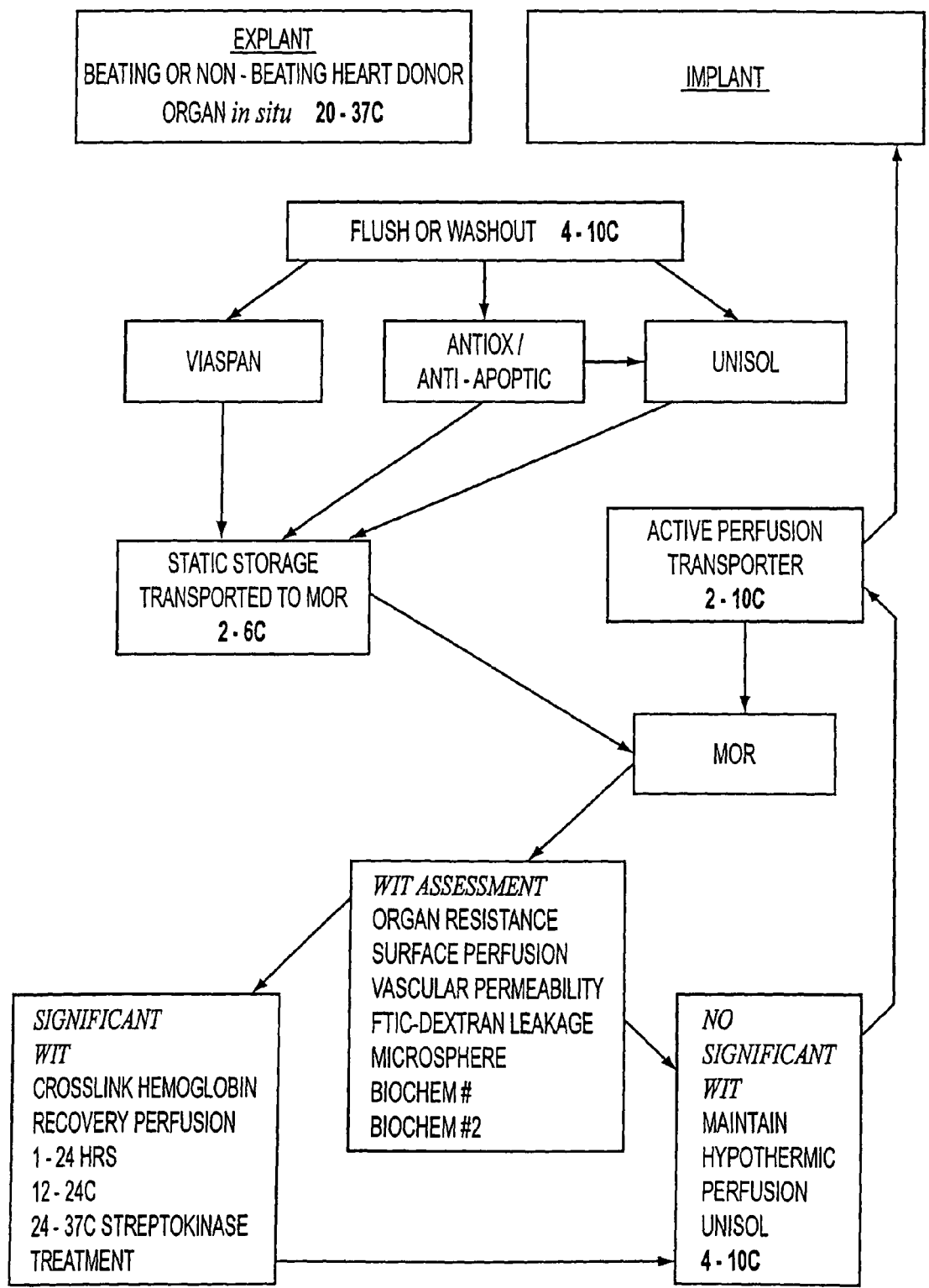
FIG. 16 shows an exemplary diagram of possible processing steps according to the invention.

By way of Example only, and without being limited thereto, FIG. 16 shows an exemplary diagram of possible processing steps according to the invention. The Figure shows various possible processing steps of multiple organ recovery (MOR) from organ explant from the organ donor through implant in the donee, including possible WIT (warm ischemia time) and hypoxia damage assessment. Several exemplary scenarios are set forth in the following discussion.

For example, in one embodiment of the present invention, the organ can be harvested from the donor under beating heart conditions. Following harvesting, the organ can be flushed, such as with any suitable solution or material including, but not limited to VIASPAN (a preservation solution available from DuPont), other crystalloid solution, dextran, HES (hydroxyethyl starch), solutions described in U.S. patent application Ser. No. 09/628,311, filed Jul. 28, 2000, the entire disclosure of which is hereby incorporated by reference, or the like. The organ can then be stored statically, for example, at ice temperatures (for example of from about 1 to about 10° C.).

In another embodiment, such as where the organ has minimal WIT and minimal vascular occlusion, a different procedure can be used. Here, the organ can again be harvested under beating heart conditions, followed by flushing, preferably at hypothermic temperatures. If necessary to transport the organ, the organ can be stored in a suitable transporter at, for example, ice temperatures. Flow to the organ can be controlled by a set pressure maximum, where preset pressure minimum and pressure maximum values control the pulse wave configuration. If necessary to store the organ for a longer period of time, such as for greater than 24 hours, the organ can be placed in the MOR. In the MOR, a suitable perfusate can be used, such as a crystalloid solution, dextran or the like, and preferably at hypothermic temperatures. Preferably, the hypothermic temperatures are from about 4 to about 10° C., but higher or lower temperatures can be used, as desired and/or necessary. Preferably, the perfusate solution contains specific markers to allow for damage assessment, although damage assessment can also be made by other known procedures. When desired, the organ can then be returned to the transporter for transport to the implant site.

As a variation of the above procedure, an organ having minimal WIT and minimal vascular occlusion can be harvested under non-beating heart conditions. Here, the organ can flushed, preferably at hypothermic temperatures and, if necessary, stored for transport in a suitable transporter at, for example, ice temperatures. As above, flow to the organ can be controlled by a set pressure maximum, where preset pressure minimum and pressure maximum values control the pulse wave configuration. The organ can be placed in the MOR, either for extended storage and/or for damage assessment. In the MOR, a suitable perfusate can be used, such as a crystalloid solution, dextran or the like, and preferably at hypothermic temperatures. Preferably, the hypothermic temperatures are from about 4 to about 10° C., but higher or lower temperatures can be used, as desired and/or necessary. Preferably, the perfusate solution contains specific markers to allow for damage assessment, although damage assessment can also be made by other known procedures. Following hypothermic perfusion, a second perfusion can be utilized, preferably at normothermic temperatures. Any suitable perfusion solution can be used for this process, including solutions that contain, as desired, oxygenated media, nutrients, and/or growth factors. Preferably, the normothermic temperatures are from about 12 to about 24° C., but higher or lower temperatures can be used, as desired and/or necessary. The normothermic perfusion can be conducted for any suitable period of time, for example, for from about 1 hour to about 24 hours. Following recovery from the normothermic perfusion, the organ is preferably returned to a hypothermic profusion using, for example, a suitable solution such as a crystalloid solution, dextran or the like, and preferably at hypothermic temperatures. When desired, the organ can then be returned to the transporter for transport to the implant site.

In embodiments where the organ has high WIT, and/or where there is a high likelihood of or actual; vascular occlusion, variations on the above processes can be used. For example, in the case where the organ is harvested under non-beating heart conditions, the organ can be flushed as described above. In addition, however, free radical scavengers can be added to the flush solution, if desired. As above, the organ can be stored for transport in a suitable transporter at, for example, ice temperatures, where flow to the organ can be controlled by a set pressure maximum, and where preset pressure minimum and pressure maximum values control the pulse wave configuration. The organ can be placed in the MOR, either for extended storage and/or for damage assessment. In the MOR, a suitable perfusate can be used, such as a crystalloid solution, dextran or the like, and preferably at hypothermic temperatures. Preferably, the hypothermic temperatures are from about 4 to about 10° C., but higher or lower temperatures can be used, as desired and/or necessary. Preferably, the perfusate solution contains specific markers to allow for damage assessment, although damage assessment can also be made by other known procedures. Following hypothermic perfusion, a second perfusion can be utilized, preferably at normothermic temperatures. Any suitable perfusion solution can be used for this process, including solutions that contain, as desired, oxygenated media, nutrients, and/or growth factors. Preferably, the normothermic temperatures are from about 12 to about 24° C., but higher or lower temperatures can be used, as desired and/or necessary. The normothermic perfusion can be conducted for any suitable period of time, for example, for from about 1 hour to about 24 hours. If desired, and particularly in the event that vascular occlusion is determined or assumed to be present, a further perfusion can be conducted at higher normothermic temperatures, for example of from about 24 to about 37° C. This further perfusion can be conducted using a suitable solution that contains a desired material to retard the vascular occlusion. Such materials include, for example, clotbusters such as streptokinase. Following recovery from the normothermic perfusion(s), the organ is preferably returned to a hypothermic profusion using, for example, a suitable solution such as a crystalloid solution, dextran or the like, and preferably at hypothermic temperatures. When desired, the organ can then be returned to the transporter for transport to the implant site.

The organ cassette according to the present invention allows an organ(s) to be easily transported to an organ recipient and/or between organ perfusion, diagnostic and/or portable transporter apparatus, such as, for example, transporter 1900 described above or a conventional cooler or a portable container such as that disclosed in co-pending U.S. application Ser. No. 09/161,919. Because the organ cassette may be provided with openings to allow the insertion of tubing of an organ perfusion, transporter or diagnostic apparatus into the cassette for connection to an organ disposed therein, or may be provided with its own tubing and connection device or devices to allow connection to tubing from an organ perfusion, transporter or diagnostic apparatus and/or also with its own valve, it provides a protective environment for an organ for storage, analysis and/or transport while facilitating insertion of the organ into and/or connection of an organ to the tubing of an organ perfusion, transporter or diagnostic device. Further, the organ cassette may also include a handle to facilitate transport of the cassette and may be formed of a transparent material so the organ may be visually monitored.

Optionally, transporter 1900 and/or cassette 65 may include a Global Positioning System (GPS) (not shown) to allow tracking of the location of the organ(s). The apparatus may also include a data logger and/or transmitter (not shown) to allow monitoring of the organ(s) at the location of the apparatus or at another location.

The method of the invention will be discussed below in terms of the operation of the apparatus shown in FIG. 2. However, other apparatus may be used to perform the inventive method.

As previously discussed, the apparatus discussed above can operate in two modes: a normothermic perfusion mode and a hypothermic perfusion mode. The normothermic perfusion mode will be discussed first followed by a discussion of hypothermic perfusion mode. Repetitive description will be omitted as much as possible.

In the normothermic or near-normothermic perfusion mode, an organ is perfused for preferably ½ to 6 hours, more preferably ½ to 4 hours, most preferably ½ to 1 hour, with a medical fluid maintained preferably within a range of approximately 10° C. to 38° C., more preferably 12° C. to 35° C., most preferably 12° C. to 24° C. or 18° C. to 24° C. (for example, room temperature 22-23° C.) by the thermoelectric unit 30*a* disposed in heat exchange communication with the medical fluid reservoir 10.

As discussed above, in this mode, the medical fluid is preferably an oxygenated cross-linked hemoglobin-based bicarbonate solution. Cross-linked hemoglobin-based medical fluids can deliver up to 150 times more oxygen to an organ per perfusate volume than, for example, a simple University of Wisconsin (UW) gluconate type perfusate. This allows normothermic perfusion for one to two hours to partially or totally restore depleted ATP levels. However, the invention is not limited to this preservation solution. Other preservation solutions, such as those disclosed in U.S. Pat. Nos. 5,149,321, 5,234,405 and 5,395,314 and co-pending U.S. patent application Ser. No. 08/484,601 and U.S. patent application Ser. No. 09/628,311, filed Jul. 28, 2000, the entire disclosures of which are hereby incorporated by reference, may also be appropriate.

In the normothermic perfusion mode, the medical fluid is fed directly to an organ disposed within the organ chamber 40 from one or the other of bags 15*a*, 15*b* via tubing 50*a*,50*b*,50*c* or 50*d*,50*e*,50*c*, respectively. The organ is perfused at flow rates preferably within a range of approximately 3 to 5 ml/gram/min. Pressure sensor P1 relays the perfusion pressure to the microprocessor 150, which varies the pressure supplied by the pressure source 20 to control the perfusion pressure and/or displays the pressure on the control and display areas 5*a* for manual adjustment. The pressure is preferably controlled within a range of approximately 10 to 100 mm Hg, preferably 50 to 90 mm Hg, by the combination of the pressure source 20 and pressure cuff 15*a*, 15*b* in use and the stepping motor/cam valve 65. The compressor and cuffs provide gross pressure control. The stepping motor/cam valve 65 (or other variable valve or pressure regulator), which is also controlled by the operator, or by the microprocessor 150 in response to signals from the pressure sensor P1, further reduces and fine tunes the pressure and/or puts a pulse wave on the flow into the organ 60. If the perfusion pressure exceeds a predetermined limit, the stepping motor/cam valve 65 may be activated to shut off fluid flow to the organ 60.

The specific pressures, flow rates and length of perfusion time at the particular temperatures will vary depending on the particular organ or organs being perfused. For example, hearts and kidneys are preferably perfused at a pressure of approximately 10 to 100 mm Hg and a flow rate of approximately 3 to 5 ml/gram/min. for up to approximately 2 to 4 hours at normothermic temperatures to maintain and/or restore the viability of the organ by restoring and/or maintaining pre-ischemia energy levels of the organ, and are then preferably perfused at a pressure of approximately 10 to 30 mm Hg and a flow rate of approximately 1 to 2 ml/gram/min. for as long as approximately 72 hours to 7 days at hypothermic temperatures for storage and/or transport. However, these criteria will vary depending on the condition of the particular organ, the donor body and/or the donee body and/or on the size of the particular organ. One of ordinary skill in the art can select appropriate conditions without undue experimentation in view of the guidance set forth herein.

Effluent medical fluid collects in the bottom of the organ chamber 40 and is maintained within the stated temperature range by the second thermoelectric unit 30*b*. The temperature sensor T2 relays the organ temperature to the microprocessor 150, which controls the thermoelectric unit 30*a* to adjust the temperature of the medical fluid and organ bath to maintain the organ 60 at the desired temperature, and/or displays the temperature on the control and display areas 5*c* for manual adjustment.

Collected effluent medical fluid is pumped out by the pump 80 via tubing 81 through the filter unit 82 and then returned to the organ bath. This filters out surgical and/or cellular debris from the effluent medical fluid and then returns filtered medical fluid to act as the bath for the organ 60. Once the level sensor L2 senses that a predetermined level of effluent medical fluid is present in the organ chamber 40 (preferably enough to maintain the organ 60 immersed in effluent medical fluid), additional effluent medical fluid is pumped out by the pump 90 through tubing 91. The temperature sensor T1 relays the temperature of the organ bath to the microprocessor 150, which controls the thermoelectric unit 30*b* to adjust the temperature of the medical fluid to maintain the organ 60 at the desired temperature and/or displays the temperature on the control and display area 5*c* for manual adjustment and monitoring.

As noted above, the medical fluid can be directed to waste in a single pass mode or recirculated eventually back to the organ and/or bath (recirculation mode.)

Along tubing 91, the recirculated medical fluid is first pumped through the filter unit 95. Use of a cross-linked hemoglobin medical fluid allows the use of sub-micron filtration to remove large surgical debris and cellular debris, as well as bacteria. This allows the use of minimal antibiotic levels, aiding in preventing organ damage such as renal damage.

Next, the recirculated medical fluid is pumped through the $CO_2$ scrubber/$O_2$ membrane 100. The medical fluid passes over the hydrophobic macroporous membrane with a hydrophilic coating (for example, Hypol) and a low vacuum is applied on the opposite side by activating valve $VV_1$ which removes $CO_2$ from the recirculated medical fluid.

Subsequently, a portion of the medical fluid then enters the oxygenator 110 (for example, a JOSTRA™ oxygenator) and a portion is diverted therearound passing via tubing 111 though the pH, $pO_2$, $pCO_2$, LDH, T/GST and Tprotein sensor V1. At this point two gases, preferably 100% oxygen and 95/5% oxygen/carbon dioxide, are respectively placed on the opposite sides of the membrane depending on the pH level of the diverted medical fluid. The gases are applied at a pressure of up to 200 mm Hg, preferably 50 to 100 mm Hg, preferably through a micrometer gas valve $GV_3$. The cross-linked hemoglobin-based bicarbonate medical fluid may be formulated to require a $pCO_2$ of approximately 40 mm Hg to be at the mid point (7.35) of a preferred pH range of 7.25-7.45.

If the medical fluid exiting the oxygenator is within the preferred pH range (e.g., 7.25-7.45), 100% oxygen is delivered to the gas exchange chamber, and valve $LV_1$ is then not opened, allowing the perfusate to return to the reservoir 10 into the bag 15a or 15b not in use. If the returning perfusate pH is outside the range on the acidic side (e.g., less than 7.25), 100% oxygen is delivered to the gas exchange chamber and valve $LV_1$ is then opened allowing the perfusate to return to the organ chamber 40. Actuation of syringe pump 131 pumps, for example, one cc of a bicarbonate solution from the bicarbonate reservoir 130, via tubing 132 into the organ bath. Medical fluids with high hemoglobin content provide significant buffering capacity. The addition of bicarbonate aids in buffering capacity and providing a reversible pH control mechanism.

If the returning perfusate pH is outside the range on the basic side (e.g., greater than 7.25), 95/5% oxygen/carbon dioxide is delivered to the gas exchange chamber and valve $LV_1$ is not actuated, allowing the perfusate to return to the bag 15a or 15b not in use. The bag 15a or 15b not in use is allowed to degas (e.g., any excess oxygen) through valve $GV_4$. When the bag 15a or 15b in use has approximately 250 ml or less of medical fluid remaining therein, its respective cuff 16a, 16b is allowed to vent via its respective gas valve $GV_1$, $GV_2$. Then, the respective cuff 16a, 16b of the bag 15a or 15b previously not in use is supplied with gas from the compressed gas source 20 to deliver medical fluid to the organ to continue perfusion of the organ.

In the hypothermic mode, an organ is perfused with a cooled medical fluid, preferably at a temperature within a range of approximately 1° C. to 15° C., more preferably 4° C. to 10° C., most preferably around 10° C. The medical fluid is preferably a crystalloid perfusate without oxygenation and preferably supplemented with antioxidants and other tissue protecting agents, such as, for example, ascorbic acid, glutathione, water soluble vitamin E, catalase, or superoxide dismutase.

Instead of feeding the medical fluid directly to the organ, the medical fluid may be fed from the reservoir tank 17 via tubing 51 into an intermediary tank 70 preferably having a pressure head of approximately 5 to 40 mm Hg, more preferably 10 to 30 mm Hg, most preferably around 20 mm Hg. Medical fluid is then fed by gravity or, preferably, pressure, from the intermediary tank 70 to the organ 60 along tubing 50c by activating a valve $LV_6$. The level sensor 71 in the intermediary tank 70 is used to control the feed from reservoir tank 17 to maintain the desired pressure head. Because the medical fluid is fed to the organ by gravity or, preferably, pressure, in the hypothermic mode, there is less perfusion pressure induced damage to the delicate microvasculature of the organ. In fact, the pressure at which the organ is perfused is limited by the pressure head to at most 40 mm Hg.

The stepping motor/cam valve 205 (or other variable valve or pressure regulator) may be arranged on the tubing 50c to provide pulsatile delivery of the medical fluid to the organ 60, to decrease the pressure of the medical fluid fed into the organ 60 for control purposes, or to stop flow of medical fluid into the organ 60, as described above.

Further, in the hypothermic mode, because the organ 60 has less of a demand for nutrients, the medical fluid may be provided to the organ 60 intermittently (e.g., every two hours at a flow rate of up to approximately 100 ml/min.), or at a slow continuous flow rate (e.g., up to approximately 100 ml/min.) over a long period of time. Intermittent perfusion can be implemented in the single pass mode or recirculation mode. The pump 80, filter unit 82 and tube 81 may be used to filter the organ bath along with use of the pH, $pO_2$, $pCO_2$, LDH, T/GST and Tprotein sensor; however, because the organ is unable to utilize oxygen at hypothermic temperatures, the oxygenator is not used. If desired and/or necessary, adequate oxygen can be obtained from filtered room air or other suitable source.

Both the perfusate flow and the temperature regulation can be automatically controlled. Such automatic control allows a rapid and reliable response to perfusion conditions during operation. Automatic flow control can be based on the parameters measured from the system, including the perfusate flow rate, the perfusate pH exiting the organ, the organ inlet pressure or timed sequences such as pre-selected flow rates or switching between perfusate modes. Preferably, the flow control is based on pressure monitoring of the perfusate inflow into the organ. The benefits of automatic flow control include maintaining proper oxygenation and pH control while operating under continuous flow or controlled intermittent flow. Thermal control of the thermoelectric devices (TED) can regulate the temperature of the organ cassette or container and the perfusate reservoir. The thermal control is based on thermal measurements made for example by thermistor probes in the perfusate solution or inside the organ or by sensors in the TED.

The automatic control is preferably effected by an interactive control program using easily operated menu icons and displays. The parameters may be prestored for selection by a user or programmed by the user during operation of the system. The control program is preferably implemented on a programmed general purpose computer. However, the controller can also be implemented on a special purpose computer, a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA or PAL, or the like. In general, any device capable of implementing a finite state machine that is in turn capable of implementing the control process described herein may be used. The control program is preferably implemented using a ROM. However, it may also be implemented using a PROM, an EPROM, an EEPROM, an optical ROM disk, such as a CD-ROM or DVD-ROM, and disk drive or the like. However, if desired, the control program may be employed using static or dynamic RAM. It may also be implemented using a floppy disk and disk drive, a writable optical disk and disk drive, a hard drive, flash memory or the like.

Figure 15:
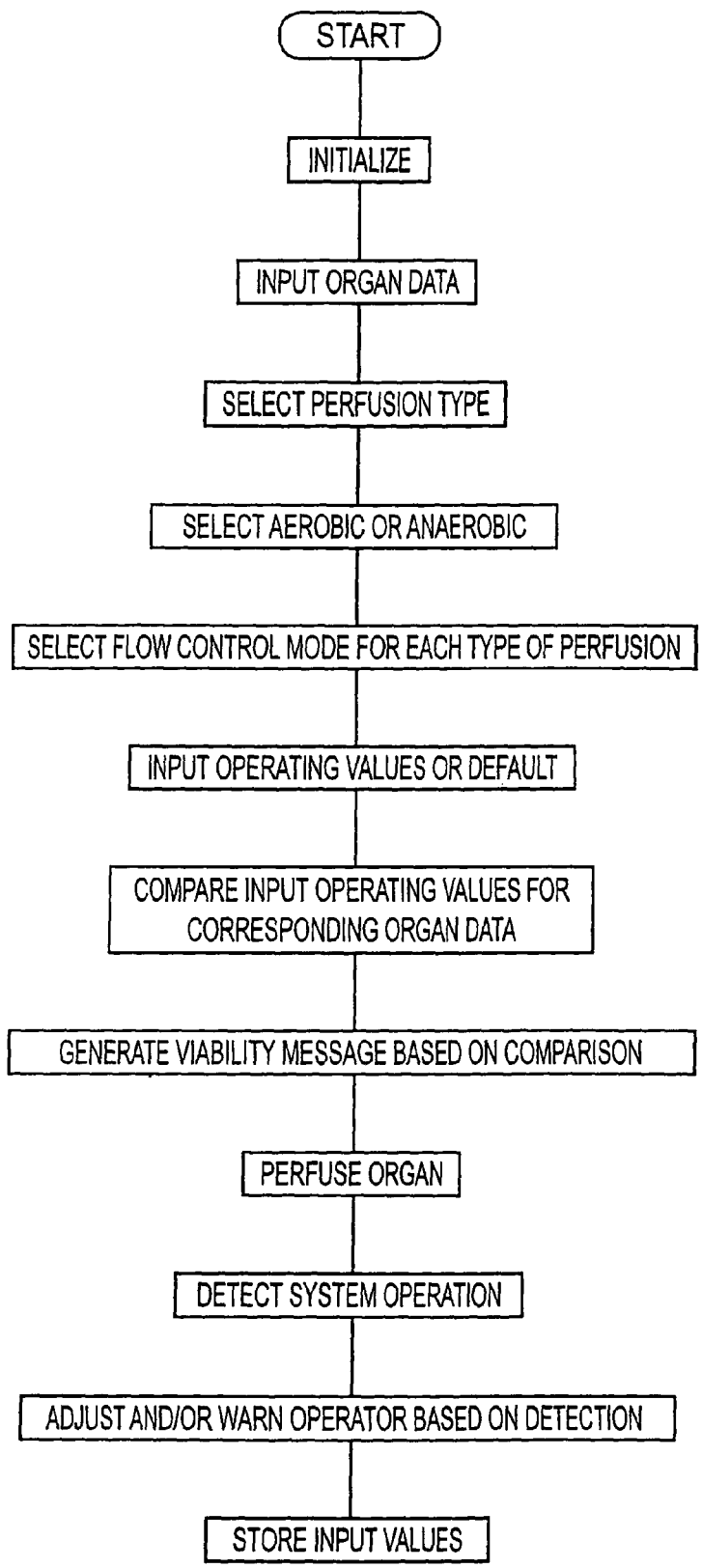
FIG. 15 shows a block diagram that schematically illustrates a control system according to the invention.

In operation, as seen in FIG. 15, the basic steps of operation to control perfusion of one or more organs include first inputting organ data. The organ data includes at least the type of organ and the mass. Then, the program will prompt the user to select one or more types of perfusion modes. The types of perfusion modes, discussed above, include hypothermic perfusion, normothermic perfusion, and sequential perfusion using both normothermic and hypothermic perfusion. When both normothermic and hypothermic perfusion are employed, the user can select between medical fluids at different temperatures. Of course, the system includes default values based on previously stored values appropriate for the particular organ. The user may also select intermittent perfusion, single pass perfusion, and recirculation perfusion. Depending on the type of perfusion selected, aerobic or anaerobic medical fluids may be specified.

Next, the type of flow control for each selected perfusion mode is set. The flow control selector selects flow control based on at least one of perfusate flow rate, perfusate pH, organ inlet pressure and timed sequences. In the preferred embodiment, the flow control is based on detected pressure at the perfusion inlet to the organ. The flow of the medical fluid is then based on the selected perfusion mode and flow control.

During operation the conditions experienced by the system, in particular by the organ and the perfusate, are detected and monitored. The detected operating conditions are compared with prestored operating conditions. A signal can then be generated indicative of organ viability based on the comparison. The various detectors, sensors and monitoring devices are described above, but include at least a pressure sensor, a pH detector, an oxygen sensor and a flow meter.

The control system may also include a thermal controller for controlling temperature of at least one of the perfusate and the organ. The thermal controller can control the temperature of the medical fluid reservoirs and the organ container by controlling the TEDs. As noted above, temperature sensors are connected to the controller to facilitate monitoring and control.

The control system may be manually adjusted at any time or set to follow default settings. The system includes a logic circuit to prevent the operator from setting parameters that would compromise the organ's viability. As noted above, the system may also be operated in a manual mode for sequential hypothermic and/or normothermic perfusion, as well as in the computer controlled mode for sequential hypothermic and/or normothermic perfusion.

The above described apparatus and method may be used for child or small organs as well as for large or adult organs with modification as needed of the cassettes and or of the pressures and flow rates accordingly. As previously discussed, the organ cassette(s) can be configured to the shapes and sizes of specific organs or organ sizes. The apparatus and method can also be used to provide an artificial blood supply to, such, for example, artificial placentas cell cultures, for growing/cloning organ(s).

While the invention has been described in conjunction with specific embodiments thereof, it is evident that many alternatives, modifications and variations may be apparent to those skilled in the art. Accordingly, the preferred embodiments of the invention as set forth herein are intended to be illustrative, not limiting. Various changes may be made without departing from the spirit and scope of the invention.

What is claimed is:

1. A sterilized disposable kit, comprising:
    an organ cassette for independently holding an organ, the organ cassette including an organ supporting surface that supports the organ, the organ cassette being structured to be removably received by a portable organ perfusion apparatus;
    at least one of tubing and a connector configured to allow connection of the organ in the organ cassette to tubing in a recirculating arrangement; and
    a first lid attachable to the cassette and a second lid attachable to the cassette, wherein at least one of the first lid and the second lid is openable without exposing an interior of the cassette when the first lid and the second lid arc attached to the cassette.

2. A sterilized disposable kit according to claim 1, wherein the recirculating arrangement is configured to divert fluid flow into a perfusate bath surrounding an organ when perfusion pressure rises above a level suitable for an organ.

3. A sterilized disposable kit according to 1, wherein the organ cassette maintains uninterrupted sterile conditions inside the organ cassette when being removably received by the portable organ perfusion apparatus.

4. A sterilized disposable kit according to claim 1, wherein the second lid is configured to be interior to the first lid in use.

5. A sterilized disposable kit according to claim 1, wherein the first lid and the second lid are each configured to form a seal with the cassette.

6. A kit comprising:
    a saleable package containing a portable housing, a set of tubes, an organ supporting surface, a first lid attachable to the portable housing, and a second lid attachable to the portable housing, wherein
    at least one of the first lid and the second lid is openable without exposing an interior of the portable housing when the first lid and the second lid are attached to the portable housing,
    the organ supporting surface is configured to support an organ within said portable housing,
    the portable housing is configured to be received by at least one of an organ perfusion device, an organ transporter and an organ diagnostic device, and includes one or more openings configured to allow the set of tubes to be connected to the organ by way of the one or more openings in a recirculating arrangement, and
    a bottom portion of the housing is liquid-tight.

7. A kit according to claim 6, wherein the recirculating arrangement is configured to divert fluid flow into a perfusate bath surrounding an organ when perfusion pressure rises above a level suitable for an organ.

8. A kit according to claim 6, wherein the portable housing is configured to maintain uninterrupted sterile conditions inside the portable housing when being removably received by at least one of the organ perfusion device, the organ transporter and the organ diagnostic device.

9. A kit according to claim 6, wherein the second lid is configured to be interior to the first lid in use.

10. A kit according to claim 6, wherein the first lid and the second lid are each configured to form a seal with the portable housing.

* * * * *